(12) United States Patent
Bourke, Jr. et al.

(10) Patent No.: US 11,833,367 B2
(45) Date of Patent: Dec. 5, 2023

(54) METHODS, DEVICES, AND COMPOSITIONS FOR MEASURING AND INDUCING CELL-TO-CELL COMMUNICATION, AND THERAPEUTIC USES THEREOF

(71) Applicant: IMMUNOLIGHT, LLC., Detroit, MI (US)

(72) Inventors: Frederic A. Bourke, Jr., Aspen, CO (US); Harold Walder, Oak Island, NC (US); Zakaryae Fathi, Raleigh, NC (US); Wayne F. Beyer, Jr., Ivanhoe, VA (US); Ronald A. Rudder, Bristow, VA (US)

(73) Assignee: IMMUNOLIGHT, LLC.

( * ) Notice: Subject to any disclaimer, the term of this patent is extended or adjusted under 35 U.S.C. 154(b) by 1072 days.

(21) Appl. No.: 16/599,732

(22) Filed: Oct. 11, 2019

(65) Prior Publication Data

US 2020/0114164 A1     Apr. 16, 2020

Related U.S. Application Data

(60) Provisional application No. 62/745,057, filed on Oct. 12, 2018.

(51) Int. Cl.
| | |
|---|---|
| *A61N 5/06* | (2006.01) |
| *A61N 5/10* | (2006.01) |
| *A61N 5/02* | (2006.01) |
| *A61K 49/00* | (2006.01) |
| *A61K 41/00* | (2020.01) |

(52) U.S. Cl.
CPC .......... *A61N 5/062* (2013.01); *A61K 41/0057* (2013.01); *A61K 49/0015* (2013.01); *A61N 5/025* (2013.01); *A61N 5/0622* (2013.01); *A61N 5/10* (2013.01); *A61N 2005/0661* (2013.01)

(58) Field of Classification Search
CPC ...... A61N 5/062; A61N 5/025; A61N 5/0622; A61N 5/10; A61N 2005/0661; A61N 1/403; A61N 2/02; A61N 2005/0659; A61K 41/0057; A61K 49/0015; A61M 37/00; A61M 2037/0007
See application file for complete search history.

(56) References Cited

U.S. PATENT DOCUMENTS

| | | | |
|---|---|---|---|
| 6,036,923 A | 3/2000 | Laugharn, Jr. et al. | |
| 6,173,202 B1 | 1/2001 | Eppstein | |
| 6,245,967 B1 | 6/2001 | Sonnewald et al. | |
| 8,630,704 B2 | 1/2014 | Pu et al. | |
| 2003/0233122 A1 | 12/2003 | Azure | |
| 2004/0034388 A1 | 2/2004 | Azure | |
| 2004/0068284 A1 | 4/2004 | Barrows | |
| 2005/0143791 A1 | 6/2005 | Hameroff | |
| 2007/0183132 A1 | 8/2007 | Ung | |
| 2007/0203655 A1 | 8/2007 | Hu | |
| 2007/0265663 A1 | 11/2007 | Azure | |
| 2008/0233308 A1 | 9/2008 | Mosaico | |
| 2009/0099503 A1 | 4/2009 | Mitsuda | |
| 2011/0236325 A1 | 9/2011 | Mitchell et al. | |
| 2013/0041206 A1 | 2/2013 | Andersson | |
| 2014/0276354 A1 | 9/2014 | Piergallini et al. | |
| 2015/0231557 A1 | 8/2015 | Miller et al. | |
| 2016/0030564 A1 | 2/2016 | Loupis et al. | |
| 2017/0080246 A1 | 3/2017 | Knight | |
| 2017/0151332 A1 | 6/2017 | Piergallini et al. | |
| 2017/0157418 A1 | 6/2017 | Oldham et al. | |
| 2017/0239489 A1 | 8/2017 | Bourke, Jr. et al. | |
| 2019/0046643 A1 | 2/2019 | Loupis et al. | |

FOREIGN PATENT DOCUMENTS

WO    WO 2017/189506 A1    11/2017

OTHER PUBLICATIONS

Anvari et al. "Grand Challenges and Opportunities in Biophotonics." Front. Photon., Jun. 22, 2021 (Year: 2012).*
Hottinger et al. Tumor treating fields: a novel treatment modality and its use in brain tumors. Neuro Oncol. Oct. 2016; 18(10): 1338-1349. (Year: 2016).*
Rahman et al.I, "The Impact of Pulse Electric Field Treatment and Selected Bioactive Compound Extract toward Anticancer Treatment," 2018 9th IEEE Control and System Graduate Research Colloquium (ICSGRC), Shah Alam, Malaysia, 2018, pp. 244-247, doi: 10.1109/ICSGRC.2018.86 (Year: 2018).*
European Office Action dated May 30, 2022 in European Patent Application No. 19870333.2, 17 pages.
International Search Report and Written Opinion dated Feb. 3, 2020, in PCT/US2019/055912, 37 pages.

\* cited by examiner

*Primary Examiner* — Titilayo Moloye
(74) *Attorney, Agent, or Firm* — TUCKER ELLIS LLP; J. Derek Mason

(57) ABSTRACT

Methods of treating a subject are provided, involving providing a first region of biological material coupled to the subject; initiating a change in a cellular environment of the cells in the first region; and due to a change in biological or chemical activity of the cells in the first region, inducing a biological change in a second region inside the subject, along with various biophoton collectors and biophoton bypasses useful for implementing a variety of the method embodiments.

42 Claims, 45 Drawing Sheets

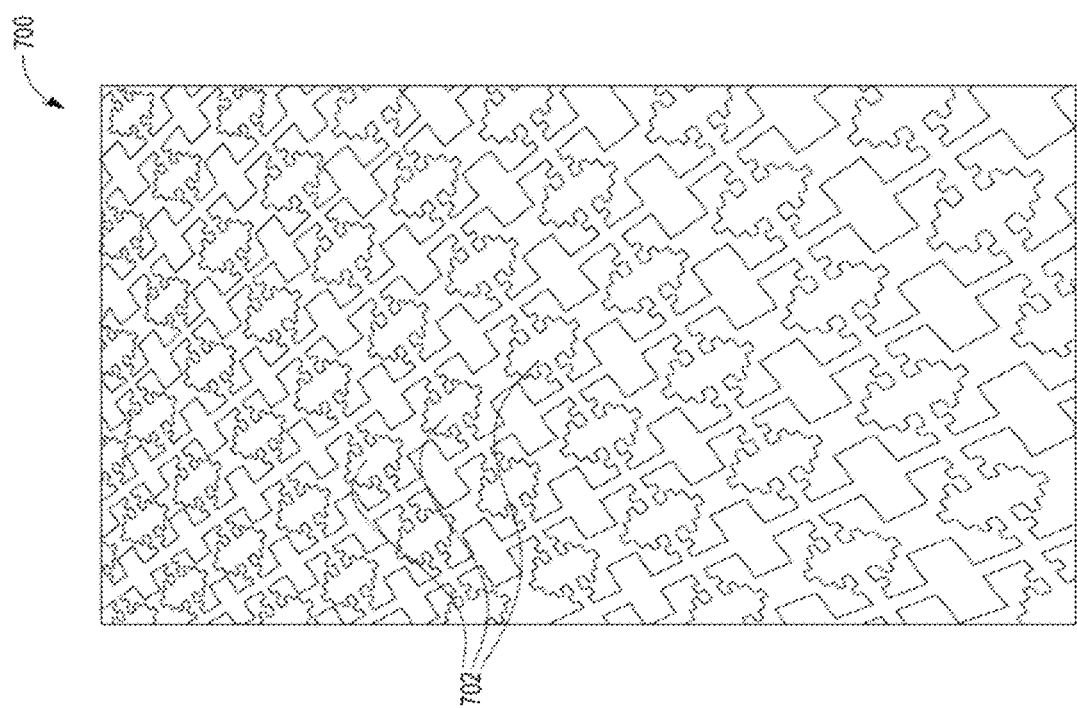

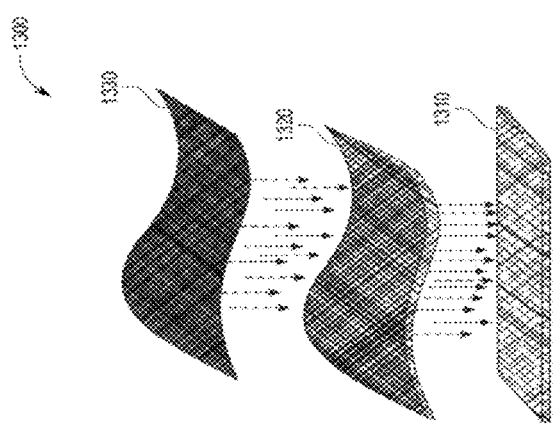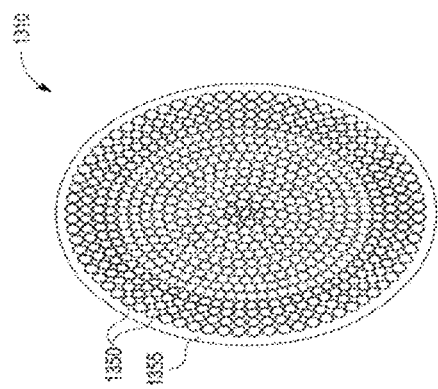
FIG. 13A
FIG. 13B

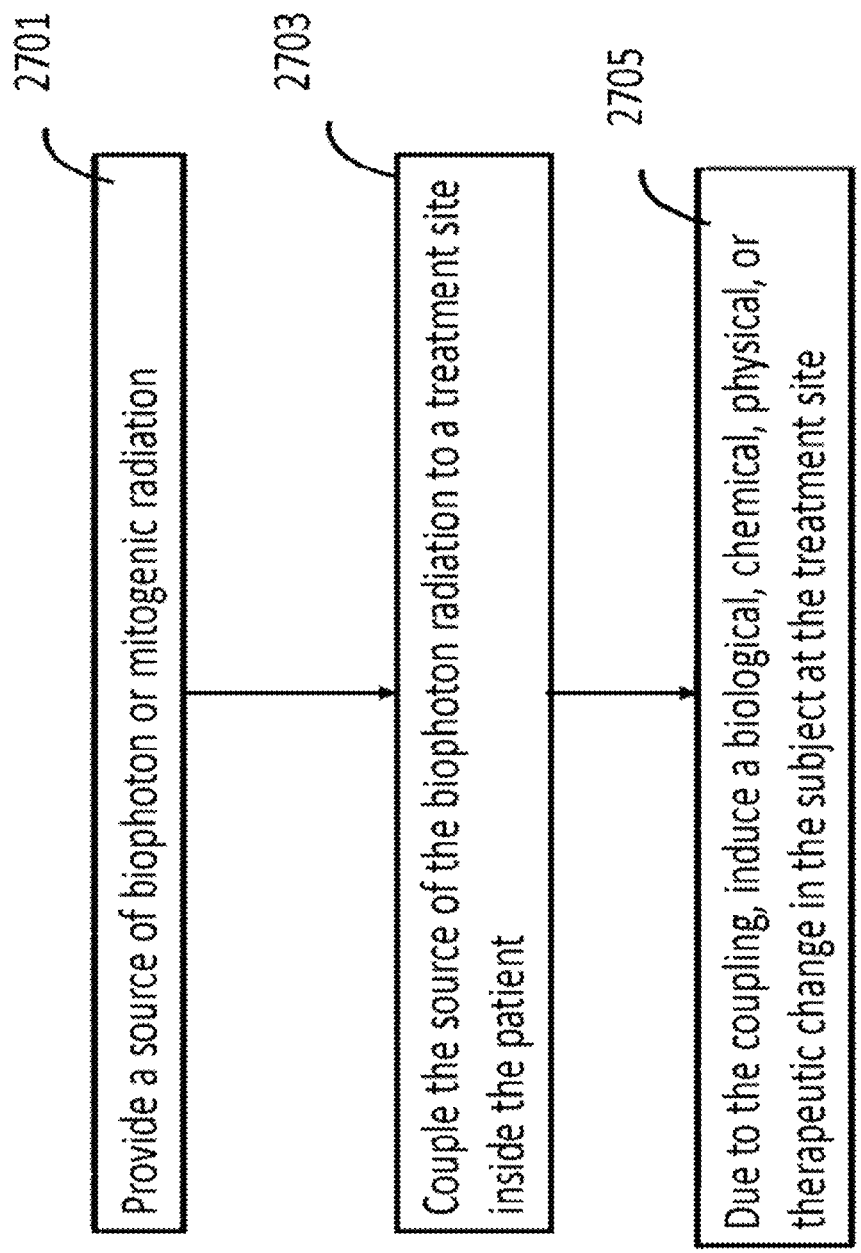

METHODS, DEVICES, AND COMPOSITIONS FOR MEASURING AND INDUCING CELL-TO-CELL COMMUNICATION, AND THERAPEUTIC USES THEREOF

CROSS REFERENCE TO RELATED APPLICATIONS

This application is related to and claims priority from U.S. Provisional Ser. No. 62/745,057, field Oct. 12, 2018, the entire contents of which are hereby incorporated herein by reference. This application is related to each of U.S. Ser. No. 15/874,426, filed Jan. 18, 2018; U.S. Ser. No. 15/649,956, filed Jul. 14, 2017, now U.S. Pat. No. 9,993,661; U.S. Ser. No. 14/131,564, filed Jul. 11, 2014, now U.S. Pat. No. 9,907,976; PCT application PCT/US12/045930, filed Jul. 9, 2012; U.S. Provisional Ser. No. 61/505,849 filed Jul. 8, 2011; U.S. Ser. No. 15/151,642, filed May 11, 2016; U.S. Ser. No. 12/417,779, filed Apr. 3, 2009; U.S. Provisional Ser. No. 61/042,561, filed Apr. 4, 2008; U.S. Provisional Ser. No. 60/954,263, filed Aug. 6, 2007; U.S. Provisional Ser. No. 61/030,437, filed Feb. 21, 2008; U.S. Ser. No. 12/059,484, filed Mar. 31, 2008; U.S. Ser. No. 11/935,655, filed Nov. 6, 2007, now U.S. Pat. No. 9,358,292; U.S. Provisional Ser. No. 61/042,561, filed Apr. 4, 2008; U.S. Provisional Ser. No. 61/035,559, filed Mar. 11, 2008; U.S. Provisional Ser. No. 61/080,140, filed Jul. 11, 2008; U.S. Ser. No. 12/401,478 filed Mar. 10, 2009, now U.S. Pat. No. 8,376,013; U.S. Ser. No. 12/059,484, filed Mar. 31, 2008; U.S. Ser. No. 12/389,946, filed Feb. 20, 2009, now U.S. Pat. No. 8,951,561; U.S. Ser. No. 12/417,779, filed Apr. 3, 2009; U.S. Provisional Ser. No. 61/161,328, filed Mar. 18, 2009; PCT application PCT/US2009/050514, filed Jul. 14, 2009; U.S. Ser. No. 12/725,108, filed Mar. 16, 2010, now U.S. Pat. No. 8,389,958; U.S. Ser. No. 12/764,184, filed Apr. 21, 2010, now U.S. Pat. No. 9,302,116; U.S. Provisional Ser. No. 61/443,019, filed Feb. 15, 2011; U.S. Ser. No. 13/732,882, filed Jan. 2, 2013, now U.S. Pat. No. 8,618,509; U.S. Ser. No. 14/688,687, filed Apr. 16, 2015, now U.S. Pat. No. 10,080,276; U.S. Ser. No. 15/307,766, filed Oct. 28, 2016; PCT application PCT/US2017/029300, filed Apr. 25, 2017; U.S. Provisional No. 62/897,677, filed Sep. 9, 2019; and U.S. Provisional No. 62/327,121, filed Apr. 25, 2016; the entire contents of each of which is incorporated herein by reference.

BACKGROUND OF THE INVENTION

Field of Invention

The invention pertains to ways to induce a biological change in a medium not necessarily directly treated with an agent which can cause the biological change.

Discussion of the Background

Light modulation from a deeply penetrating radiation like X-ray to a photo-catalytic radiation like UV or IR, opens the possibility for activating bio-therapeutic agents of various kinds within mammalian bodies. Other possibilities include the activation of photo-catalysts in mediums for cross-linking reactions in polymeric chains and polymer based adhesives. These examples are but two examples of a number of possibilities that can be more generally described as the use of a conversion material to convert an initiating radiation that is deeply penetrating to another useful radiation possessing the capability of promoting photo-based chemical reactions. The photo-chemistry is driven inside media of far ranging types including organic, inorganic or composited from organic and inorganic materials.

Photo-activation with no line of site required can be done in-vivo and ex-vivo such as those carried out in cell cultures. In turn, the photo activation of a select bio-therapeutic agent, and conceivably more than one agent at a time, can lead to the onset of a desirable chemical reaction, or a cascade of reactions, that in turn lead to a beneficial therapeutic outcome. As an example, the binding of psoralen compounds to DNA through the formation of monoadducts and/or cross-linked adducts is well known to engender an immune response if done properly.

As background as to the physical and biological structures that the present invention can address, below is a summary of the various anatomical cell structures present in subjects to which the techniques of the present invention disclosed below can apply. Further details of anatomical structures can be found in U.S. Pat. No. 9,295,835 (the entire contents of which are incorporated herein by reference).

As described in the '835 patent, humans and animals are constructed of cells. Cells are the smallest fundamental unit of life. A cell is considered to be the smallest living structure capable of performing all of the processes that define life. The human body is made up of some 100 trillion cells representing perhaps some 300 cell-types. Each cell-type performs a specific function such as operating muscles, glands, and vital organs. In addition, nerves, which are made of communicating-cells called neurons, provide electrical regulating signals to operate and adjust enormous amounts of functional activities throughout the body to maintain homeostasis (life equilibrium).

FIG. 1 is a schematic illustrating various cellular components of an example cell 100. The depiction shown in FIG. 1 illustrates, for example, cellular components such as mitochondria, ribosomes, centrosome, centrioles, the nucleus, and so on.

FIG. 2 illustrates a schematic drawing of the structure of a plasma membrane 100 of the cell 100 shown in FIG. 1.

Cells are known to have a complex cellular wall referred to in the art as a plasma membrane, an example of which is shown in FIG. 2. A portion 200 of the plasma membrane is shown in FIG. 2 with respect to the cell 100. The plasma membrane separates the internal structures and operating organelles from the cell's external environment. It houses and protects the contents of the cell. It is made of a bi-layer of phospholipids and various proteins, which are attached or embedded.

The plasma membrane is a semi permeable structure that allows passage of nutrients, ions, water, and other materials into the cell. It also allows an exit pathway for waste products and for functional two-way passage of many kinds of molecules to adjust cell chemistry. The principal purpose of the cell membrane is to provide a barrier that contains all of the processes and components within the living cell and to simultaneously repel unwanted substances from invading or entering the cell.

There are some 300 types of ion pores in a plasma membrane for purposes of transporting the raw materials used by the cell to live and to perform its duties.

The plasma membrane may have from a relatively small number of ion channels up to approximately 200 to 400 molecular channels or more and of different dimension through which the passage of nutriments and electrolytic ions can enter the cell. The thickness of a plasma membrane is estimated to be about 7-8 nanometers. In addition, selected ion channels can rid the individual cells of waste products in a process called autophagy to transport, excrete or see to the expulsion of waste products from the cellular interior into the extracellular space.

The molecular channels within the plasma membrane have molecular sized openings for the different molecules of extracellular ions and other nutriments or materials required by the cell. An example of the materials desired by the cell to transport through these channels include, but is not limited to, sodium, potassium, magnesium, calcium ions, and water. The openings are provided for example by specifically sized pores through which ions can travel between extracellular space and cell interior. The channels are typically specific (selective) for one ion; for example, most potassium channels are characterized by 1000:1 selectivity ratio for potassium over sodium, though potassium and sodium ions have the same charge and differ only slightly in their radius. The channel pores are typically so small that ions must pass through in a single-file order.

A channel may have several different states (corresponding to different conformations of a protein), with each state considered to be either open or closed. In general, closed states correspond either to a contraction of the pore—making it impassable to the ion—or to a separate part of the protein, stoppering the pore. For example, the voltage-dependent sodium channel undergoes inactivation, in which a portion of the protein swings into the pore, sealing it. This inactivation shuts off the sodium current.

Ion channels can also be classified by how the channels respond to their environment. For example, the ion channels involved in an action potential are voltage-sensitive channels; they open and close in response to the voltage across the membrane. Ligand-gated channels form another important class; these ion channels open and close in response to the binding of a ligand molecule, such as a neurotransmitter. Other ion channels open and close with mechanical forces. Still other ion channels—such as those of sensory neurons—open and close in response to other stimuli, such as light, temperature or pressure. Light (an electromagnetic radiation) was therefore demonstrated to enable the triggering of certain cellular functions.

The passage of ions through the cellular membrane participates, generates, and/or creates a flow of electric currents within the membrane and/or on the inner surface of the plasma membrane. At points where the cytoskeleton, intermediate-filaments or microfilaments are attached to the plasma membranes, those points allow "signals" to gain entry onto the cytoskeleton so as to be able to serve as a pathway to transport the signals around the cell. Such signals may travel to trigger or adjust chemical reaction areas and to various organelles and the nucleus to trigger reactions and pass along cellular communication instructions, at a minimum. Cells were therefore demonstrated to be equipped with an enabling infrastructure to sense and react to stimuli including electrical and electromagnetic stimuli.

Since cells are electrochemical in nature, the plasma membrane is the site for generating the cells electrical signals for metabolic and other operations and to serve as a means to communicate, relay and receive signals with other cells, especially those of similar type. The nucleus and plasma membrane communicate with electrical signals. The nucleus determines how the cell functions and also determines the architecture of the cell and its contents. The plasma membrane uses electrical signaling to open passageways and ion channels to allow the intake of chemicals as well as the outflow of cellular waste products. The electric signaling exists by virtue of potential gradients and the establishment of currents that exist within cells and between cells within biological bodies. The displacement of charged species encompasses electrons, ions, anions, low, mid and high molecular weight biological polymers, which in turn includes, but is not limited to, proteins. It is well known that the displacement of charged species (current) is almost always accompanied by the establishment of magnetic fields during the transient states associated with motion.

The outside of the cell membrane is coated with a defensive glycocalyx, which is designed and produced by the cell to protect it and allow it to be recognized. The nucleus has input into the crafting of membrane defensive characteristics. The glycocalyx can produce a negative electric surface charge in cancer cells so as to repel the body's immune system.

The cell membrane regulates the flow of materials into and out of the cell. Also, it can detect external signals and mediate interactions between other cells. Membrane carbohydrates installed on the outer surface function as cell markers to distinguish itself from other cells.

This plasma membrane contains the sites where the electrical energy is created and the cellular communication signals are formed. These signals are transmitted over the cytoskeleton, which acts like wires, to regulate and trigger metabolic and functional processes within the cell. The cell nucleus communicates with all organelles and operating structures located within the cell. FIG. 3, for example, illustrates a junction view 300 of the attachments between tumor cells.

FIG. 4 illustrates a pictorial drawing of the internal framework 400 of a cell, such as the cell 100 shown in FIG. 1.

The cytoskeleton in a cell maintains the shape of all cells from the inside. It is like a geodesic structure that provides strength and internal areas for electro-chemical timed reactions. Noteworthy is that the cytoskeleton extends into other cells and links up with their cytoskeleton to maintain and form communication links into adjacent cells. This structure is made up of a network of hollow-microtubules, solid-microfilaments, and solid-intermediate filaments. The cytoskeleton is anchored to the plasma membrane and serves as the 'wiring' to transmit the cellular communication signals. The cellular environment is highly networked and the transmission of chemical and electrical information is made more efficient as a result if this interconnectivity.

The cytoskeleton is made up of actin and myosin, which are also found in muscle structures. The cytoskeleton also controls the circulation of the cytosol, which is the fluid and semi-fluid that suspends the organelles. Organelles are the functioning entities of the cell that manufacture and distribute cellular products and processes necessary for the cell to live.

The cytoplasm in a cell is a fluid, that can be rather gel-like, which surrounds the nucleus, which is considered an organelle. The nucleus contains the DNA genetic information and hence, controls both the activity of the cell and its structural nature. The nucleus is spherical and is surrounded by a double membrane, the nuclear membrane and envelope, which is perforated by a significant number of pores that allow the exchange of materials and substances with the cell's cytoplasm and the extra moist environment outside which contains the ionic minerals and chemicals that feed the cells and provides the necessary water.

The nucleus in the cell is an electrical body which contains the cell's DNA and carries programs to operate its electrical signals and the opening and closing of channels in the wall of the cell's plasma membrane. The nucleus also contains the apoptosis program for cell suicide. Depending on the duties of the cell, some use ion channels that function electrically and others are influenced by chemicals that it obtains from the extra cellular media. Ion pumps and ion channels are electrically equivalent to a set of batteries and resistors inserted in the membrane wall, and thus create voltage differences between the inner and outer sides of the membrane. Such differences in the electrical values range from −40 mV to −80 mV. Because the cell acts as a battery, it provides the power to operate molecular devices that are embedded in the plasma membrane. As described in the '835 patent, the electrical activity sends signals that communicate with adjoining cells of the tumor to regulate the cancer as an intra grail living body.

An important organelle in the cell is the mitochondrion, which serves as the power station for the cell. Mitochondria are rod or oval shaped structures functioning as respiration for the cell. A number of mitochondria are distributed within the cytoplasm and move in accordance with its flow. The product produced as a biological fuel is called adenosine triphosphate (ATP). The manufacture of ATP results from the processing of proteins, fats, and carbohydrates through the Krebs cycle. The ATP once produced is distributed to other organelles that require this bio-fuel to provide processing energy as needed.

The mechanism of energy production is known as oxidative phosphorylation. The membrane of the live biological cell and the membrane of the mitochondria are analogous to plate-like condensers with defined capacitance related to the surface area, the permittivity of the biological media and is inversely proportional to the distance between the surfaces. The pumping of ions into the intermembrane space leads to a voltage build up and the process is analogous to a metabolic pump with a defined voltage gradient and hence a power supply to drive an electromotive force.

The endoplasmic reticulum (ER) in a cell is a network of membranes that form channels that crisscross the cytoplasm utilizing its tubular and vesicular structures to manufacture various molecules. The network of membranes is dotted with small granular structures called ribosomes for the synthesis of proteins. Ribosomes are tiny spherical organelles distributed around the cell in large numbers to synthesize cell proteins. They also create amino acid chains for protein manufacture. Ribosomes are created within the nucleoli at the level of the nucleolus and then released into the cytoplasm.

Smooth ER makes fat compounds and deactivates certain chemicals like alcohol or detected undesirable chemicals such as pesticides. Rough ER makes and modifies proteins and stores them until notified by the cell communication system to send them to organelles that require the substances. Cells in humans, except erythrocytes (red blood cells), are equipped with endoplasmic reticulum.

The Golgi apparatus is made of Golgi bodies, which are located close to the nucleus and are made of flattened membranes stacked atop one another like a stack of plates. The Golgi apparatus sorts and modifies proteins and fats made by the ER, after which it surrounds and packs them in a membranous vesicle so they can be moved around the cell as needed. Similarly, there is a process to pack up cell waste products for expulsion from the cell via ports in the plasma membrane into the extra cellular spaces.

Lysosomes are the digestive system for the cell. They contain copious quantities of acids, enzymes, and phosphates to break down microbes and other undesirable substances that have entered the cell. They also digest and recycle worn-out organelles to make new cellular structures or parts.

As described in the '835 patent, the cytoskeleton is composed and constructed of intermediate sized filaments, which actually serve as the internal structure to maintain cellular shape. The filamentous structure serves to provide a highway for electrical signals to travel to sites of chemical process that reside on shelves constructed by the cytoskeleton assembly within the cell. The intermediate filaments are composed of compounds that are similar to the structures of muscles, which have their own electrical properties. The electrical signals traveling through or on the cytoskeleton most likely initiate and stop the chemical reactions, as required. The electrical signals may skip and travel along the surface of the filamentous network rather than within the central framework, again on some sort of scheduled or timed basis or in response to some event or instruction. Access to all systems within the cell by nucleus operations is made possible by electrical signals residing within the individual cells.

As described in the '835 patent, cells become more electro-negative in the course of cancerization. Cancer cells seem to reconstruct the cellular membrane access ports to allow the importation of more sodium and sugars than non-cancerous cells of the same size. The electrical potential between the inner and exterior layers of the plasma membrane serve as a sort of electrical generator to supply the power to operate the individual cancer cell.

The cytoskeleton intermediate filaments are considered to be hooked together with a sort of "Velcro" at its connection points throughout the cells interior to allow some flexing of the overall cellular structure. Importantly, the intermediate filaments continue protruding through the desmosome which allows a connection to an adjoining cancer cell. This piercing of the cell wall within the desmosome is considered to one way explaining how signals are sent and received from adjoining cells. There can be several desmosome connections on different aspects of the cell wall (plasma membrane) so as to connect to cells over, under, and beside for example a given cancerous cell, so as to provide a connected network for communication. In the alternative, other types of cellular attachment for signal transduction or transmission are likely.

Normal cells reproduce by going through a cell cycle that leads to reproduction of similar cells by a process of mitosis which is where a single cell divides and then splits into two daughter cells that are exact replications of the mother cell. Normal cells are limited as to how many times they can reproduce by mitosis, which is probably no more than 70 times.

Cancer occurs in normal cells in which birth-defected distorted chromosomes and abnormal genes can lead to the formation of a defective cell which exhibits a severe disorder of mitosis (cell division). The thrust of a cancerized cell is to continuously reproduce by splitting into similar daughter cells uncontrollably for its entire life. Some species of cancer cells can reproduce continuously every 30 minutes while others can take 24 hours or longer to multiply.

Cancer cells continue to reproduce by splitting (including the nucleus) into two daughter cells which themselves split and grow into adult cancer cells and then split again, on and on continually for the life of the malignancy. This process of cell splitting, called mitosis, only produces daughter cells, which enlarges into a massive collection of cells, which is referred to as a tumor. Designated cancer cells on the outer edges of the tumor can be released and travel to other distant sites by a process called metastasis. Once this metastatic process proceeds, the cancer spreads to critical body parts and usually heralds a poor overall outcome for the patient.

Cancer cells are typically unregulated, disorganized, and engage in extremely rapid rates of mitosis. When enough cancer cells are made, they form larger tumors, which interfere with the duties and nutrition of nearby normal cells.

Cancer does its damage in complex ways that include strangling or distorting organs, blood vessels, and nerves as well as working its way into bones, brain, and muscles. Cancer cells perform no function that contributes to the homeostasis (life equilibrium) of the body in any way.

As described in the '835 patent, cancer cells have developed ways to repel or block the human body immune system by several means including erecting an electrical shield on the outer surface of the plasma membrane, which is produced by the cancer cell itself such a thin electrical shield is called the glycocalyx and generates a negative charge to oppose the animal or human immune system, which is also negatively charged. Two negative bodies repel each other, which in the case of cancer mean that the immune system cannot engage the tumor to destroy it. The body's natural immune system is not effective in attacking cancer as it does in attacking invading bacteria or viruses or even malfunctioning cells that have been injured, which are usually positively charged. Positively charged microbes or ill cells are susceptible to killer T-cell and other immune system attacks because the negatively charged immune defenses can approach its target successfully.

Additionally, there is a programmed cell death called apoptosis. Apoptosis as a biomedical term that indicates that there is a state of natural or induced reprogramming of a cell to enter a suicide mode whereby the cell dies without any inflammatory process. Thereafter, the lifeless cell is phagocytized and removed by macrophages of the immune system. Apoptosis can occur in many kinds of cells such as erythrocytes as a method to rid the body of non-performing or defective cells. In general, cancer cells are thought to not have much opportunity to have preprogrammed cell death because those cells have an immortal ability to continue to reproduce and reorganize their cellular electrochemical system in a way that suits the purpose of the cancerized cell.

Some 200 ion channels or more populate all sides of the cell plasma membrane which encompasses and shelters the interior operations of the cancer cell. Cells, including malignant ones, are considered to have an internal signaling mechanism in order for them to operate the cell and remain alive as well as participating in tumor life processes of continuous reproduction of more cancer cells.

Signaling between cells of a tumor is also believed to make it possible to know when to release adult cells so that they can metastasize to other areas and begin a new tumor colony. The metastatic cancer cells travel within the blood vessels or the lymphatic system or propel themselves across an organ, nerve, gland or muscle to seed a new tumor site. For the individual cancer cells to communicate among themselves, they seemingly have to establish links to neighboring cells. These connections between the individual adjacent cancer cells are specifically tied to one another to allow for the sharing of signals. Ordinarily, cancer cells do not communicate with normal cells and are unable to affect the healthy normal cell in any way, therefore, sparing the unaffected normal cell from any direct operational assault.

An initiating cancer cell starts out as a normal cell, but develops a chromosomal and/or a genetic chaos that drives a transformation to malignancy. Prevailing cancer theory blames mutations in important regulatory genes for disturbing the normal controls on cells that are destined to become malignant. Such theory does not give credit to the damaging changes to actual chromosomes that are seen in all cancer cells. The distorted, broken or bent chromosomes can unbalance thousands of genes and are believed to be sufficient to trigger cellular instability that can lead to serious genetic disruption, transforming so-called normal cells into malignant ones. While the cancer cells may retain their electro-chemical signaling and operating systems which existed when it was a normal cell, changes seemingly occur to rearrange its cellular mechanisms in new ways to eventually disconnect its communication ability from adjacent normal cells and to start rapid reproduction of more cancerous cells.

As described in the '835 patent, the first cancer cells that are adjacent to normal unaffected cells are sometimes not "wired" into the rest of the tumor. Perhaps these first cells are only a demarcation line from malignant to normal and do not have to participate in the cellular communication system. Later cells do develop the desmosome interconnection communication system that allows a way for each cell to speak to its adjacent neighbor cells. Other means of communicating between cancer cells beside desmosomes are gap junctions, direct cell connections, and tight junctions. The various junctions are connected with the intermediate filaments so as to provide the pathway to transmit messages between the various cancer cells.

It is believed that neither the normal cell nor the malignant cell can live without a functioning electrical signaling mechanism to operate the electro-chemical processes that are shelved on the cytoskeleton shelving. The cytoskeleton is the framework within the cell that provides a somewhat flexible geodesic-like framework to maintain cell shape, provide shelves for chemical or electrochemical process, and allow space for the organelles, nucleus, and protein manufacturing elements within the cell. The liquid within the cell is called cytoplasm. There is a cytoplasmic streaming process that causes directional movement of the liquid cytoplasm as a means of local transport for the semi-floating organelles (functional cell components). Likely this allows these floating structures some sort of communication between the cellular membrane and the nucleus as they come into close proximity.

As described in the '835 patent, individual cells operate themselves by electrical and chemical processes to maintain life and to perform the function for which a given cell has been constructed. Cancer cells are considered to have different electrical signals than normal cells.

Cells generate their electrical energy and communication signals within the plasma membrane. The plasma membrane may also have electrical connections to adjacent cells of the same type. The nucleus is considered in communication with activities occurring in the plasma membrane, for that matter all other activities of the cell.

Cell signaling may be accomplished by a combination of electrical and chemical interactions. Different types of cells should require a varied level of signaling qualities. The creation or generation of a given cell signal is believed to begin in the plasma membrane where raw material and chemical ions are taken in from the extracellular matrix to both generate electricity and establish the signal format. The plasma membrane is a sort-of cell wall that takes in the required raw material via its ion channels. Ion channels open and close to allow passage into and from the cell interior. Electrical signals are likely generated in the plasma membrane before they are sent via the cytoskeleton, all about the cell to go and participate and contribute to cell operations.

The cytoskeleton also serves as a geodesic-style dome providing a framework to shape and support the cell. In addition, the cytoskeleton serves as the pathway by which cell signals generated in their plasma membrane travel within and around the cell to do its work. In addition, communication to adjacent cancer cells could happen through connections such as desmosomes, which are extensions that bridge and allow communication between adjacent cells of a tumor.

Necrosis, apoptosis, autophagy, stasis, macroautophagy, cell starvation, tumor reduction, shut-down of mitochondria production of ATP, consuming contents of cytoplasm, incipient starvation, blebbing, cell shrinkage, nuclear fragmentation, chromatin condensation, chromosomal DNA fragmentation, pyknosis, karyolysis, karyorrhexis. Human bodies have complex daily cellular maintenance duties to dispose of some 50 million worn out cells every day. Average adult humans operate an ever-busy apoptosis and repair system. Key elements are briefed below.

Necrosis is a form of traumatic cell death that results from acute cellular injury. Necrosis death of cells can happen because of infection or fever that result in the premature death of cells in living tissue. Untreated necrosis results in a buildup of dead and decomposing cell debris in the region of actual cell death. A classic example would be gangrene. Cells dying from necrosis don't follow the usual apoptosis transduction pathways.

Apoptosis is the original programmed cell death technology that helps repair and model the body beginning with birth and continuing on throughout life. Some 50 billion cells die every day due to apoptosis. For example, the lining of the digestive tract from the stomach lining on to the colon undergoes apoptosis every 3 to 5 days to replace the entire inner lining of the digestive tubular structures. Red blood cells are programmed to replace themselves every 90 days by undergoing killing by the spleen and the bone marrow manufacturing new blood cells and releasing them back into the blood vessels to do their work of carrying oxygen and carbon dioxide.

Technical events that appear during an apoptosis event include characteristic changes that include cell shrinkage, generating heat, hypoxic events and an increase in calcium concentration which causes snappy signaling in the nucleus that triggers and orchestrates the imminent apoptotic event.

Autophagy is from the Greek definition as "self-eating." Inside a living cell's cytoplasm are organelles identified as autophagosomes which move around the cell to sweep up viruses, bacteria, and worn out materials from the cell itself. The autophagosomes bag up or concentrates the cell sludge and worn out protein and other debris to be handled by recycling organelles that float in the cytoplasm. Some of the unusable waste is forced out of designated cell ion ports by pumping it through the plasma membrane into the extracellular fluid surrounding the cells. Since some neurons live as long as the body they have to use autophagy to maintain the quality of the overall cell health. Autophagy and mitochondrion can work together to cause apoptosis to trigger programmed cell death to rid the cell of unwanted cell component that can't be rehabilitated. Unlike necrosis, apoptosis produces cell fragments called apoptotic bodies that phagocytic cells are able to engulf, eat, digest, and then dispose of in league with the autophagy process in a well-established method to keep the overall cellular system in order.

Pyknosis is the irreversible concentration of chromatin in the nucleus of a cell involved in necrosis or apoptosis. This is followed by condensing its nucleus before expelling it to become a reticulocyte. The maturing neutrophil will be involved in forming blebs that stay in the cell until the end of its life. Blebs are distortion of the nucleus and the cancer cell shape. It is the formation of protrusion or pimple structures of what was previously a symmetrical nucleus and overall cell shape. It is followed by fragmentation of the changing nucleus on its way to experiencing karyorrhexis. During bleb formation of the nucleus, a sort of pimple formation gives the nucleus an unhealthy appearance, which does not improve.

Karyorrhexis is the ultimate bursting of the cellular nucleus into multiple pieces that cannot be repaired. The nucleus of a cell represents and is equivalent to the brain of any creature, once it is broken into pieces it is finished.

Karyorrhexis is an important cancer killing skill, which is accomplished by fragmentation of the cancer cell nucleus into apoptotic bodies, which are then engulfed and ingested by phagocyte(s). A phagocyte is a special cell that locates and surrounds broken cellular components and then eats them. There are fixed phagocytes that live in the liver, bone marrow, and spleen. Such phagocytes are represented by neutrophils and macrophages. Also, there are freely moving phagocytes such as leukocytes (white blood cells) that circulate in the blood stream to do their clean-up work. The job of the nucleus is to control all cellular operations and to participate in communication and coordination with nearby cells. If a nucleus is fragmented, it is like fragmenting the brain of a human or animal, life cannot go on with such as injury.

Electrical signaling can function to control and regulate chemical activities, autophagy, regulates the mitochondrial production of ATP which serves as an energy source for the cell, and controls the ribosome's protein manufacturing operations. In addition, the electrical codes can serve as communication means with the adjoining cells including when to release cells for metastasis operations among other duties.

Electrical signal flow traveling throughout the many cells of the tumor may allow for the generation of instructions to select cells that are destined to metastasize to distant sites to spread colonies for the malignancy. Such cells become soft and slightly puffy as they are released into the lymph or blood circulation system to travel to distant sites to start a new metastatic colony.

Electrical signals from the plasma membrane may travel on the surface of the intermediate filaments and reach chemical processes and likely ignite or stimulate a reaction that contributes to reproduction, protein manufacture or metabolic operations. Without electrical activity and the molecular devices that operate the cell plasma membrane, the cell could not function properly.

The charge of the outer wall takes on a protective negative charge, especially on the very thin outermost cell coating which is called the glycocalyx. This glycocalyx in cancers is considered to have a continuous negative charge protecting the malignant structure from the immune system which is also electrically charged in a negative format to repel the immune system from attacking the cancer, while non-cancerous glycocalyx coatings are positive in their protective electrical charge. All of this allows the positive protective charge to permit the negative charged immune system to embrace the positive cell protective elements and engage undesirable invaders like viruses or bacteria. Not so for the cancer glycocalyx with its negative shield which may repel the immune killer T-cells as they approach.

Many issues go wrong during the formation of tumorous mass including and not limited to uncontrolled proliferation, loss of apoptosis, tissue invasion and metastasis and Angiogenesis. Though the fundamental mechanisms are still unclear, it is safe to assume that there is information (regardless of its nature) that is originated from a group of cells, an individual cell or a sub-cellular component, this information is transmitted through some means (the transmission line) and then received by a group of cells, an individual cell or a sub-cellular components that have the ability to act on the received information. It is also safe to assume that the interruption of the information from one originator to the receptor would result in information loss and therefore interruption of the communication. The information during Cancer proliferation is more often than not viewed as chemical, genetic but not electro-magnetic. In addition to the chemical and genetic information carrier entities it has been demonstrated that electromagnetic transmission is taking place. The decoding of such information is yet to be achieved. Suffice it to say that all the fundamentals of electro-magnetic communication have been established. It is therefore useful to add the possibility of electromagnetic transmission to the existing understanding of the dynamics fueling cancer.

The membrane of biological cells and organelles act like platelike capacitors with the capacitance:

$$C = \frac{\chi \varepsilon \varepsilon_0 \rho 2}{d}$$

Where $\chi$ is the portion of the plate-like capacitor, $\varepsilon$ and $\varepsilon_0$ are the permittivity of the biological media and the permittivity of free space, d the distance or space in the intermembrane and $\rho$ is the radius of curvature of the platelet. The energy stored is related to the established voltage gradient divided by the distance.

The helical coils of bio-molecules result in an inductance represented by the equation:

$$L = \mu \mu_0 d/8\pi$$

Where $\mu$ is the Permeability of the biological media.

Lastly the dynamic circuitry of highly nonlinear biological interconnections which contributes to charge storage as well as resistance between the various molecules as gated by hoping of electrons or conductance of heavier charged species (ions, anions, low molecular weight species) leads to an impedance described by $$Z = (R^2 + (\omega L - 1/\omega C))^{1/2}$$

The impedance Z is the smallest when Z=R where $\omega L = 1/\omega C$. Under this condition and a constant electric field (as established in the metabolic pump and as exemplified by the mitochondria ions build up in the interlayer, which therefore represents a power supply condition with a well-established voltage gradient, a variety of oscillatory conditions can be established. These oscillatory conditions do take into account the inter-connectivity of the biological media with many constituents each sharing boundary conditions and contributing to an overall energy continuum of the collective. These biological oscillatory systems are complex, and many fundamental electromagnetic laws and thermodynamic principles need to be applied, simulated, verified gaged for their predictive effectiveness. This aside, the establishment of conditions intrinsic to the biological system leading to the charge up and storage of electrical energy and subsequently discharge and decay of the stored energy under the form of electro-magnetic energy is empirically well established.

FIG. 4A-1 is a depiction of on the left a) a conventional LRC circuit capable of resonating and releasing stored energy E in the electromagnetic energy emission at well defined frequencies and on the right (b) an equivalent type biological circuit with a metabolic pump (MP), coiled molecules (CM) with a representative inductance (L), a capacitive layer (CL) from a phospho-lipid bi-layer, and the highly interconnected biological media (BM) completing the electrical circuit. This biological circuit exhibits similar characteristics as a low energy storage (low Q) LRC and can resonate in the range of $10^{14}$-$10^{15}$ Hz range which encompasses the visible and the UV range. Low Q typically translates into a broad emission frequencies.

Furthermore, taking values of $\mu$, $\varepsilon$ and $\chi$ that pertain to biological media, one can calculate the frequency of the resonance oscillators. These calculations yield frequencies in the range of $10^{14}$-$10^{15}$ Hz range which encompasses the visible and the UV range. These findings were the subject of publications including:

Chwirot, W. B., Dygdala, R. S. and Chwirot, S. (1985) optical coherence of white light induced photon emission form microsporocytes of Larix and Europeas Mill. Cytobios, 44, 239-249.

Frohlich, H. and Kramer, F. (1983) Cohernet exciation in biological systems. Springer Verlag, Heidelberg.

Smith, C. W., Jafary Asl, A. H., Choy, R. Y. S. and Monro, J. A., (1987) the emission of low intensity electromagnetic radiation form multiple allergy patients and other biological systems. Photon Emission from Biological Systems, Jezowska-Trsebiatowska, B. Kochel, B. Slawinski, J. and Strek, W. (eds). World Scientific, Singapore, pp. 110-126.

Tiblury, R. N. (1992) the effect of stress factors on the spontaneous photon emission from microorganisms. Eperientia, 48, 1030-1041.

It is therefore useful, in view of the empirically well-established bio-photonic energy and the sound theoretical understanding, to view the classical cancer proliferation steps and identify the presence and the possible fit and play of the of electromagnetic energy in the various proliferation steps including cell proliferation, loss of apoptosis, tissue invasion and metastasis and angiogenesis.

Receptors consist of three domains and extracellular Ligand binding domain a transmembrane domain and an intracellular domain as illustrated in the figure:

Binding of a ligand to the extracellular domain activates the receptor tyrosine kinase which activates other proteins by phosphorylation of adding a phosphate to the amino acid tyrosine on a protein inside the cell.

The binding of the ligand to the extracellular domain could be accompanied by the emission of light in view of the Gibbs free energy reduction that accompany a favorable chemical reaction. When a ligand binds to the receptor a signal goes to the intracellular domain activating the associated enzyme and initiating a cascade of signals to the nucleus that tells the cell to grow and divide or to stop growing. These signals can in fact be electromagnetic in nature.

A protein kinase is a kinase enzyme that modifies other proteins by chemically adding phosphate groups to them (phosphorylation). Phosphorylation usually results in a functional change of the target protein (substrate) by changing enzyme activity, cellular location, or association with other proteins. The human genome contains about 560 protein kinase genes and they constitute about 2% of all human genes. Up to 30% of all human proteins may be modified by kinase activity, and kinases are known to regulate the majority of cellular pathways, especially those involved in signal transduction.

Autocrine Stimulation:

Malignant cells generate many of their own growth signals which allows them to divide with reduced external growth stimulation some cells are able to produce their own growth factors and stimulate their own growth. These growth factors are then driven or diffused to the cell membrane and release to the environment outside of the cell which stimulates certain ligand.

It is possible that the autocrine process is the results of electromagnetic radiation that results from within the cell or group of cells when under stress. The stress signal stimulates biophotons which favor the over production of certain molecules (growth factors in this case) and keeling the system off balance. For example: Glioblastomas express platelet derived growth factor or PDGF and sarcomas express tumor growth factor alpha or TGF-alpha & epidermal growth factor receptors or E-GFR. In one embodiment, the present invention can interfere with the transmission of information related to proliferation by having energy modulators that get excited by X-Ray energy and emit UV energy tuned to denature such growth factors as EGFR and PDGF described in sarcomas and glioblastomas. The growth factors are targeted by UV energy to halt the growth factor inside and outside the cell. It is conceivable to have energy modulators (of small enough size) to migrate into the cytoplasm and emit UV radiation selective to the full or partial denaturization of the growth factor.

In normal cells, the production of cell surface receptors is limited by cellular restraints on gene expression and protein translation. In tumor cells, however, mutations in the genes and coding for the receptors disrupts this finely tuned regulation and too many copies of the gene are produced in a phenomenon called gene amplification.

Excessive transcription and production of receptors leads to the fact that the more receptors expressed, the more binding sites are available for the ligands. This is a sort of runway condition. The off balance of finely tuned dynamics, results in tumor cells that have increased potential to be triggered into a growth phase by the binding of ligands to the excess receptors that decorate the cell walls.

Gross overexpression of growth factor receptors can result in ligand independent signaling where receptors are active in the absence of stimulating molecules. Structural changes to a receptor can also lead to ligand independent activation. This structural change including a modified conformation could be triggered by light, such as truncated versions of the EGRF where much of the intracellular domain is missing or constitutively active.

EGF-Receptor (such as HER1 or ErB-1) is a member of a sub family of type one receptor tyrosine kinases. These receptors are found primarily in the membranes of normal epithelial cells from: skin, breast, colon and lungs (amongst others). EGF-Receptor and its ligand play a central role in the regulation of cell proliferation differentiation & survival. EGFR is overexpressed in tumors arising from the colon, rectum and head and neck to name a few.

When a specific ligand binds to its receptor this leads to changes in the receptor that transmit a specific signal into the cell. For example the receptor tyrosine kinase is activated and initiates a signaling pathway specific to that receptor. This phenomenon is called signal transduction.

Activation of a signal transduction pathway creates a complex chain of events in the cytoplasm or fluid intracellular space that eventually leads into the cell nucleus where the transcription of genes regulating cell cycle progression are stimulated resulting in cell proliferation.

One of the major cascades implicated in cancers is the Ras Raf Activated Protein MAP kinase pathway. Another interesting pathway is the phosphor type 3 kinase or PI 3K/Akt/mTOR pathway. These pathways are linked to each other and other signal transduction pathways in the cell de-regulation or loss of normal controls in any of these pathways is thought to be present in all human tumors.

Once the signal reaches the nucleus, transcription factors are activated. These factors transcribe the genes that are translated into proteins, such as growth factors, that are necessary to allow the cell to continue to proliferate. Therapies can target factors responsible for tumor growth include the ligand receptors, intracellular second messengers and nuclear transcription factors.

Ligands can be neutralized before they bind to the receptors: An example of this is Avastin which is a humanized monoclonal antibody that targets circulating vascular endothelial growth factor or VEGF.

Platelet derived growth factor or PDGF, fibroblast growth factor or FGF, and other examples of ligands can be targeted for different cells in the body. Light based therapies can target the denaturization of these chemistries as exemplified before.

The receptors on the surface of normal and tumor cells can be inhibited directly. Erbitux is an example of this. It is a chimeric antibody that binds directly to the epidermal growth factor receptor and competitively inhibits the binding of EGF and other ligands such as TGF-alpha. Another way to block the receptors function is through small molecule inhibitors of receptor phosphorylation associated with them. For example, EGF receptors have a tyrosine kinase that can be blocked by molecules such as Gefitinib (Iressa) or Erlotinib (Tarceva).

Apoptosis:

Apoptosis is a mechanism by which organisms limit the growth and replication of cells. If apoptosis did not occur it would be hard to control growth and tissue homeostasis would be lost (in fact this is one of the key mechanisms behind cancer). The genetic alterations in the cancer cell not only lead to increased cellular proliferation and growth they also lead to loss of apoptosis (i.e., excessive cell growth and little cell death in malignant tissue). Apoptosis occurs in normal cells to allow for removal of damaged cells and maintaining a constant number of cells in regenerating tissues and is an important part of embryogenesis. In an average human adult 50 to 70 billion cells undergo apoptosis per day. Apoptosis is characterized by changes such as: cell shrinkage, mitochondrial cytochrome C release, and fragmentation of cell DNA into multiples of 180 base pairs. In the end, cells are broken into small apoptotic bodies which will be cleared through phagocytosis. Phagocytosis is a process where cells take in the cell fragments or microorganisms in membrane-bound vesicles. The vesicles fuse with lysosome containing proteases and the engulfed material is processed for recycling.

There are two pathways that can activate apoptosis:

1—The first is the death receptor or extrinsic pathway. It is triggered by activation of members of the tumor necrosis factor receptor superfamily.

2—The second is through the mitochondrial or intrinsic pathway. This is set in motion by DNA damage.

Both pathways ultimately stimulate a set of enzymes called caspases which interact with inhibitors of apoptosis proteins or IAP and a Bcl-2 family of proteins (which individually have either pro and anti-apoptotic properties).

In some malignant cells there is resistance to apoptosis due to overexpression of anti-apoptotic proteins. For example Bcl-2 is overexpressed in B-cell lymphoma as a result of the translocation of its gene. Conversely, deactivating mutations having a pro-apoptotic molecule like backs is seen in some gastrointestinal tumors and leukemias. Anticancer agents have been developed targeting anti-apoptotic molecules. For instance, short segments of DNA complementary to the RNA of Bcl-2 or antisense oligonucleotides have been designed to reduce the translation of this anti-Apoptosis protein.

Activation of transcription factors can lead to apoptotic resistance. This occurs for example when members of the nuclear factor kappa B or (NF-kB) family of transcription factors are over expressed in certain tumors which lead to increased transcription anti-Apoptotic members of the IAP and Bcl-2 families. Ubiquitin proteasome pathway regulates the expression of transcription factors and other cell cycle proteins. Certain molecules can suppress or reduce NF-kB and IAP one activation and inhibit tumor promotion. Bortezomib is a proteasome inhibitor that has shown promising results in multiple myeloma. It inhibits the proteasome which leads to increased levels of the NF-kB inhibitor and therefore less anti-apoptotic proteins.

Tissue Invasion and Metastasis:

Normal cells grow in a controlled manner that form tissues that form organs with specific functions. Malignant cells are defined by their ability to invade adjacent structures and be disseminated or metastasize. Malignant tumors can metastasize at any point. They do so by having cells break off from the main to enter the bloodstream and/or lymphatic channels and travel to other parts of the body to initiate a new tumor. Their ability to invade eventually affects the function of the normal tissue into which they are growing. Metastasis is a multi-factorial process involving complex interactions between tumor cells.

The EGFR pathway activates and modulates metastasis. When the appropriate signals enter the cell, a complex chain of events within the cytoplasm is set in motion. These events eventually lead into the cell nucleus where the transcription of gene regulating cell cycle progression and cell growth are stimulated. One protein produced through the cell activation process is the enzyme matrix metalloproteinase or MMP. When a tumor cell metastasizes, it breaks off from the main tumor and enters the extracellular space. Tumor cells secrete MMP which degrade the collagenous extracellular matrix, or ECM, breaking through the basement membrane that surrounds the tumor allowing the tumor cells to migrate toward the blood or lymph vessels.

When the MMPs reach the vessel they break down the basement membrane surrounding the vessel through enzymatic action opening access to the epithelial cells lining the vessel. Tumor cells can then migrate into the blood and lymph by entering through the tight junctions of the epithelial cells. The tumor cells are then transported through the blood and lymph to other tissues. It is known that metastatic tumor cells tend to target some organs more than others although the reason why is poorly understood. The migration of tumor cells into the organs is very much like the recruitment of white blood cells to tissues after injury.

Initially there is weak adhesion of tumor cells to endothelial cells which allows the tumor cells to shelter along the vessel lining until stronger bonds are formed. Once the metastatic cells are securely attached to the endothelial lining, they leave the vessel and enter the tissue. They also leave an open pathway that allows less aggressive tumor cells to invade the tissue and grow.

Angiogenesis:

As the tumor grows it will eventually reach a size where it will need to have additional vasculature to sustain continued growth. To achieve this the tumor cells excrete certain proteins to stimulate blood vessel growth into and around the tumor in a process called angiogenesis. One of the major pathways involved in angiogenesis involves vascular endothelial growth factor, or VGEF, and its family of receptors. There are seven subtypes of VEGF and three receptors that each bind differently. VGEF affects the endothelial cells that line the blood vessels in a number of ways. It can cause them to proliferate by activating the extracellular kinases and MAP kinase signal transduction pathways. It can induce proteins that can break down the basement membrane to allow endothelial cells to migrate and invade these proteins including matrix metalloproteinases or MMPs, euro kinase plasminogen activator uPA and its receptor uPAR, as well as the tissue type plasminogen activator. It makes vessels more permeable allowing molecules and fluids to leak out.

When MMP is secreted into the extracellular space it degrades the extracellular matrix to allow pro-angiogenic factors to reach the vasculature. With the extracellular matrix degraded pro-angiogenic factors including VGEF can reach receptors on the endothelial cells of blood vessels surrounding the tumor, thus stimulating the angiogenic signal in the vessel.

VGEF also helps the new endothelial cells survive by up regulating inhibitors of apoptosis. VEGF also activates the endothelial cells to express the proteins necessary to allow the new blood vessels to form. The end result is the growth of new blood vessels into the tumor. With this growth of new vessels into the tumor, additional nourishment can be delivered to the tumor. New blood vessels in the tumor thus facilitate further tumor growth. Strategies targeting VEGF and its receptors have been used successfully in clinical practice. Avastin is an antibody that binds VEGF and prevents its binding to its receptor. Another therapy is Sutint which is a small molecule inhibitor with high binding affinity for VEGF and PDGF receptors. With psoralen compounds and UV energy modulators, it is possible to achieve the same results by binding the affinity of VEGF and PDGF. Another strategy is to target the exact frequency (derived from a UV-VIS) to cause ionization or denaturization of the VEGF and PDGF.

While much is known about these various biological processes, and much is known about the phenomenon of cell-to-cell communication/signaling, methods and techniques are needed to harness the signaling power of cells to affect and/or trigger various of these biological processes within a subject.

SUMMARY OF THE INVENTION

Accordingly, one object of the present invention is to provide a method for treatment of a condition, disorder or disease in a subject which induces a change in a targeted region that is not directly exposed to an agent which can cause a biological, chemical, physical or therapeutic change. The induced change occurs in situ to treat a condition, disorder or disease.

A further object of the present invention is to provide a method for treatment of a condition, disorder or disease in a subject using transmission of signals from a first or control region into a second or target region of the subject to effect a predetermined change in the target region.

A further object of the present invention is to provide a method for treatment of a condition, disorder or disease using cell to cell communication to effect a predetermined change in the target region.

A further object of the present invention is to provide various biophoton collectors and biophoton bypasses useful for implementing a variety of the method embodiments.

These and other objects of the present invention, which will become more apparent in conjunction with the following detailed description of the preferred embodiments, either alone or in combinations thereof, have been satisfied by the discovery of a method of treating a subject comprising:

providing a first region of biological material coupled to the subject;

initiating a change in a cellular environment of the cells in the first region; and due to a change in biological or chemical activity of the cells in the first region, inducing a biological change in a second region inside the subject.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 4A-1 is a depiction of a conventional LRC circuit and an equivalent type biological circuit.

FIG. 7-1 is a schematic showing a section of waveguide 710 according to one embodiment of the present invention, having a high-k dielectric material 712, a low-k dielectric material 714 and a central metal 716.

FIG. 7-2 is a schematic showing the antenna pickup area of one embodiment of the present invention having an open concentric polarization construction 720a.

FIG. 7-3 depicts an array 730 of antennae 732 according to one embodiment of the present invention.

FIG. 7-4 depicts a cross section of the stub configuration 730 shown in FIG. 7-3 with antennae 732 interconnected together according to one embodiment of the present invention.

FIG. 7-5 is a schematic of a multi-up arrayed antenna 750 according to one embodiment of the present invention.

FIG. 7-6 is another schematic of the multi-up arrayed antenna 750 shown in FIG. 7-5 showing a top-level interconnection network 762 under the top surface of multi-up arrayed antenna 750, according to one embodiment of the present invention.

FIG. 7-7 is a further schematic of the multi-up arrayed antenna 750 shown in FIG. 7-5 showing the full interconnection network including top-level interconnection network 762 and bottom-level interconnection network 764, according to a further embodiment of the present invention.

FIG. 7-8 is a depiction of antennae that can be arrayed in different manners including a square antenna 780a, a rectangular antenna 780b, and a diamond shaped antenna 780c, according to embodiments of the present invention.

FIG. 7-9 is a depiction of a spiral-type packing antenna arrangement 790 according to one embodiment of the present invention.

FIG. 7-10 is a depiction of a window chamber according to one embodiment of the present invention.

FIG. 7-11 is a depiction of a window 795 made of a quartz wafer that has different sections that are independent of each other, according to one embodiment of the present invention.

FIG. 8 is a depiction of a hollow optic biophoton bypass 800 according to one embodiment of the present invention.

FIG. 11 is a depiction of a magnetic biophoton bypass 1100 according to one embodiment of the present invention.

FIGS. 13A and 13B are a depiction of a living-cell biophoton radiator 1300 according to one embodiment of the present invention.

FIG. 30 is a flowchart of another method for treating a subject according to a further embodiment of the present invention.

DETAILED DESCRIPTION OF THE INVENTION

Figure 1:
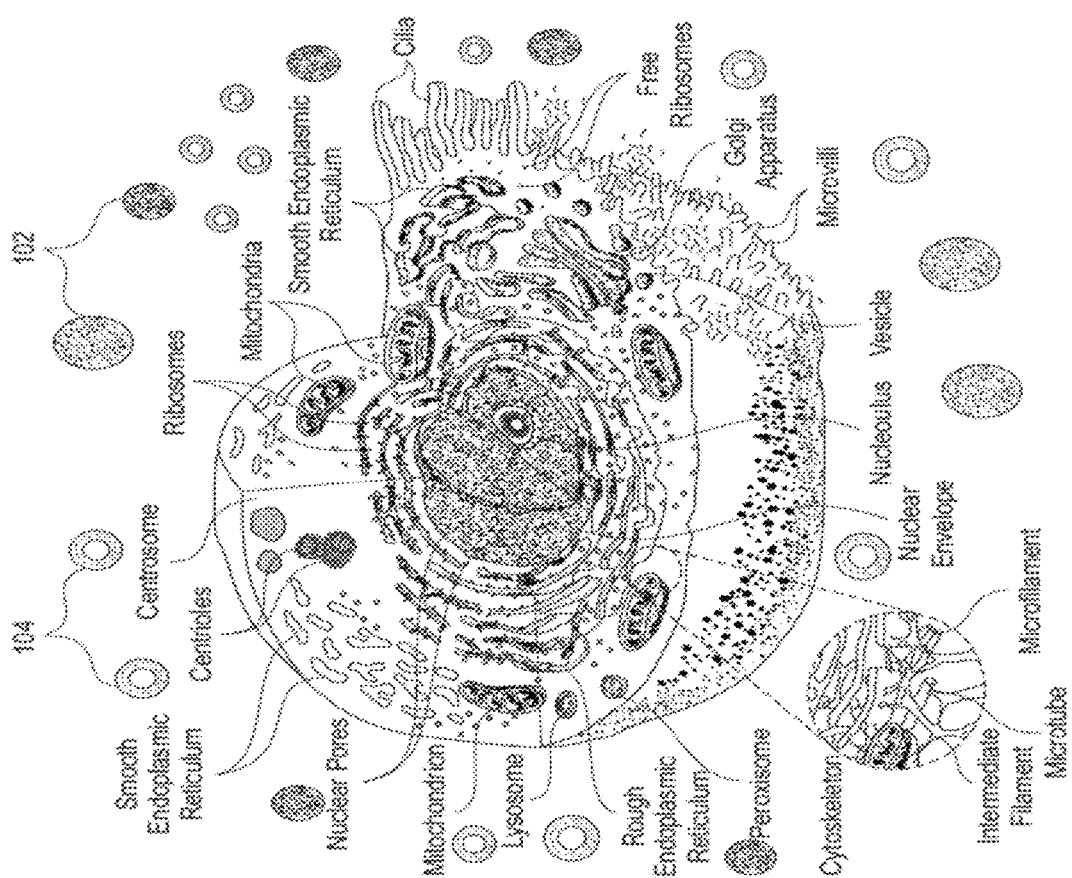
FIG. 1 is a schematic illustrating various cellular components of an example cell 100.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

While not limited to the following, the present invention with its natural sources of biophoton radiation and its artificial sources of biophoton radiation can alter the structures of the cells or the functions described above including the electrical signaling, can alter the chemical pumping and ion transport processes promoting cell growth (reproduction) or cell death, and can alter the "communication" or "coupling" between various cells to thereby provide a method for treatment of a condition, disorder or disease in a subject.

As used herein, biophoton radiation encompasses mitogenic radiation to any degree that the art considers these "radiations" or ultra weak emissions to be different. Indeed, the phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," Arch. Entwicklungsmech. Org. 100, 11-40, 1923]. His research was an attempt to answer a question not responded in its full scale even now: "what are the causes of cell division?" Combining several observations, Gurwitsch concluded that this event required a coincidence of two factors: (1) internal cell "preparedness" to division, and (2) external impulse, i.e., a signal coming from the outside and "switching on" the (already prepared) mitosis. He suggested that the external impulse was non-chemical (i.e., a kind of radiation), and induced "collective excitation" of special molecular receptors located on a cell surface. This work and more recent work has shown that an "induction length" (that is a distance from cell emitting biophoton radiation and the cell reacting to the biophoton radiation) is extremely short, on the order of mm's, with some finding an optimal distance to be 1-10 mm.

The invention in various embodiments encompasses methods and techniques for identifying bio-photonic electromagnetic energy and stimulating the production of such naturally produced and transmitted electromagnetic energy inside a cell (intracellular) and amongst a group of short ranged neighboring cells (intercellular) and finally between two distinct group of cells as in the case between a group of diseased cells inside a tumor and a group of non-diseased cells in the Tumor Micro Environment (TME). In some cases the invention relates to the stimulation or interruption of the transmission of naturally occurring bio-photonic electromagnetic energy.

In the 1970s, this area of research was investigated by a number of investigators. The presence of biological radiation from a variety of cells was later investigated by several research groups in Europe and Japan using low-noise, sensitive photon-counting detection systems [B. Ruth and F. A. Popp, "Experimentelle Untersuchungen zur ultraschwachen Photonenemission biologischer Systeme," Z. Naturforsch., A: Phys. Sci. 31c, 741-745, 1976; T. I. Quickenden and S. S. Que-Hee, "The spectral distribution of the luminescence emitted during growth of the yeast Saccharomyces cerevisiae and its relationship to mitogenetic radiation," Photochem. Photobiol. 23, 201-204, 1976; H. Inaba, Y. Shimizu, Y. Tsuji, and A. Yamagishi, "Photon counting spectral analysing system of extra-weak chemi- and bioluminescence for biochemical applications," Photochem. Photobiol. 30, 169-175, 1979]. Popp and coworkers suggested the evidence of some 'informational character' associated with the ultraweak photon emission from biological systems, often referred by Popp as "bio-photons". Other studies reported ultra-weak photon emission from various species including plant, and animals cells [H. J. Niggli, C. Scaletta, Y. Yan, F. A. Popp, and L. A. Applegate, "Ultraweak photon emission in assessing bone growth factor efficiency using fibroblastic differentiation," J. Photochem. Photobiol, B, 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," J. Photochem. Photobiol., B 18, 281-285 (1993)].

A delayed luminescence emission was also observed in biological systems [F. A. Popp and Y. Yan, "Delayed luminescence of biological systems in terms of coherent states," Phys. Lett. A 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," J. Photochem. Photobiol., B, 32, 11-17 (1996); This delayed luminescence was used in quality control of vegetable products [A. Triglia, G. La Malfa, F. Musumeci, C. Leonardi, and A. Scordino, "Delayed luminescence as an indicator of tomato fruit quality," J. Food. Sci. 63, 512-515 (1998)] or for assessing the quality or quality changes of biological tissues [Yu Yan, Fritz-Albert Popp, Sibylle Sigrist, Daniel Schlesinger, Andreas Dolf, Zhongchen Yan, Sophie Cohen, Amodsen Chotia, "Further analysis of delayed luminescence of plants", Journal of Photochemistry and Photobiology B: Biology 78, 235-244 (2005)].

It was reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, Journal of Biomedical Optics 10(2), 024006 (2005)].

There are those that maintain that the health of the body depends on certain bioelectric vibrations that are susceptible to chemical or physical toxic factors. Fröhlich notes that there are coherent electric vibrations in the frequency range 100 GHz to 1 THz, excited in cells by metabolic processes (see Fröhlich H. Coherent electric vibrations in biological systems and the cancer problem, IEEE Transactions on Microwave Theory and Techniques, Vol. MTT-26, No. 8, Aug., 1978, pp 613-617). This idea is based on observation of the inhibition or stimulation of the growth of yeast and bacterias functions of the applied frequency, showing very stable and repetitive resonances. If such vibrational states are indeed metabolically excited, then they should be manifested in Raman spectroscopy. Actually, their existence has been demonstrated during periods of metabolic activity of lysozyme and E. coli (700 GHz to 5 THz). Emissions have also been observed at lower frequencies (150 GHz or less). These vibrations occur in the tissue of higher organisms and they have been hypothesized exercise some control on cellular growth (see also S. J. Webb et al, Nature, Vol. 218, Apr. 27, 1968, pp. 374-375; and S. J. Webb et al et al, Nature Vol. 222, Jun. 21, 1969, pp. 1199-1200). Cancerization could result from a modification of these vibrations by the invasion of foreign molecules, e.g., the presence of free electrons in the condition bands of proteins. There is some evidence for the presence of double spectral lines at 1.5 and 6 THz in breast carcinoma, which may be an indication of an interaction between normal cellular vibrations and free electrons. In such coherent frequency communication between cells, it is believed that the medium through which the communication is transmitted is the water within and around the cells (see Smith, Coherent Frequencies, Consciousness and the Laws of Life, $9^{th}$ International Conference CASYS'09 on Computing Anticipatory Systems, Liege, Belgium, Aug. 3-8, 2009).

Farhardi et al, in "Evidence for non-chemical, non-electrical intercellular signaling in intestinal epithelial cells" in Biochemistry 71 (2007) 142-148 in Science Direct (the entire contents of which are incorporated herein by reference) reported on a synchrony in which mechanically separated neighboring cells (which were not able to communicate via chemical or electrical mechanisms) nevertheless showed responses in the neighboring cells (untreated) to a treated cell undergoing apoptosis. Farhardi et al, found that "detector cells" as far as 4 cm away from the control cell (where $H_2O_2$ was added to induce cell death in an intestinal epithelial cell line) also showed cell death although not exposed to the hydrogen peroxide.

Matsuhashi et al, in "Bacillus carbibiphilis cells respond to growth-promoting physical signals from cells of homologous and heterologous bacgteris" in J. Gen. Appl. Microbiol. 42, 315-323 (1996) (the entire contents of which are incorporated herein by reference) reported that bacteria cells alone can emit signals that stimulate colony formation in neighboring cells as far away as 30 cm and even those separated by an iron plate. Matsuhashi et al concluded that sonic waves were the likely signals being propagated between cell cultures.

Attempts to measure the wavelength spectrum of biophoton radiation have reported spectra in the area from 190-250 nm in the 330-340 nm wavelength range where absorption in the natural medium would be expected, thereby limiting how far biophoton radiation would travel inside a subject. While also being weak and in the UV range, natural sources of biophoton radiation emit this radiation in short bursts of a duration of approximately $10^{-3}$ s at a frequency of 10 to 100 Hz.

Others have reported biophoton emission from skin cells with a spectra of photon emission detected from 500 to 700 nm, with primary and secondary emission peaks at 630-670 nm and 520-580 nm, respectively.

Shanei et al. in Detection of Ultraweak Photon Emission (UPE) from Cells as a Tool for Pathological Studies, 2016 published on line at www.jbpe.org (the entire contents of which are incorporated herein by reference) report that it is well-known that all living cells emit ultra-weak photon emission (UPE), which is considered due to byproducts of chemical reactions in cell metabolisms. Shanei et al. reported that it has been shown that Reactive Oxygen Species (ROS) in the cells enhances the UPE intensity. Shanei et al. reported that the magnitude of such UPE is extremely weak (i.e. a few to $10^3$ photons/(sec·$cm^2$)), and the detection of such ultra-weak signals is hardly possible via sensitive instruments like photomultiplier tube (PMT) that can detect single photons. Shanei et al. also reported on earlier work where UPE from tumor tissue was observed to be higher than UPE from normal tissue.

In the experiments conducted by Shanei et al., they used 9235B as a 51 mm (2") diameter, end window Photomultiplier (ET Enterprises Limited, United Kingdom) to measure photons emitted from HT-29 cells (a common cancer of digestive tract). Their detector had its maximum response at 350 nm with the quantum efficiency of 30% in detection range of 250 nm to 600 nm. Shanei et al. showed that the application of $H_2O_2$ to the HT-29 cells caused their death and a corresponding increase in the ultra-weak photon emission (UPE).

Figure 1A:
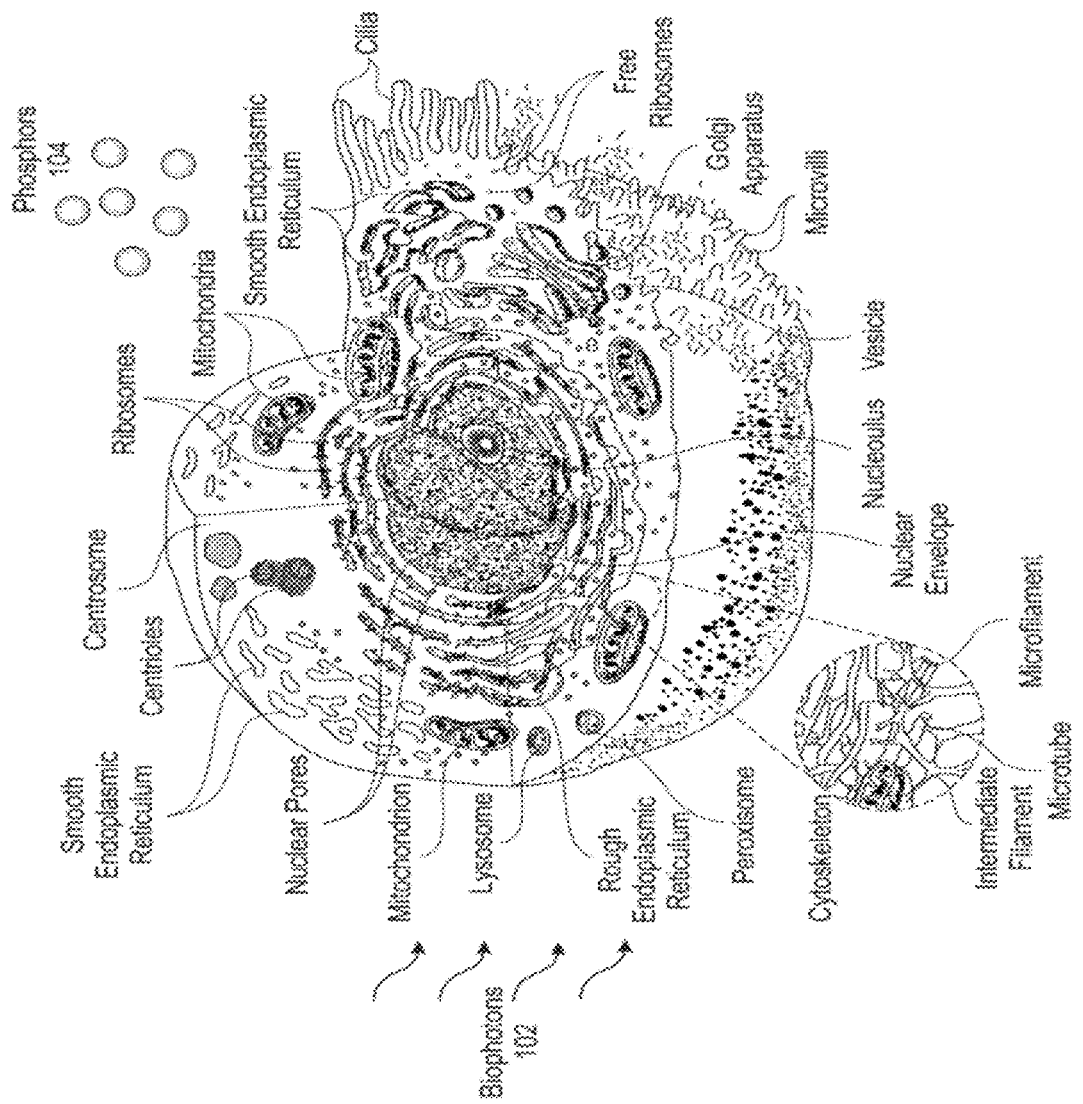
FIG. 1A is a schematic showing the cellular components of FIG. 1 along with the presence of biophotons and phosphors for emitting light to stimulate or mimic biophoton radiation.

FIG. 1A illustrates the coupling of one region (not shown) into the region shown in FIG. 1A by way of for example "natural" biophoton radiation 102 (that is radiation from nearby living cells). In one embodiment of the invention, with the coupling of these regions together, due to a change in biological or chemical activity of the cells in a first region, a biological change in a second region inside the subject will be induced.

Coupling as used herein refers to a number of ways that cells in one region induce a biological change in another region. This coupling can utilize mitogenic radiation, biophotonic radiation, electromagnetic radiation, ultraviolet radiation, visible radiation, and near infrared radiation. This coupling between different regions can be via the quantum entanglement of associated states, magnetic coupling, coupling via electric field propagation, coupling via bioplasma states, coupling via sonic waves, coupling via single-photon-type non-classical optics, coupling via coherent light emissions, coupling through tunneling nanotubes, coupling through satellite DNA, coupling through biological waveguides, coupling via a biophoton bypass, coupling via stimulation or simulation of biophotonic radiation, and combinations of any of these mechanisms described above and in more detail below. Regardless of the coupling mechanism, according to one embodiment of the invention, there is provided a method of treating a subject comprising: providing a first region of biological material coupled to the subject; initiating a change in a cellular environment of the cells in the first region; and due to a change in biological or chemical activity of the cells in the first region, inducing a biological change in a second region inside the subject.

Figure 3:
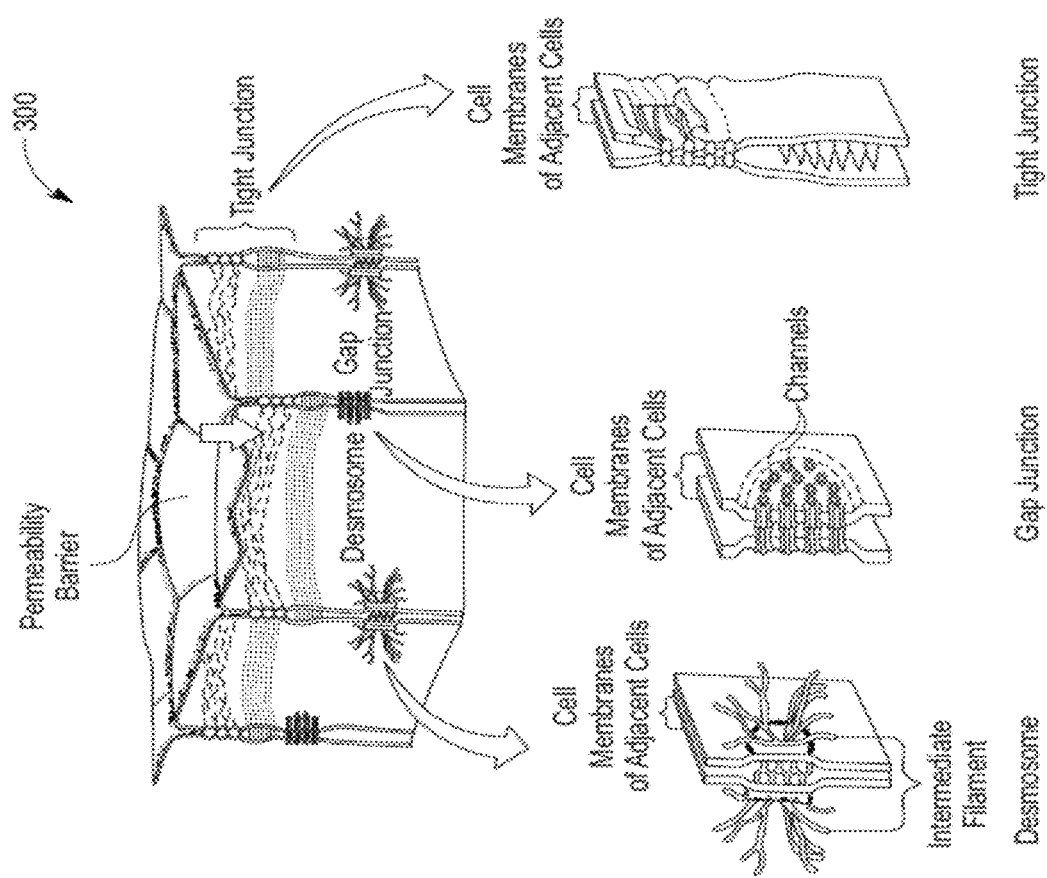
FIG. 3 illustrates a junction view 300 of the attachments between tumor cells.
Figure 3A:
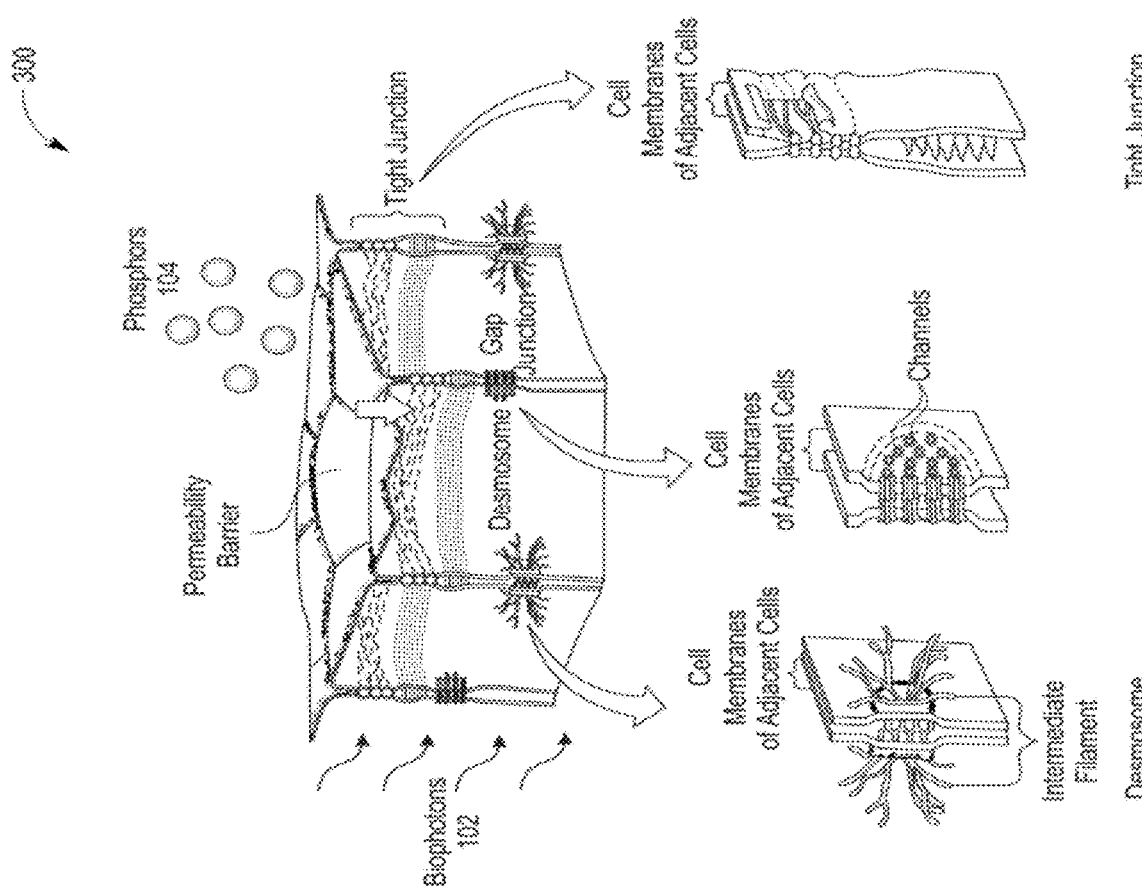
FIG. 3A is a schematic showing the junction view of FIG. 3 along with the presence of biophotons and phosphors for emitting light to stimulate or mimic biophoton radiation.
Figure 4:
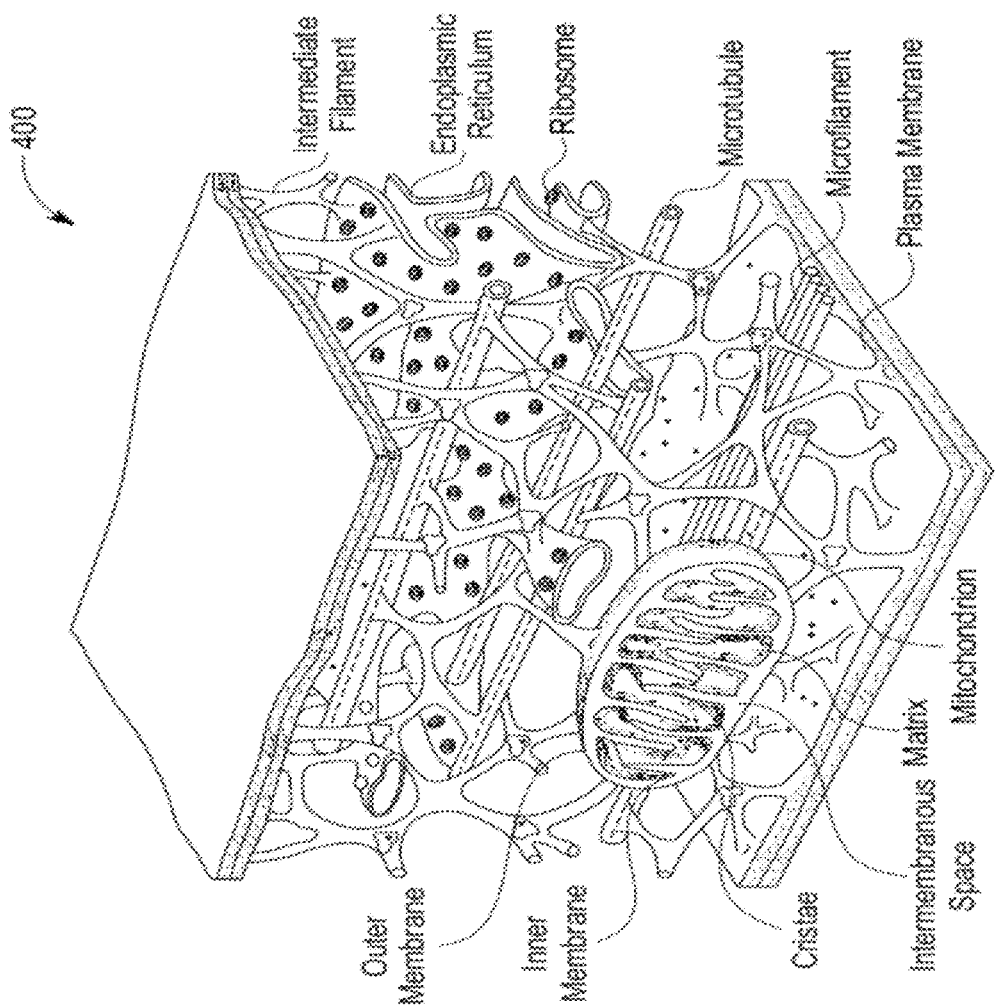
FIG. 4 illustrates a pictorial drawing of the internal framework 400 of a cell, such as the cell 100 shown in FIG. 1.
Figure 4A:
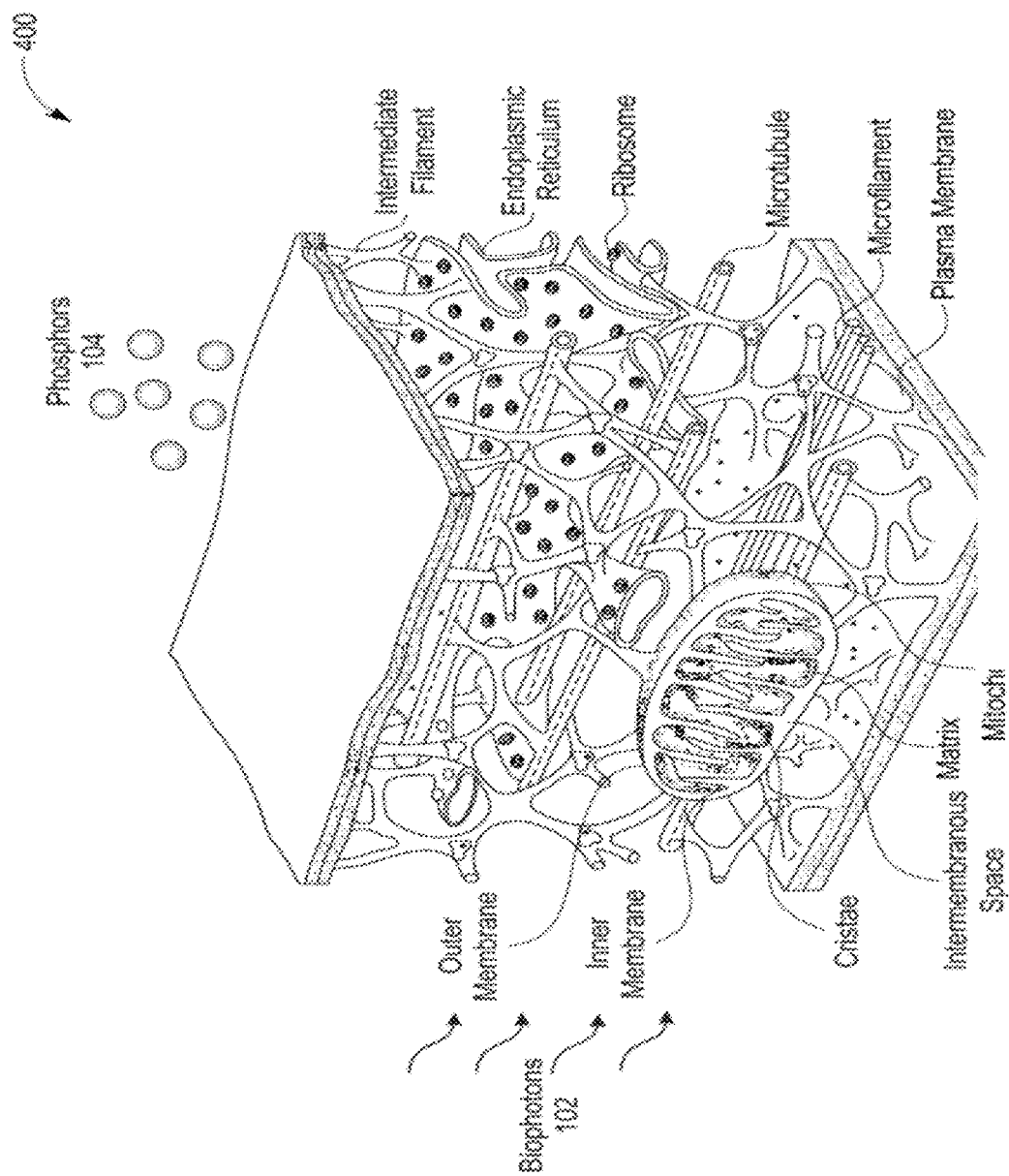
FIG. 4A is a schematic showing the internal framework of FIG. 4 along with the presence of biophotons and phosphors for emitting light to stimulate or mimic biophoton radiation.
Figures 1, 4A:
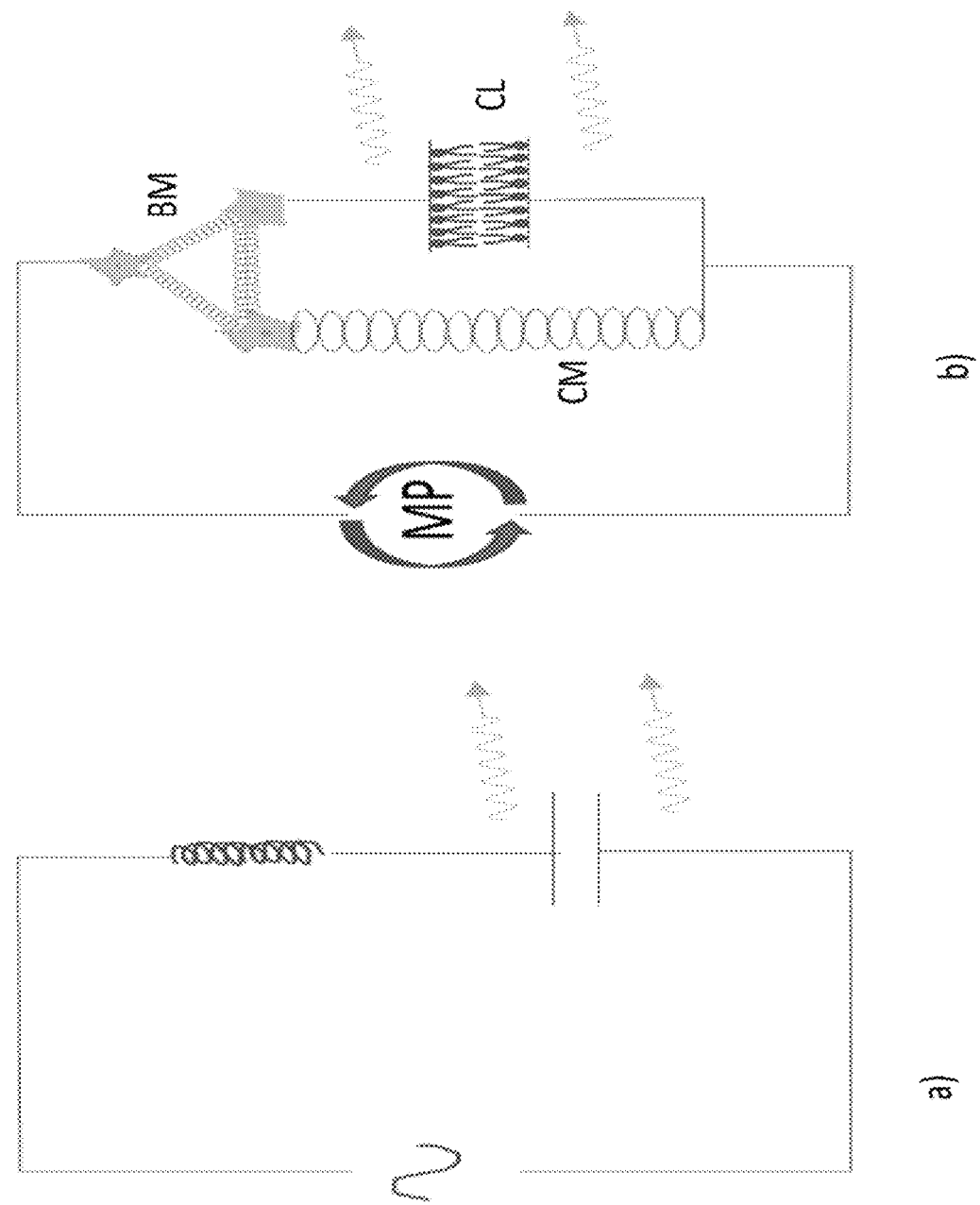

Alternatively, the phosphors 104 shown in FIGS. 1A, 3A, and 4A can mimic a "natural" biophoton radiation 102 and induce the same or similar changes that would have been induced by the natural biophoton radiation. Light emission from phosphors 104 can also be used to stimulate the "natural" biophoton radiation 102.

The Biophoton Collector

As used herein, because the exact nature of the biophoton radiation is not known and, because it may well comprise many different kinds of radiation, the radiation collector of the present invention is a collector (or a series of different kinds of collectors) that can collect radiation from various spectra ranging from ultraviolet light through visible, infrared, and far infrared bands. Furthermore, in one embodiment, the radiation collector is designed to collect electric and/or magnetic field radiation emitted from the live biological cells. Moreover, in one embodiment, the radiation collector is designed to collect acoustic or sonic waves emitted from the live biological cells and to redirect and/or amplify those collected signals to a treatment region.

Figure 5:
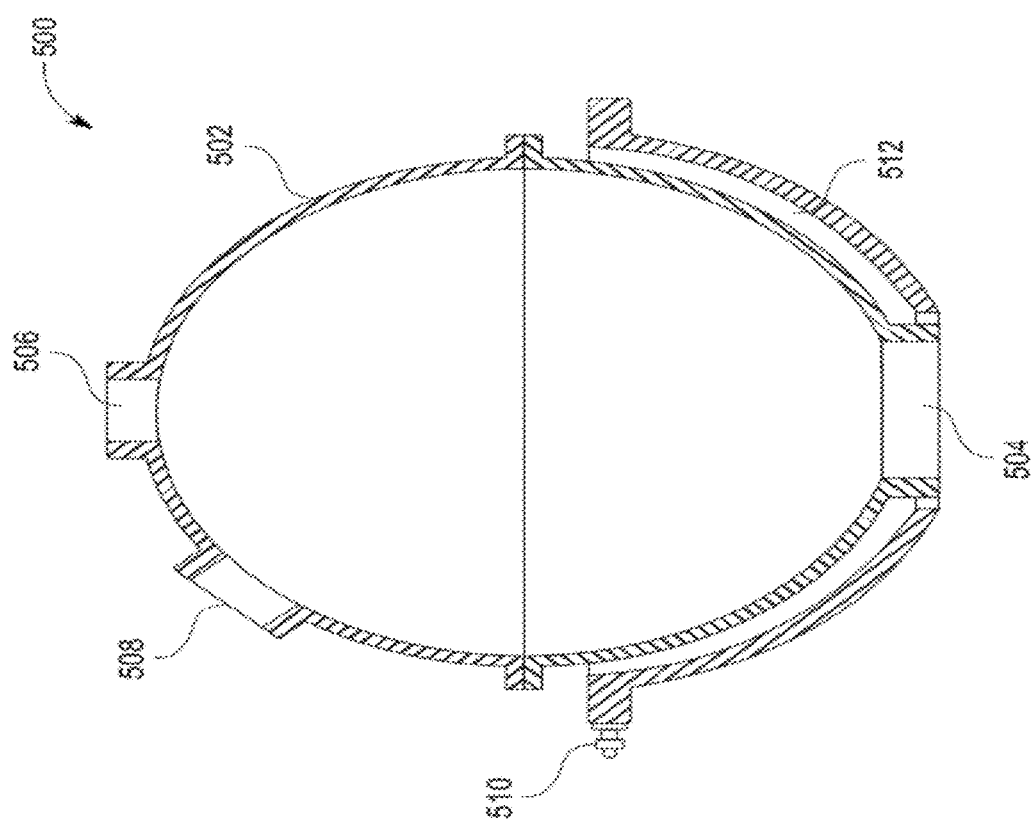
FIG. 5 is a depiction of a biophoton collector 500 according to one embodiment of the present invention.

One optical device suitable for collecting biophotons would be an integrating sphere. US Pat. Application Publ. No. 2017/019867 (the entire contents of which are incorporated herein by reference) describes an integrated sphere configuration suitable for the present invention, except that the window element in the '867 application) would be replaced by a cell holding a sample of living tissue. FIG. 5 is a depiction of a biophoton collector 500 according to one embodiment of the invention.

As shown in FIG. 5, the biophoton collector 500 includes an integrating sphere 502 with a highly reflective inner surface as described below. The biophoton collector 500 includes living cell container 504 shown in FIG. 5 at the base of the sphere 502. The biophoton collector 500 includes an output window 506 for transmitting the biophotons from the sphere 502. The biophoton collector 500 includes optionally a stimulation window 508 which can be used to expose cells in container 504 to radiation which can stimulate biophoton radiation. The biophoton collector 500 includes nozzle 510 for supply cells or nutrients or effluent to the container 504. Channel 512 can be used for supply and removal of the effluents.

In one embodiment of the invention, the biophoton collector 500 would likely be disposed outside a patient with a transmission optic (not shown) for transmission of the light from window 506 into a patient. The integrating sphere 502 would have its interior surfaces made of and/or coated with a highly reflective material. For example, the integrating sphere 502 can be formed from a hollow sphere, with an inner wall of the sphere is coated with a material coating layer (e.g., a barium sulfate layer or titanium dioxide, etc.). Biophoton light emitted from container 504 would be reflected on the interior surfaces and directed to an output window 506. In one embodiment of the invention, having a thin layer of the biological material on container 504 would avoid self-absorption effects and provide a source of biophoton radiation to be transmitted to a diseased site. In one embodiment of the invention, nozzle 502 provides a way to add effluent to container 504 such as hydrogen peroxide to induce controlled cell death or nutrients to promote cell growth.

Figure 6A:
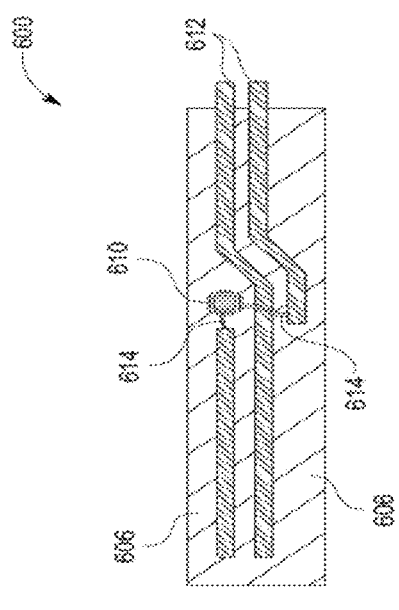
FIGS. 6A-6C are a depiction of an electromagnetic biophoton collector 600 according to one embodiment of the present invention.
Figures 6B, 6C:
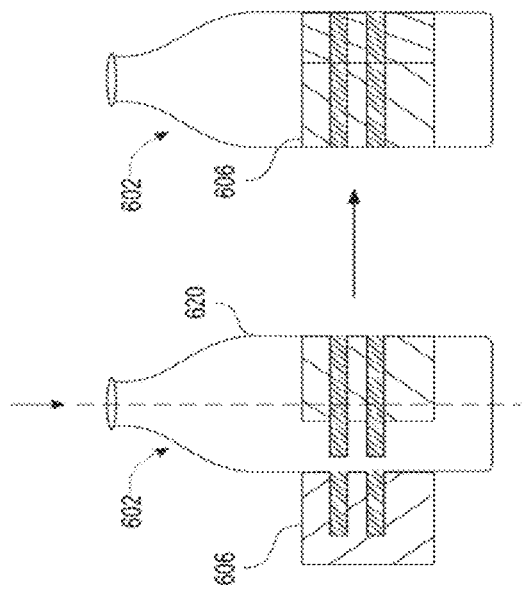

For biphoton emission of electromagnetic radiation in the radio wave or microwave spectrum, an antenna can be used. FIGS. 6A-6C are depictions of an electromagnetic biophoton collector 600 of one embodiment of the present invention.

Biophoton collector 600 is similar to that described in US Pat. Application Publ. No. 20010/0032437 (the entire contents of which are incorporated herein by reference). Biophoton collector 600 includes a container 602 for storing substances. The container 602 is provided with a radio frequency antenna 604. Circuitry 606 can include a chip 610, circuit paths 612 forming a coil of the antennae and wires 614 for connecting the circuit paths with chip 610.

As shown in FIGS. 6B and 6C, the circuitry is disposed on an exterior surface 620 of container 602 and in the embodiment shown encircles the container 602. Inside container 602 would be live cells. In one embodiment of the invention, an effluent can be added to container 602 such as hydrogen peroxide to induce controlled cell death or nutrients to promote cell growth. In one embodiment of the invention, biphoton emission as electromagnetic radiation would be collected and transmitted from circuitry 606 to a target treatment region.

In one embodiment of the invention, biphoton emission as electromagnetic radiation would be detected and its waveform characteristics would be stored by chip 610. In one embodiment of the invention, a radio wave or microwave generator (or another electromagnetic radiation broadcaster) could use the stored waveform characteristics to generate/simulate biphoton for transmission to a target treatment region.

Figures 1, 7:
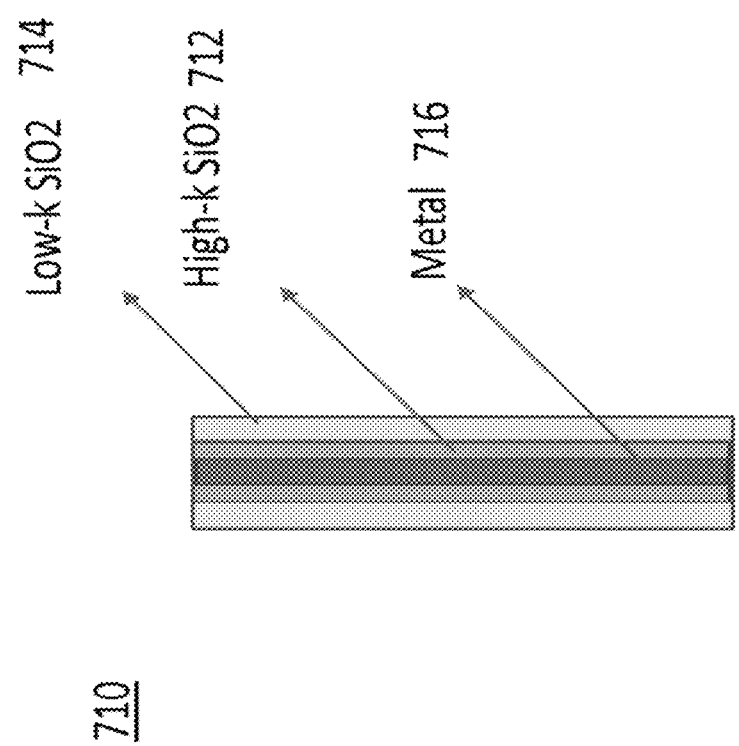
FIG. 7 is a depiction of a fractal antenna according to one embodiment of the present invention.
Figure 7:
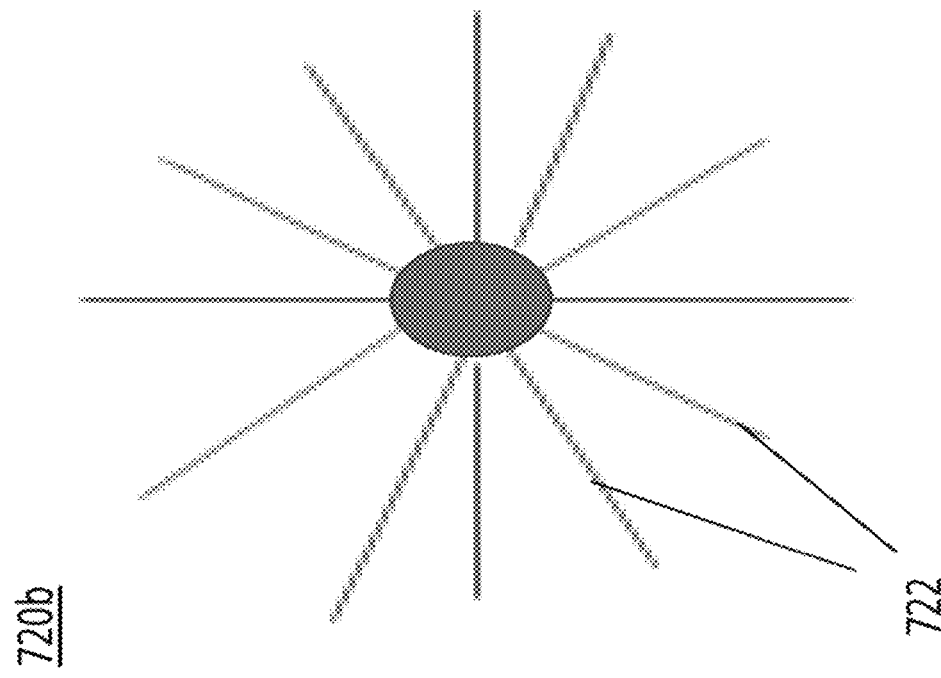
Figure 2:
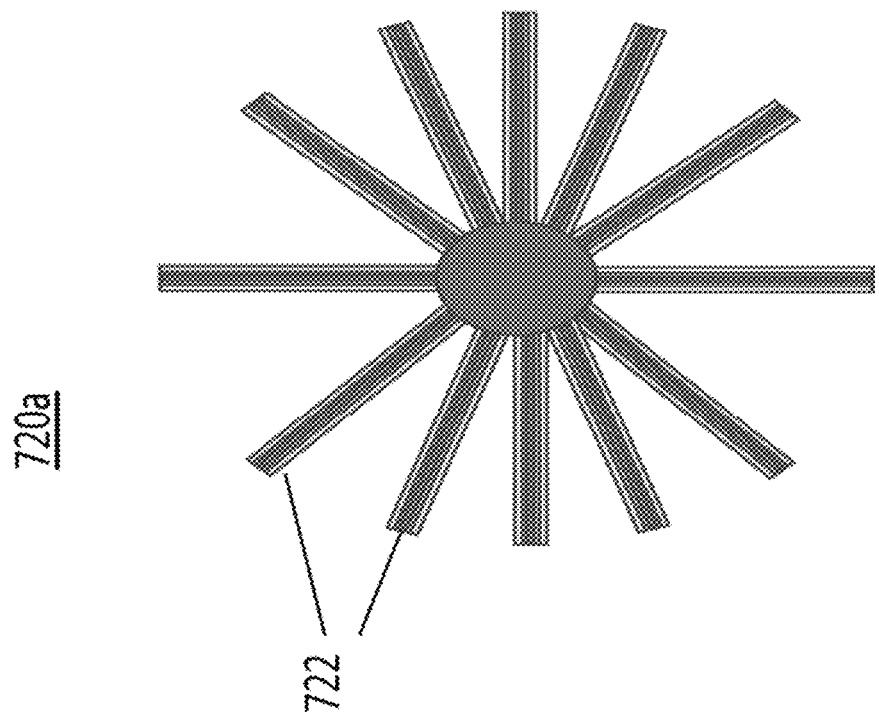
Figures 3, 7:
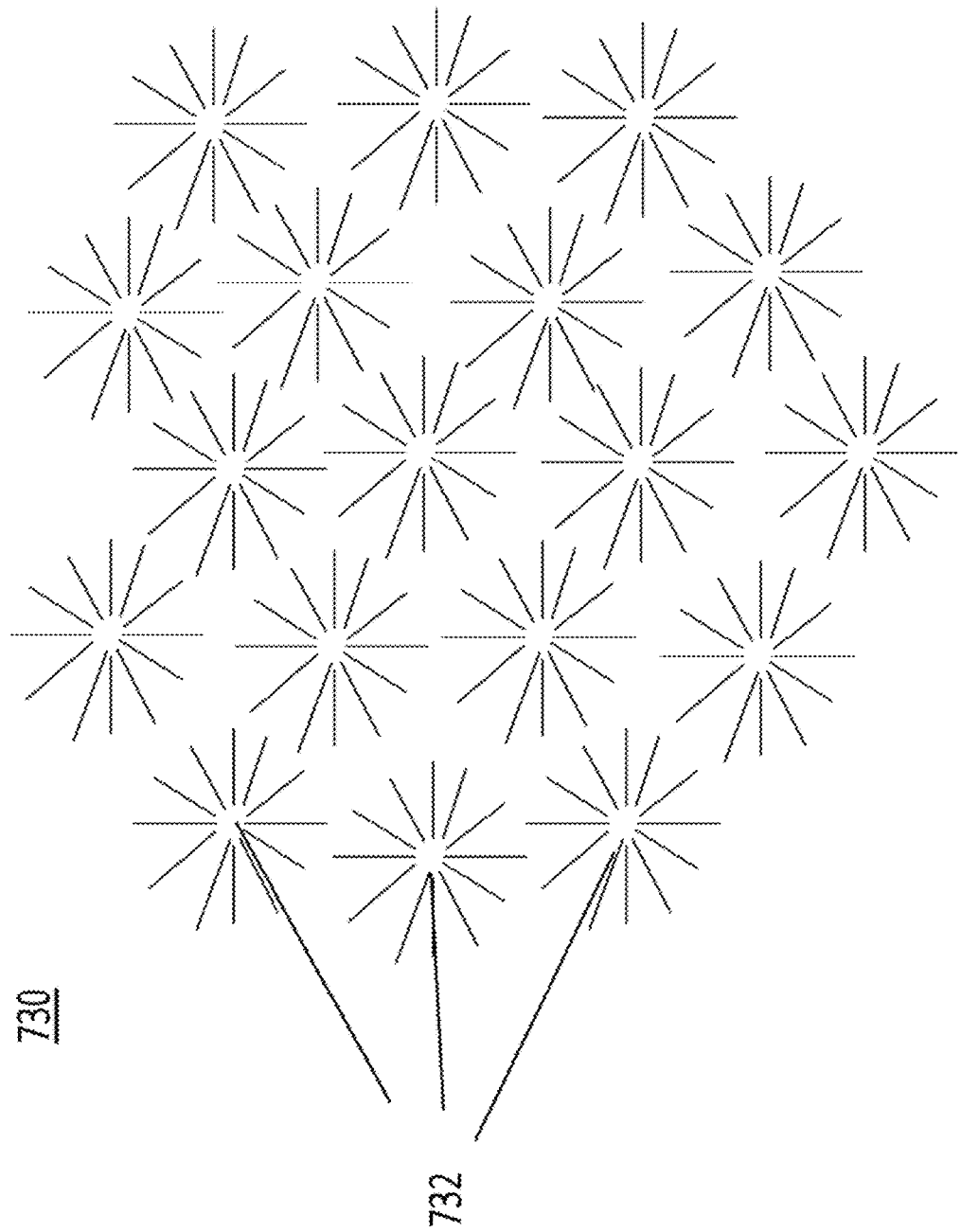
Figures 4, 7:
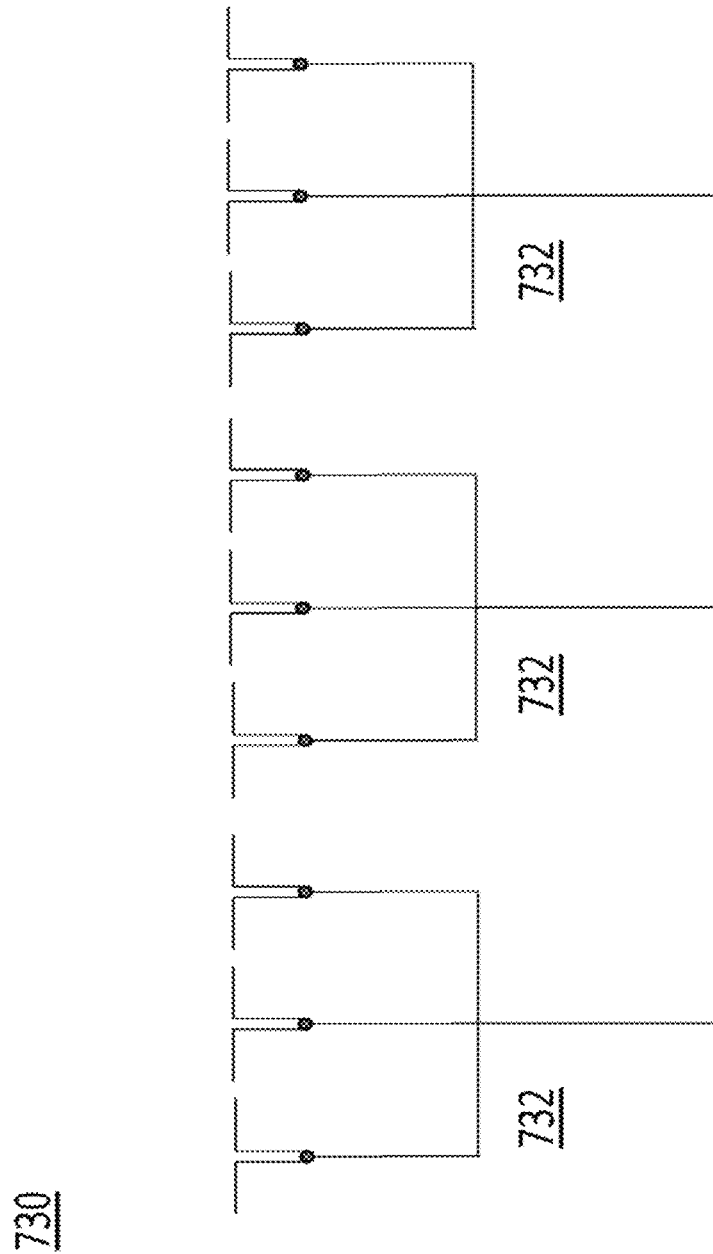
Figures 5, 7:
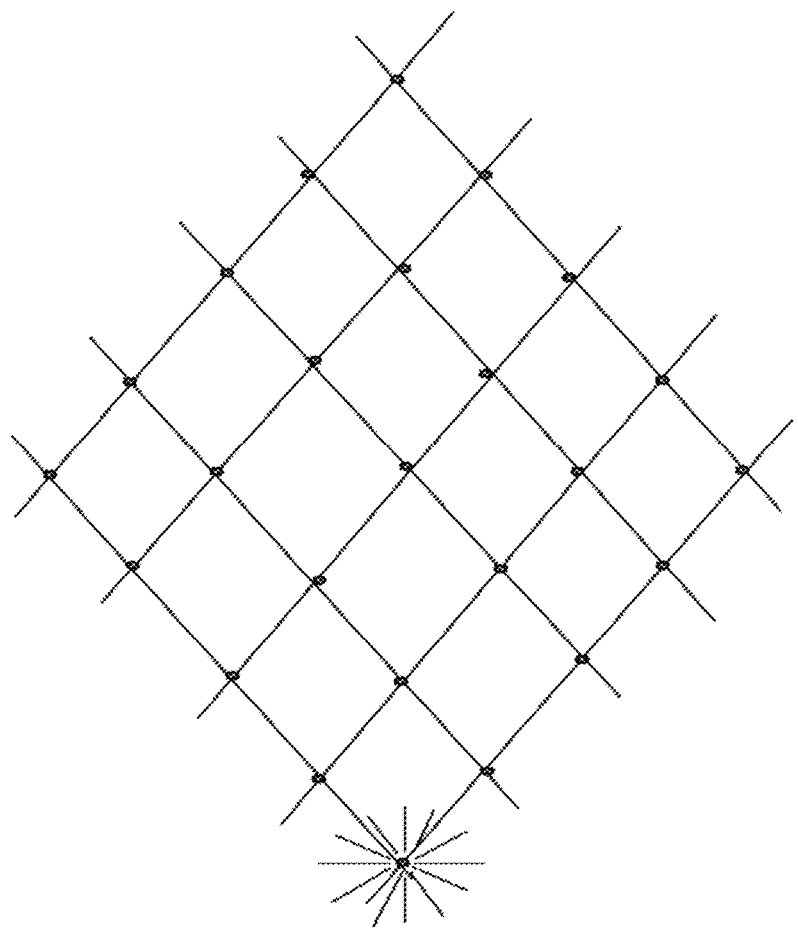

FIG. 7 is a depiction of a fractal antenna that can be used in one embodiment of the invention as the antenna for electromagnetic biophoton collector 600.

A fractal antenna uses a self-repeating design such as self-repeating design 702, or other fractal patterns. It can maximize the length of an antennae material in a total surface area. In general, fractal antennas are compact and have a wide band of operation because a fractal antenna resonates at many different resonances, meaning it can act as an antenna for many different electromagnetic frequencies. The different resonances arise because the fractal nature of the antenna acts as a virtual network of capacitors and inductors.

In one embodiment of the invention a fractal antenna could be printed (or otherwise formed) onto the external surface 620 of container 602. In one embodiment of the invention a fractal antenna could be printed (or otherwise formed) on a Petri dish. In one embodiment of the invention a fractal antenna could be printed onto a biocompatible polymer supporting living cells. These fractal antennae would be used to collect biophoton electromagnetic radiation.

Regardless of the antenna used, the antenna could be connected to a spectrum analyzer to evaluate the frequency characteristics of the electromagnetic radiation captured from the biological cells. Once measured, a rf or microwave generator could be used to replicate the measured spectrum.

Antenna Design for Light Collection:

Due to the circular polarization of light, it is difficult to maximize optical fiber coupling to the source of light, especially if the source of light is small and/or the intensity of light is very weak, as is generally thought to be the case for naturally occurring sources of biophotonic radiation. In one embodiment of the present invention, the circular polarization of the electric field of non-polarized light is best captured by an optical waveguide having metallized stubs of different orientations. In one embodiment, a stub would be dimensioned about ¼ wavelength wide by ¾ wavelength long, and the stubs would be oriented in all possible concentric and spherical radiated orientations. In one embodiment of the invention, the biophotonic activity taking place is measured either in-vivo through a window chamber (described below) or in-vitro in a well plate or in a container. A planar array, multiple stub configuration provides a unique antenna for other purposes and one that is suited for collection of biophoton radiation.

In one embodiment of the invention, the collection of biophoton radiation including light can use a fractal antenna design, similar to that described above for collection of electromagnetic radiation collection at radio or microwave frequencies, but in this embodiment designed for the visible light range or frequencies about the visible light range and much shorter that the radio or microwave frequencies. In one embodiment, the repetitive patterns do not have stubs with lengths shorter than $\lambda/8$. Preferably, the antennae stubs have lengths that range from near $\lambda/4$ to near $3\lambda/4$. Accordingly, if the intended light measurements are centered around 300 nm, for example, then the stub length of interest would be between 75 nm and 225 nm.

The fabrication of the antenna can be performed using well known semiconductor processes for build-up of small metallic features, including, but not limited to, low-k $SiO_2$ dielectric, and high-k $SiO_2$ dielectric. The growth of various layers could be done through a sequential build-up process. The metallized features can be achieved through metal atomic layer deposition (ALD) or through other metal deposition processes known in the art such as sputtering or evaporation, with photo-resist processing used to pattern the deposited metal layer(s) leaving the appropriate metallized patterns of interest. The metallic pattern in one embodiment would be surrounded by a high-k dielectric in contact with the metal, and that structure embedded inside a low k dielectric to a form a sensitive optical waveguide that is capable of detecting the stimulus of a weak electric field from the bio-photonic activity.

Metallic features are considered in electromagnetic theory to have an infinite dielectric constant, and are therefore able to pick up an oscillating electric field of the biophotons. The electromagnetic energy propagates along the path of the highest dielectric constant which in this case is the metal. The light can and will propagate along a path with the high k $SiO_2$ dielectric. However, due to internal scattering, the light will remain confined to the high-k $SiO_2$ dielectric and the metal. Any time the electromagnetic energy approaches the boundary interface between the high-k $SiO_2$ and the low-k $SiO_2$, it will bend back and confine itself to the intended waveguide area formed by the metallic path as surrounded by the high k dielectric material. FIG. 7-1 is a schematic showing a section of waveguide 710 with a high-k dielectric material 712, a low-k dielectric material 714, and a central metal 716

Figure 2:
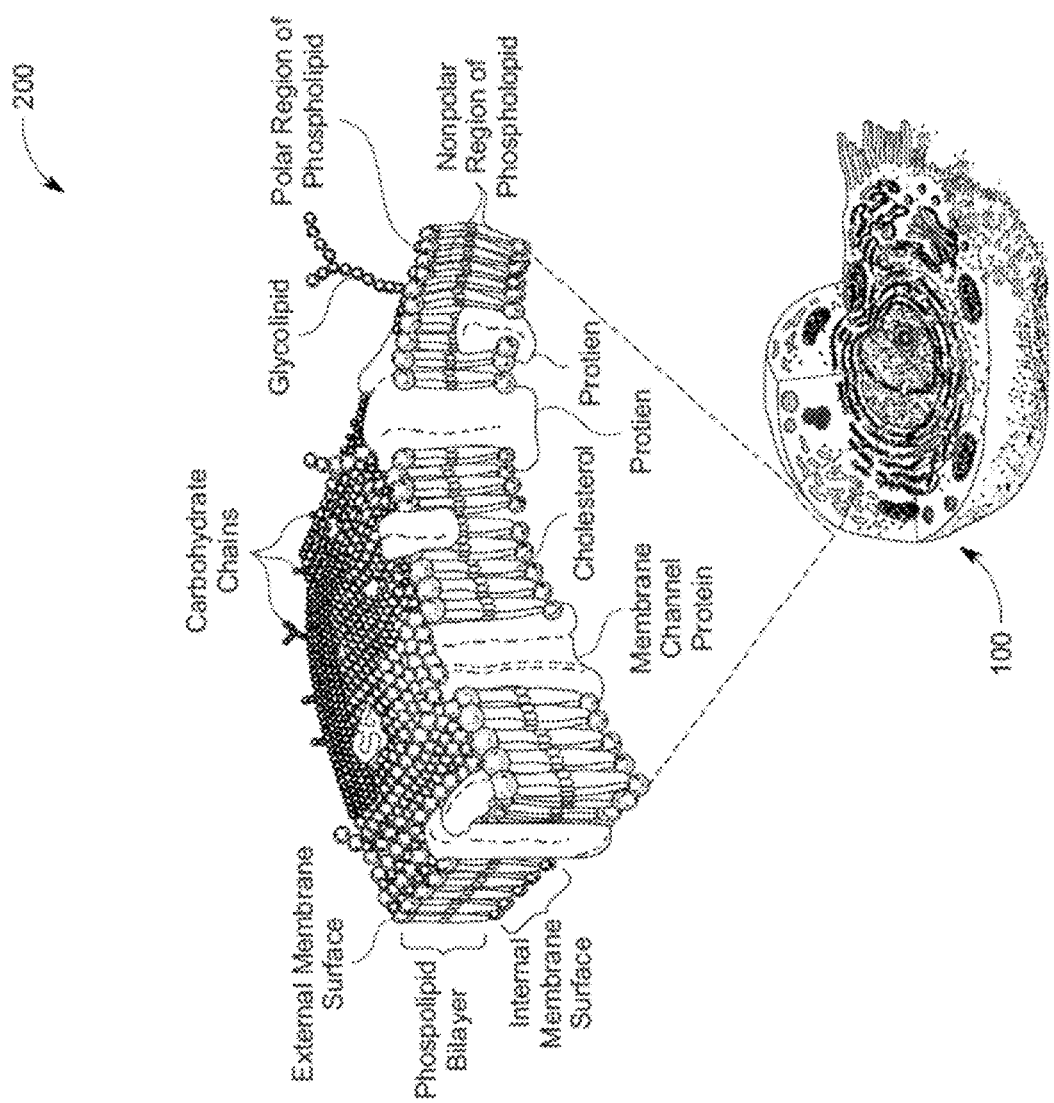
FIG. 2 illustrates a schematic drawing of the structure of a plasma membrane 100 of the cell 100 shown in FIG. 1.

The patterning can be done on a quartz wafer of appropriate dimensions. The antenna pickup area is preferably of an open concentric polarization construction 720a as shown in FIG. 7-2.

Metal stubs 722 extend radially from a common center. Other patterns are possible and can be used, including the simpler representation of the open concentric polarization construction 720b also shown in FIG. 7-2.

FIG. 7-3 depicts an array 730 of antennae 732 configured on a quartz wafer (not shown). Various patterns are possible depending on the intended use. As an example, the arrayed antennae each have pick up stubs that are concentric and planar as shown in FIG. 7-3.

The antenna stubs connect with an internal column (see internal column 766 shown in FIG. 7-7) made of the same materials design as FIG. 7-1 having a configuration with a metal core, surrounded by a high k $SiO_2$ dielectric and a low k $SiO_2$ dielectric that forms the optical waveguide. The metal can be, but is not necessarily, made of a metal enabling a photoelectric effect.

A cross section of the stub configuration 730 shown in FIG. 7-3 with antennae 732 interconnected together is shown in FIG. 7-4.

FIG. 7-5 is a schematic of multi-up arrayed antenna 750.

Figures 6, 7:
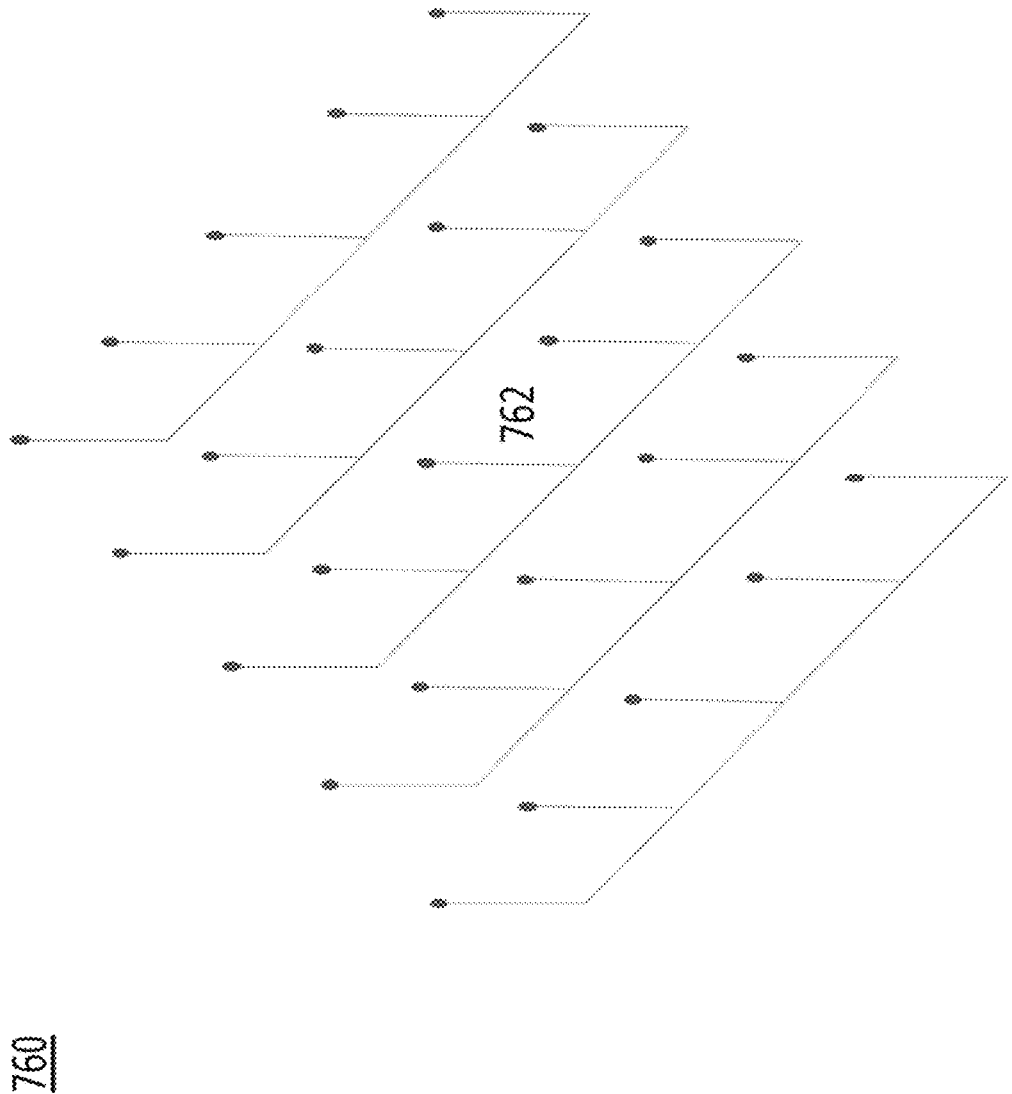
Figure 7:
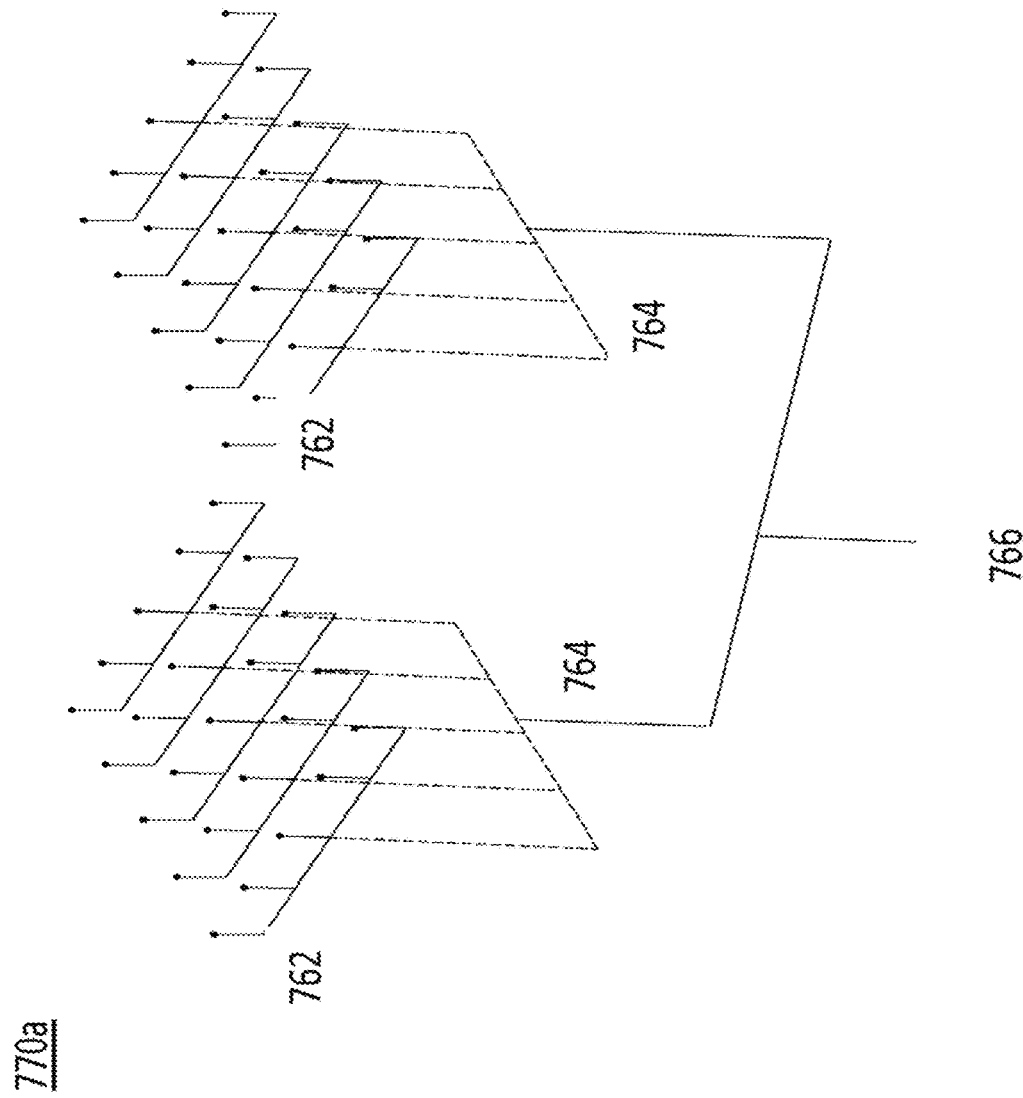

FIG. 7-6 is another schematic of the multi-up arrayed antenna 750 shown in FIG. 7-5 showing a top-level interconnection network 762 under the top surface of multi-up arrayed antenna 750.

FIG. 7-7 is another schematic of the multi-up arrayed antenna 750 shown in FIG. 7-5 showing the full interconnection network including top-level interconnection network 762 and bottom-level interconnection network 764.

Figures 7, 8:
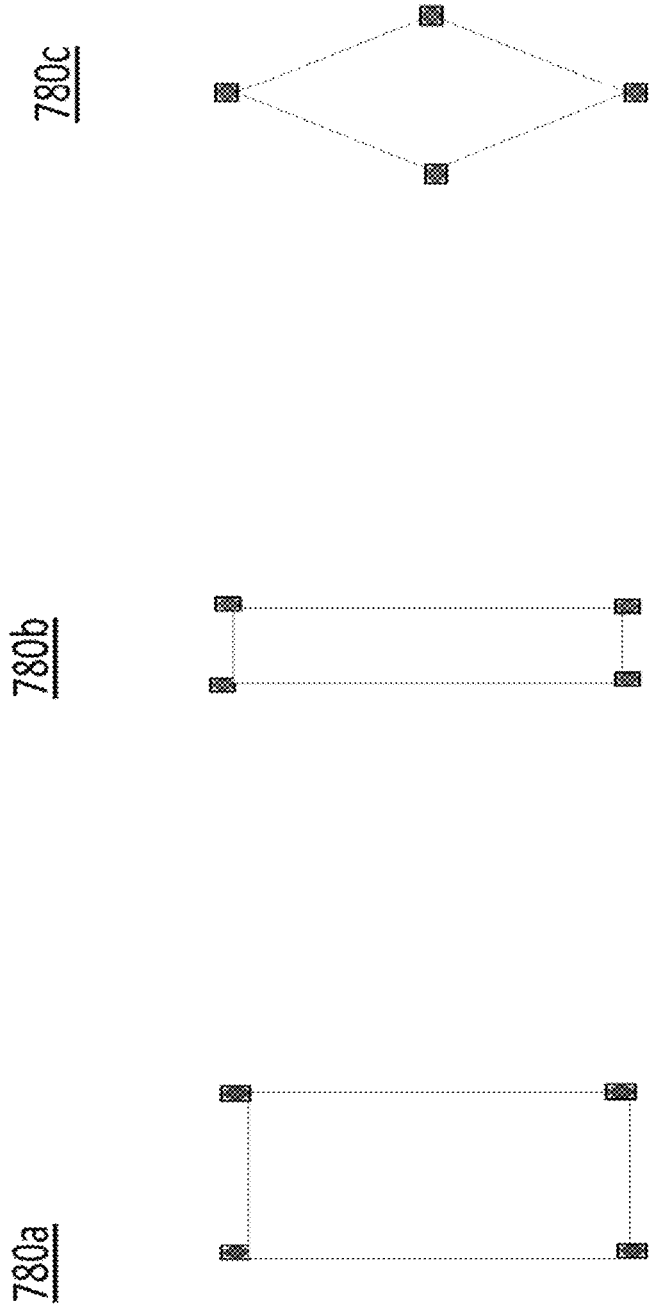

FIG. 7-8 is a depiction of antennae that can be arrayed in different manners including a square antenna 780a, a rectangular antenna 780b, and a diamond shaped antenna 780c.

Figures 7, 8, 9:
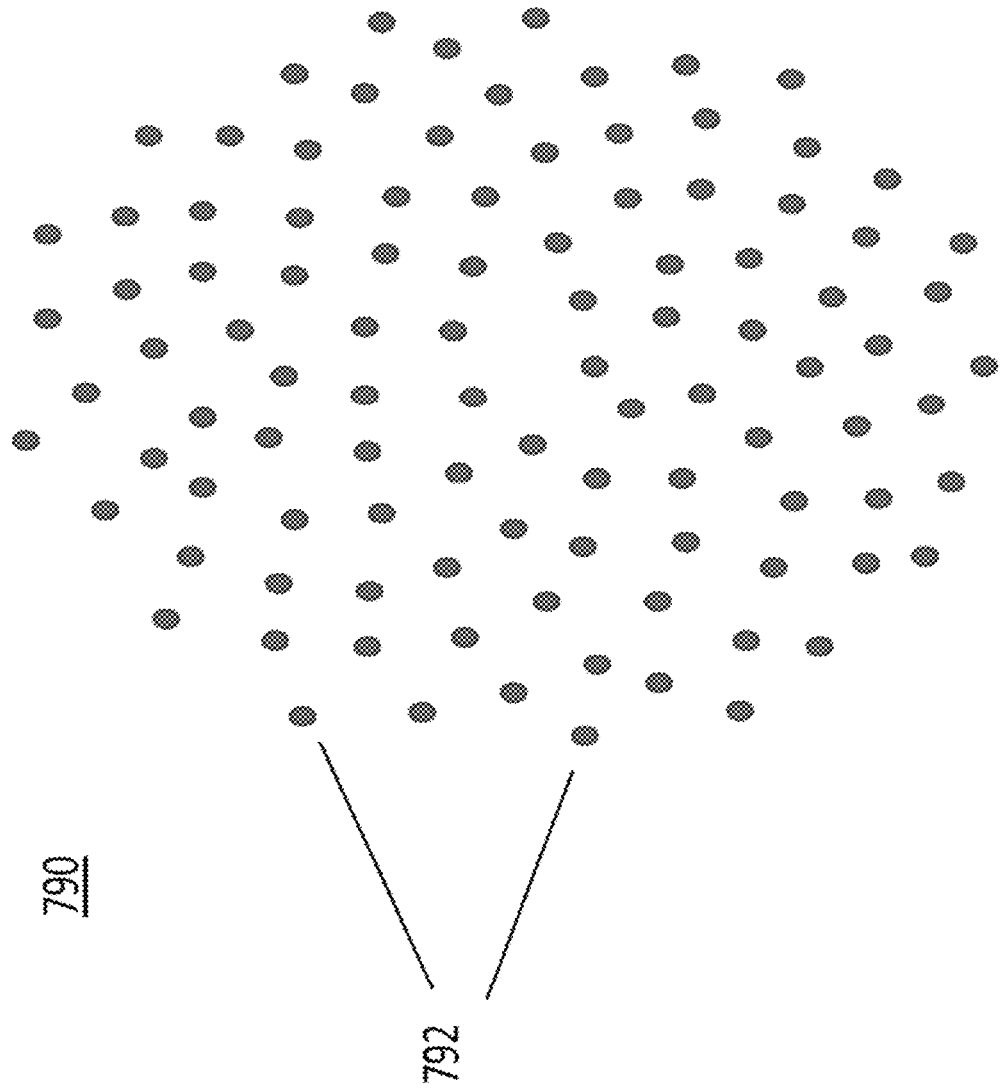
Figures 7, 8, 9, 10:
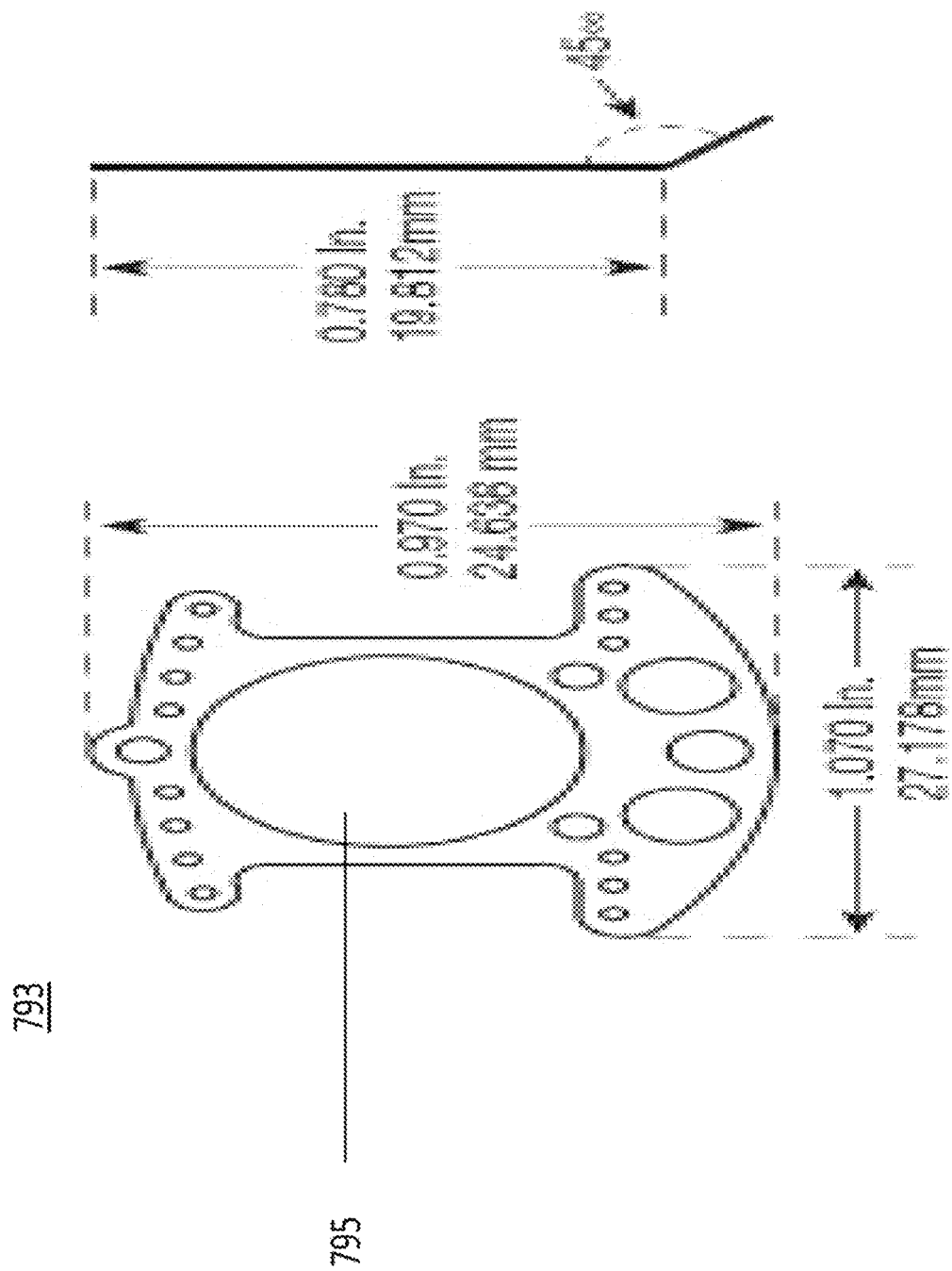

FIG. 7-9 is a depiction of a spiral-type packing arrangement 790 where each antenna petal 792 is placed at 0.618034 per turn (out of a 360° circle) allowing for the best possible exposure to cellular-light. This desirable spiral arrangement follows from what is commonly referred to as the Fibonacci sequence.

The resulting multi-up pattern has a high density and a spiral configuration similar to the one found in pine cones and sunflowers. This spiral pattern is desirable for the packing it enables.

This patterned antenna can be built on a quartz wafer of any size that can fit within semiconductor equipment capability. A quartz wafer hosting thousands of antennae (2,000 to 100,000 antennae) can be built. This quartz wafer can be used in accordance to the window chamber model. Similarly, the quartz wafer equipped with fractal antennae can be used inside a polycarbonate well plate. The cell plating can be performed on top of the quartz wafer with embedded fractal antennae. Various experiments can be envisaged to elucidate the light-based communication inside of a single cell or amongst multiple cells. The ability to conduct photonic measurement in-vivo using fractal antennae permits one to measure biophoton radiation from living tissue in vivo or in vitro.

As in other embodiments discussed above, once measured, these signals can be transmitted from their source to a treatment site or could be duplicated to mimic biophoton radiation.

In-Vivo Measurements of Bio-Photonics:

The window chamber mouse model has gained great acceptance for conducting medical research in-vivo while maintaining the ability to see through for direct observation and monitoring. FIG. 7-10 is a depiction of a window chamber according to one embodiment of the invention, where the window area 795 is constructed for transmission of biophoton radiation therethrough.

For example, window chamber 793 could be equipped with fractal antennae (of the same or different designs) to permit measurements of photonic activity as well as having the ability for direct observation and monitoring. For fractal antennae, the antenna patterning in at least one portion of the window 795 can be made with antenna elements dimensioned at subwavelengths of visible light so that observation of the biological region underneath window chamber 793 is possible. The fractal antenna can be as described herein above, or can be any desired fractal antenna configuration.

FIG. 7-11 is a depiction of a window 795 made of a quartz wafer that has different sections that are independent of each other. This design permits the photonic activity to be measured from different sectors of the subject. In one embodiment, window 795 of FIG. 7-11 could be used to answer the question if there is (ON) or if there is not (OFF) photonic activity. The wavelength or spectral information could be collected and stored regardless of whether the antenna was sectioned or not.

FIG. 7-11 also illustrates one embodiment of the invention where the antennae are sectioned such that photonic activity (or the absence thereof) can be monitored from each section. Each fractal antenna in window 795 could be connected to separate fiber optic columns 766, or all the fractal antennae in each section could be connected together to one common fiber optic column 766.

The Biophoton Bypass

Complicating the literature recognized problem that biophoton radiation is weak is the further problem that these weak signals (naturally originating inside a subject) travel in a dispersive medium with scattering and absorption making it unlikely that the biophoton radiation can travel extended distances. Even the distances of mm in the in vitro test cells are remarkable. The inventive solution: bypass nature's dispersive optical pathway with an artificial conduit (hereinafter the "biophoton bypass") having little if any scatter and low absorption.

The biophoton bypass might have physical characteristics of a fiber or fiber bundle if the bio-photons needed to be transmitted over significant distances, as from outside the body into the body or from one region of the body more accessible for the control than the target region.

The biophoton bypass might have physical characteristics of an optical sheet with evanescent waves from the sheet penetrating a shallow depth into a diseased organ.

The biophoton bypass might be a simple polymeric window separating a control region from the diseased organ made along the ways described in the Yevgeny patent application U.S. Pat. Appl. Publ. No. 2009 (discussed in more detail below).

The biophoton bypass might be capillary filled with a protein solution. In prior work, a narrow capillary was filled with a dilute protein solution and exposed to MGR (another name for biophoton radiation) on one end. No radiation was detected at the other end until the protein filed capillary was aligned with an electric field. Hence, in one embodiment, the biophoton bypass of the invention could be a protein-filled conduit wherein an applied electric field which can "gate" to either turn on or turn off the transmission of biophotons along the protein-filled conduit.

In one embodiment, the biophotons emitted from one cell induce photo-assisted reactions in a nearby or proximate cell that itself produces its own biophotonic emission, thereby leading to biophoton emission from one cell to another cell, appearing as a "communication" across many cells.

In one embodiment, the biophotons are emitted from excited states of luminescing species. The set of excited states can be considered a "bioplasma." In this context, bioplasma is a term derived from bioelectronics, molecular biology and solid state plasma physics and refers to a state in which biomolecules in vivo are predominantly in a stable, collective, excited state. It is considered a "cold plasma" that forms an energetic and informational network throughout the organism involving a colloid of semi-conducting proteins as the main constituent in a redox (oxidation-reduction) chemical oscillator displaying complex dynamics. This is analogous to a low-power laser that uses chemical, electrical or magnetic energy to pump it into an excited metastable state.

Coupling between the biochemical reactions of the living state takes place electromagnetically, with a wave-like internal coordination surrounded by an electromagnetic wave externally emitted. Biological effects of exogenous electromagnetic fields are ascribed to collective resonance properties of the whole bioplasma and not just to any of its individual parts.

Accordingly, in one embodiment of the invention, the collective state of this bioplasma can be influenced by localized changes. One candidate to influence local changes would be the application of an electric field, to change the polarization of the cells and turn off (or on) chemical reactions. Other candidates are described in more detail elsewhere but include providing ultrasonic, microwave, or localized cooling to selected portions of cells in an organ.

Regardless of the collection technique, an energy transmitting structure (as the biophoton bypass) could carry the biophotons to a target site. An optical fiber could be used if the biophoton light were in the UV to near IR range. In one embodiment, vacuum/air would be the most reliable medium for the biophoton bypass. Accordingly, a hollow optic could be used for a biophoton bypass of the invention for transmitting biophotons in the UV to near IR range inside the hollow optic while bypassing media of the subject to be treated. FIG. 8 is a depiction of a hollow optic biophoton bypass 800 according to one embodiment of the invention. U.S. Pat. No. 8,454,669 (the entire contents of which are incorporated herein by reference) describes a similar device for UV phototherapy. In the hollow optic biophoton bypass 800 of the invention, there are walls 802 which define a hollow cavity 804 filled with air, a gas, or possibly under a vacuum for transmitting UV light into a subject could be utilized in this invention. The interior surfaces 806 would be highly reflective surface. At the distal (or exit) end 810, there would be a light optic which could either disperse or concentrate the biophoton light flux into a treatment site.

Figure 9A:
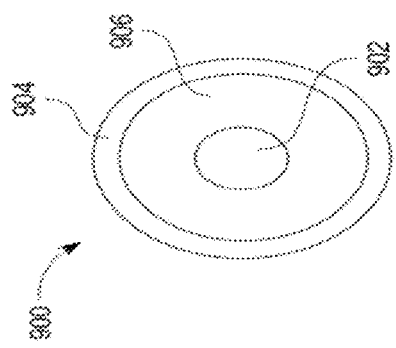
FIGS. 9A and 9B are a depiction of an electrically conducting biophoton bypass 900 according to one embodiment of the present invention.
Figure 9B:
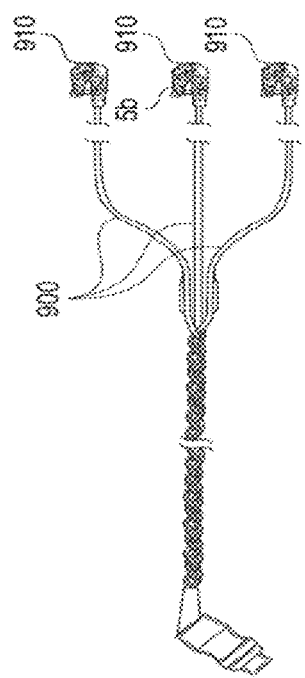

If the biophotons are low frequency electric signals (including a DC field), then a wire or conductive trace (as the biophoton bypass) could be used to transmit the low frequency electric waves. FIGS. 9A and 9B is a depiction of an electrically conducting biophoton bypass 900 according to one embodiment of the invention where low frequency electric signals are transmitted therein while bypassing media of the subject to be treated. The conductors 902 shown in FIG. 9A are similar to those described in U.S. Pat. No. 7,272,427 (the entire contents of which are incorporated herein by reference) where the conductors in the '427 patent were used to measure bio-electric signals from the heart muscle while a patient was in an MRI environment. Here, in the FIG. 9A embodiment of this invention, the electrically conducting biophoton bypass 900 has an electrically conductive part 902 and a sheath part 904 arranged over conductive part 902. The conductive part 902 and sheath part 904 are separated by a dielectric 906. The electrically conducting biophoton bypass 900 can include multiple conductors 902 terminating on connectors 910 (FIG. 9B) for attachment to a subject to be treated. Connectors 910 conductors can be attached to the living cells noted above and/or to a target region if the wire or conductive trace is being used as a biophoton bypass to deliver the low frequency electric signals from a source of the low frequency electric signals to a target site for treatment. In one embodiment, as shown in FIG. 9B, the multiple conductors 902 with multiple sheaths (not shown) are twisted together to reduce high frequency noise.

Figure 10A:
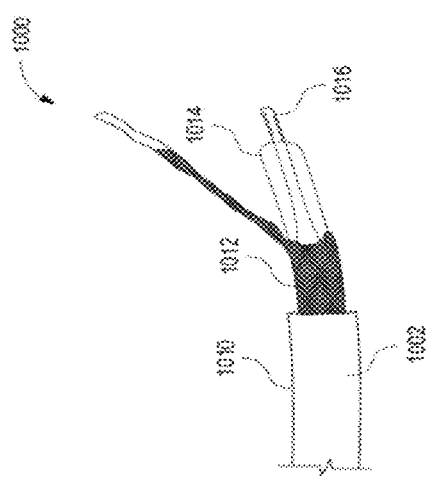
FIGS. 10A and 10B are a depiction of another electrically conducting biophoton bypass 1000 according to one embodiment of the present invention.
Figure 10B:
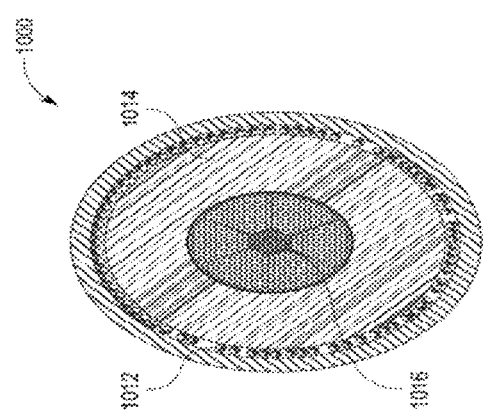
Figure 11:
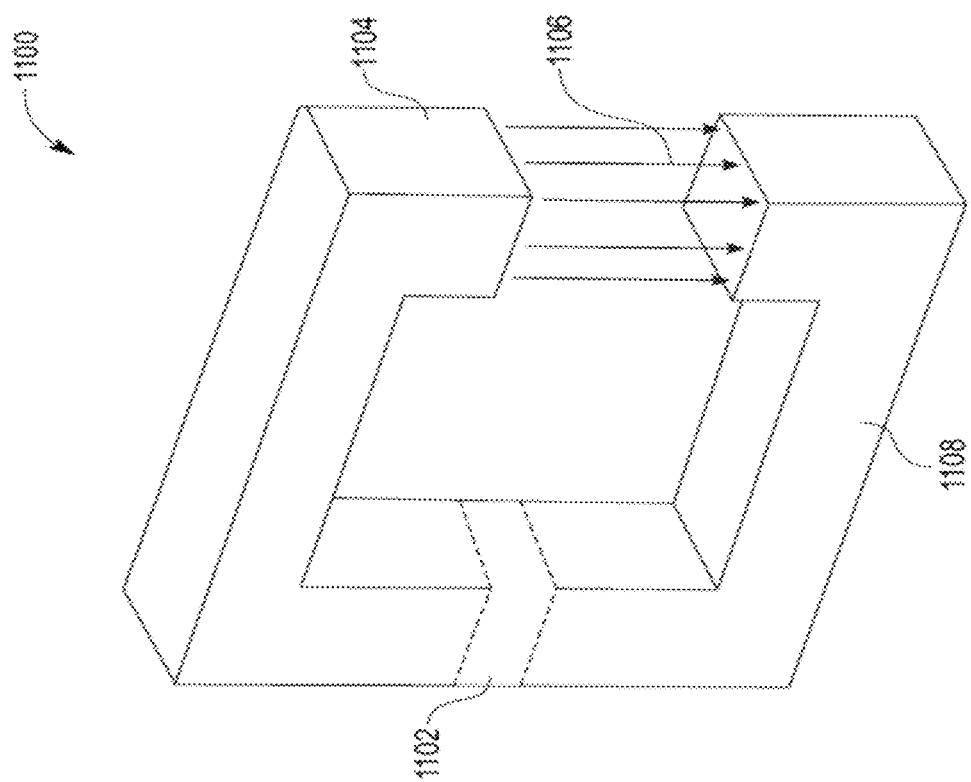

FIGS. 10A and 10B are a depiction of another electrically conducting biophoton bypass 1000 according to one embodiment of the invention where the biophotons as high frequency electrical waves are transmitted therein while bypassing media of the subject to be treated. In the example of FIG. 10B, a coaxial cable 1002 is used. Waveguides (as biophoton bypasses) can also be used to transmit high frequency electrical waves. These devices (coaxial cables and waveguides) are highly selective for delivery of specific frequencies of radiation. As shown in FIG. 10B, the electrically conducting biophoton bypass 1000 includes a coaxial cable 1002 having an outer plastic sheath 1010, a woven copper shield 1012, an inner dielectric insulator 1014, and a copper core 1016. The core 1016 could be made of other metals or alloys, but copper is commonly used. A coaxial cable differs from other shielded cables because the dimensions of the cable are controlled to give a precise, constant conductor spacing, which is needed for the coaxial cable to function efficiently as a transmission line.

Figures 7, 8, 9, 10, 11:
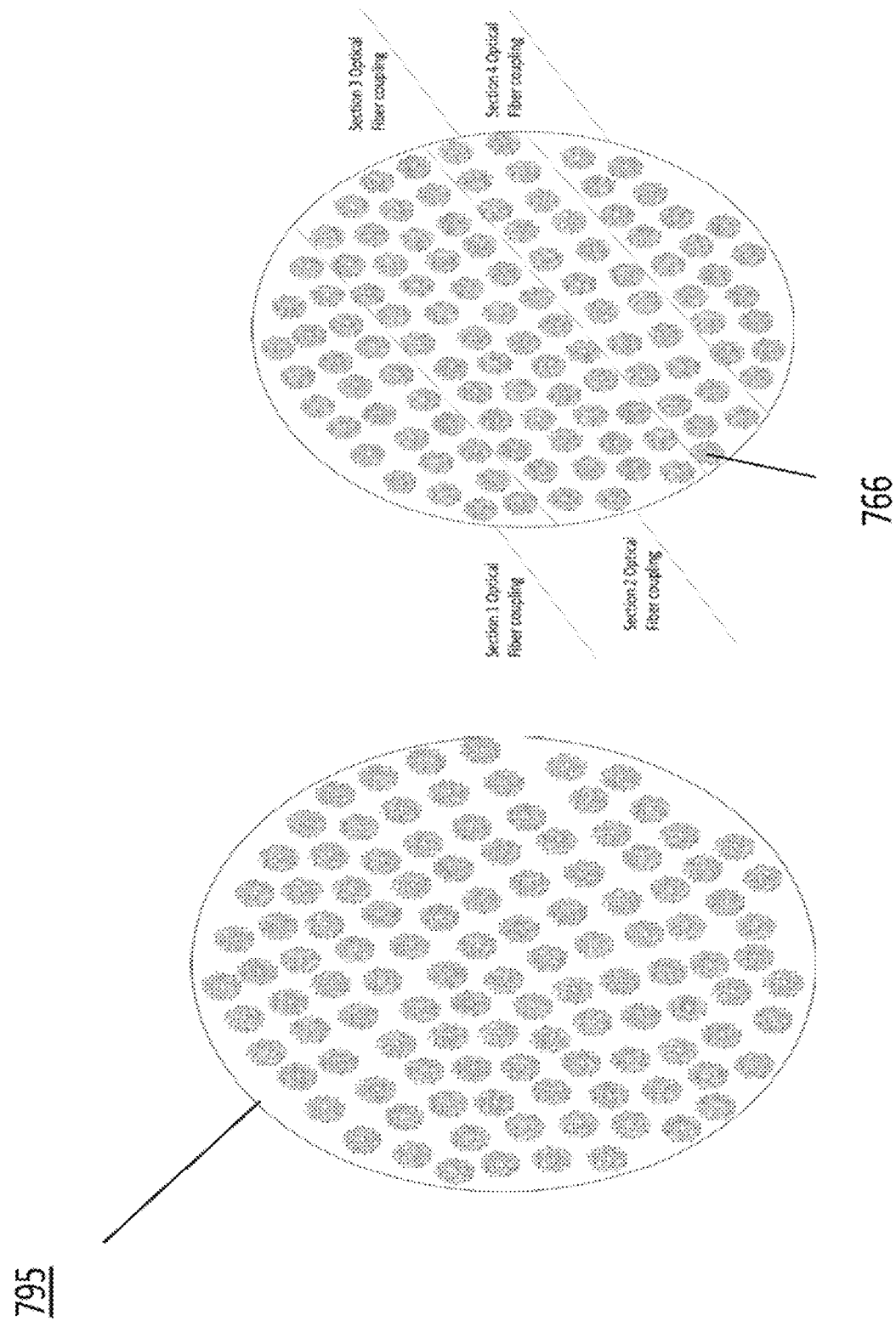
Figure 8:
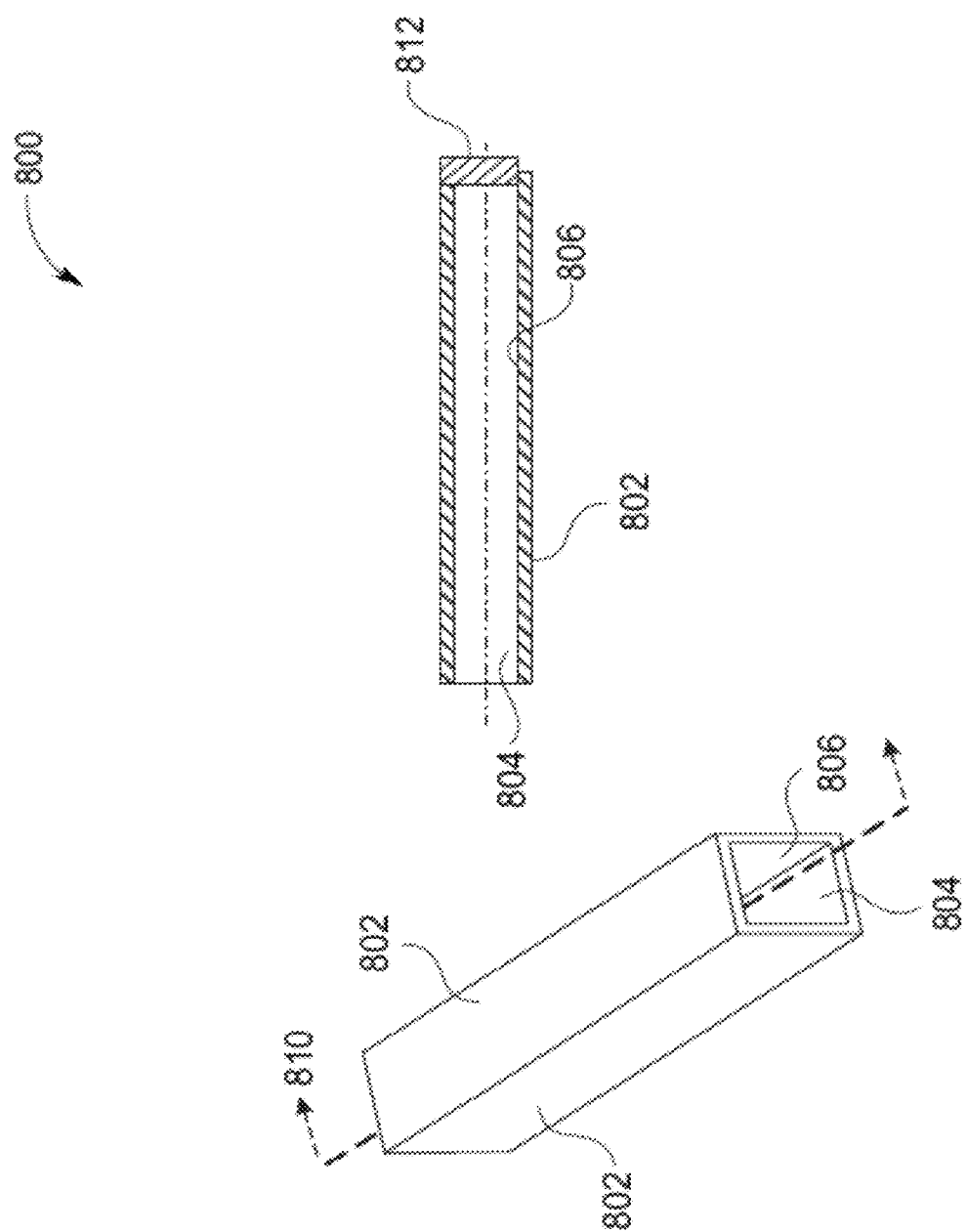

FIG. 11 is a depiction of a magnetic biophoton bypass 1100 according to one embodiment of the invention where the biophotons as time-varying or static magnetic fields are transmitted therein while bypassing media of the subject to be treated. As shown in FIG. 11, magnetically permeable materials form a magnetic circuit (as the biophoton bypass) carrying the time-varying or static magnetic field from a source to a target. The magnetic biophoton bypass 1100 utilizes a dual gap design. In one gap, there is a source of the magnetic fields. As shown in FIG. 11, in one gap, there is disposed a cell containing living tissue, that is living cell biophoton emitter 1102 which is a source of magnetic biophotons. The magnetic yokes 1104 and 1108 form a "circuit" carrying the magnetic field in the circuit from the living cell biophoton emitter 1102 through magnetic yoke 1104 to a target or treatment region 1106, and back by magnetic yoke 1108 to the living cell biophoton emitter 1102.

In a further embodiment of the present invention, the biophoton radiation applied to a first region is capable of triggering an altered metabolic activity in one or more cells, preferably in the 100 GHz to 10 THz region, which triggers the cell(s) to undergo altered metabolic activity, and optionally, to further trigger subsequent biophoton emissions from the cell(s). Microwave broadcasters or microwave waveguide structures can be used to apply these frequencies to a target structure.

In one embodiment, the spiral chains of DNA naturally present in biological materials are used to transmit radiation in the frequency range of 100 GHz to 5 THz or are used for charge transport or signaling along DNA traditionally thought to be "satellite" or "junk" DNA (hereinafter referred to as "signaling DNA"). This signaling DNA corresponds to approximately 98.5% of the DNA strand, with only about 1.5% of the DNA strand functioning genetically to code for proteins or RNA, etc. Traditionally believed to be merely composed of various repeating nucleotide base fragments having no function, the present inventors propose that this signaling DNA actually can (and does) function as one of the components of cell-to-cell communication or signaling within humans, as well as other animals. That the signaling DNA has some form of function has also been hypothesized by others (see, e.g., Jiin-Ju (Jinzhu), "PHYSICAL PROPERTIES OF BIOPHOTONS AND THEIR BIOLOGICAL FUNCTIONS", Indian Journal of Experimental Biology, Vol. 46, May 2008).

Figure 12:
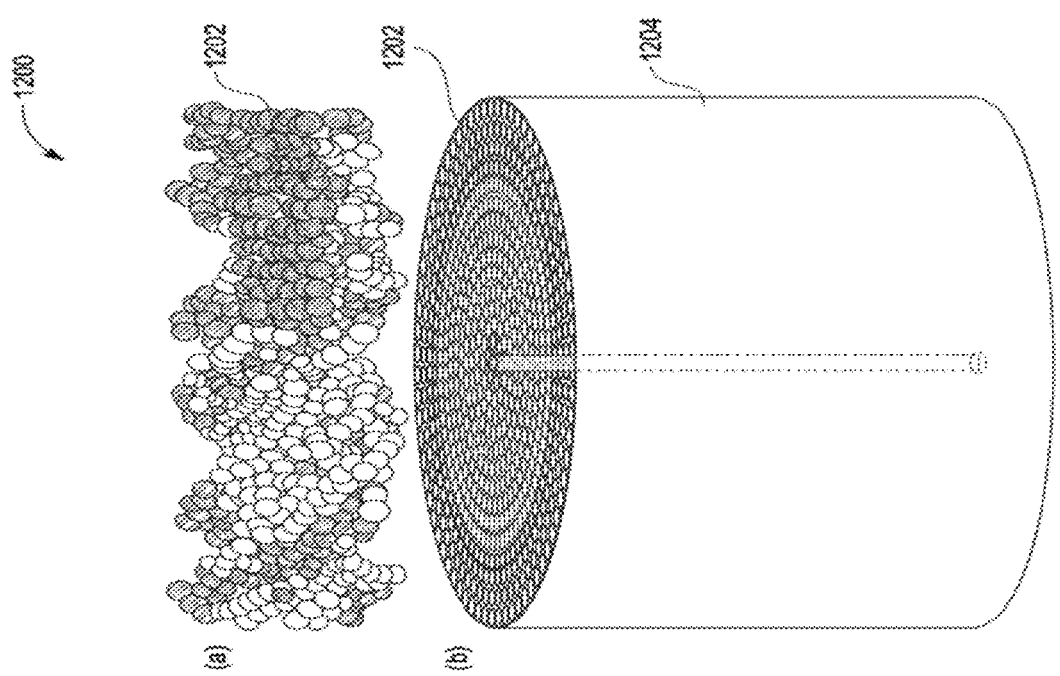
FIG. 12 is a depiction of a DNA-based biophoton bypass 1200 according to one embodiment of the present invention.

FIG. 12 is a depiction of a DNA-based biophoton bypass 1200 according to one embodiment of the invention where the biophotons in the frequency range of 100 GHz to 5 THz are transmitted therein while bypassing media of the subject to be treated.

In FIG. 12, the signaling DNA 1202 is included in a waveguide type outer structure 1204. The length and diameter of the outer structure 1204 is sized according to the frequency range to be transmitted. Lithographic and printing processes can be used to generate trenches in silicon substrates that could both hold the signaling DNA and form a waveguide structure for propagation of biophotons in the frequency range of 100 GHz to 5 THz across the surface of the silicon substrate and to a treatment site. Wafer thinning processes known in the art could be used to thin the silicon wafer making the DNA-based biophoton bypass 1200 potentially a flexible biophoton bypass.

Accordingly, in various embodiments of the invention, the application of biophoton radiation to a target structure may directly affect a diseased region or it may enhance biophoton emissions from a first region (where cell death is being artificially induced) to a second or treatment region) This biophoton emission may act as a way of "communicating changes" in the first or control region which induce changes in the second or target region. This artificial biophoton emission may also act to enhance naturally occurring biophoton emission. This biophoton emission may also result in quantum coupling between the control and the target regions.

Accordingly, in various embodiments of the present invention, the first and second regions are "coupled" to each other with a medium (whether artificial or natural or that intrinsically present in the biological materials of the first and second region) that transmits bio-photons to the target region as a way of "communicating changes" in the first or control region which induce changes in the second or target region.

Living-Cell Biophoton Radiators

Accordingly, in one embodiment of the present invention, live biological cells in a container could be used as a source of biophoton radiation. A number of ways can be used to form this type of source. In one example, a Petri dish or container outside the subject could contain the live biological cells. See FIGS. 5 and 6. In one embodiment of the invention, the base of the Petri dish would contain a radiation collector in near direct contact with the living cells. The radiation collector would have (if needed) a thin passivation layer to insure that the materials of the radiation collector do not interact with the solutions in the petri dish. Biophoton radiation emitted from the biological cells would be captured by the optical collector and then transmitted to a treatment site, for example inside the subject. For example, a cancer strain (the same or similar to that of a patient) could be treated in a container with hydrogen peroxide to induce cell death. The biophoton radiation would be collected from the container and transmitted in a biophoton bypass (bypassing intervening tissue of the patient) into the diseased region promoting cell death.

U.S. Pat. Appl. Publ. No. 2009/0203530 (the entire contents of which are incorporated herein by reference) describes a method for producing polymers having properties suitable for catalytic activity or binding activity, via evolutionary nucleic acid-mediated chemistry. As described in the '530 application and suitable for the present invention, non-biological polymers (e.g., polymers other than DNA, RNA, or protein) can be synthesized. Such polymers include, but are not limited to, peptide nucleic acid (PNA) polymers, polycarbamates, polyureas, polyesters, polyacrylate, polyalkylene (e.g., polyethylene, polypropylene), polycarbonates, polypeptides with unnatural stereochemistry, polypeptides with unnatural amino acids, and combination thereof. In certain embodiments, the polymers comprise at least 10, 25, 75, 100, 125, 150 monomer units or more. These polymers could be used to encapsulate the biological cells of the living-cell biophoton radiator.

In this embodiment, a living-cell biophoton radiator could exist outside the patient or be surgically disposed inside the patient at the diseased site. U.S. Pat. No. 8,999,376 (the entire contents of which are incorporated herein by reference) describes tissue patches comprising fibrinogen (and/or fibrin). This type of fibrin glue has been approved by the FDA and can be used to impart topical hemostasis, provide sealant properties that are suitable is some clinical applications, and promote tissue approximation. Fibrin glue mimics the final steps of the coagulation cascade. FIGS. 13A and 13B are a depiction of a living-cell biophoton radiator 1300 according to one embodiment of the invention where living cells are added as a part of living cell layer 1320.

The matrix 1310 shown in FIG. 13B can be in the form of a cylindrical disc 1350 with a substantially circular cross-sectional geometry. In other embodiments, the matrix 1310 (or the entire tissue patch) can have other cross-sectional geometries such as, for example, substantially elliptical, polygonal (e.g., including any number of sides such as in the form of a triangle, a quadrilateral (e.g., rectangular or substantially square), etc.), irregularly-shaped, or any other suitable shape.

In the present invention, these types of patches 1310 can be applied to organ tissue. For example, matrix 1310 would be attached to an organ (not shown). Living cells of a kind similar to that to be treated using biophoton radiation would be contained in living cell layer 1320. An encapsulant layer 1330 would be applied over the living cell layer 1320. In one embodiment of the invention, encapsulant layer 1330 would contain either a substance to promote cell growth or a substance to promote cell death which would be controllably released into the living cell layer 1320.

As the cells in the living cell layer 1320 are affected by the substances released from the encapsulant layer 1330, biophoton radiation from living cell layer to the organ is achieved. Alternatively, encapsulant layer 1330 could contain phosphors or other elements such as metals significantly heavier than carbon for preferential absorption of x-rays (with the phosphors producing ultraviolet or visible light) or for preferential absorption of microwaves (with the metals locally heating). In one embodiment, the UV or visible light or the local heating would "stress" the cells in living cell layer 1320 to thereby produce biophoton radiation.

U.S. Pat. Appl. Publ. No. 2010/0120117 (the entire contents of which are incorporated herein by reference) describes polymers may be used to coat living cells in cell therapy applications, and thereby would be suitable as a container used in the present invention for holding biological cells of the living-cell biophoton radiator. The '117 publication describes a polymer-coated cell construction comprising a living cell and a polymer comprising at least one recurring unit represented by a formula selected from the group consisting of formula (I), formula (II), and formula (III)

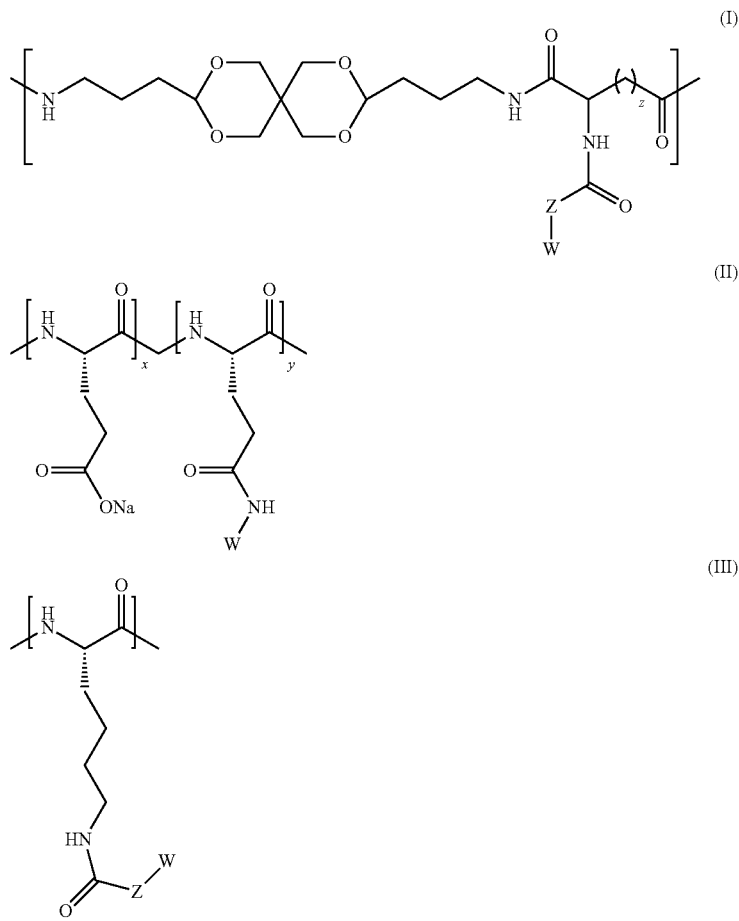

In one embodiment of the invention, the matrix 1310 would be a porous or semi-porous structure having pores 1350 in a membrane 1355 permitting biological and fluid connections from living cell layer 1320 and the organ to be made.

wherein n is 1 or 2; wherein x and y are each individually integers of from about 1 to about 500; wherein Z is an optional linker group comprising from about zero to about 20 carbon atoms, from about zero to about 5 oxygen atoms, from about zero to about five nitrogen atoms, from about zero to about 5 sulfur atoms, and from about zero to about five phosphorous atoms; and wherein each W is individually selected from the group consisting of biotin, a fatty acid, a fluorescent dye, an antibody, a peptide, a targeting ligand, a polysaccharide, and a negatively charged group, the polymer being non-covalently attached to at least a portion of the exterior of the living cell.

The '117 publication further describes a method for coating a living cell, comprising intermixing the living cell with a polymer which includes at least one recurring unit represented by a formula selected from formulas (I), (II), and (III) as described above, wherein the polymer is intermixed with the living cell in an amount effective to at least partially coat the exterior of the living cell.

Similar to that described in the '117 publication, in one embodiment of the present invention directed to the living cell biophoton radiator, a variety of diseased cells may be contained or carried by the polymer-coated cell construction noted above. These diseased cells may include cells exhibiting neurologic diseases (e.g. Parkinson's disease, multiple sclerosis), cardiovascular disease (myocardial ischemia, repair and regeneration of infarcted myocardium), hepatic disease (liver failure), diabetes, skin, and renal failure (chronic renal failure, acute renal failure), and cancer tissues.

In one embodiment of the invention, the target tissue to be treated with the living-cell biophoton radiator of this invention may be an organ such as heart, brain, kidney, skin, liver, muscle, spleen, lung, spinal cord and bone marrow. Tissues of this type or from these organs can be biopsied, cultured, and returned to the patient at the site of the disease. These cells may contain therapeutic agents to promote cell death or cell growth depending on the treatment under consideration. As these therapeutic agents work, biophoton emission radiates adjacent cells not contained in the polymeric coating, thereby inducing a change in the adjacent cells.

Conventionally, there are four basic issues for cell-based therapies. These are mobilization of the cells, homing to a target site, integration into the native tissue or organ and survival of the implanted cells. In one embodiment of this invention, the polymer coatings assist integration of cells of the living-cell biophoton radiator into native tissue and survival of implanted cells at least until biophoton radiation from the polymer encased cells can be used. By coating of the cells with the polymers, the cells may be protected in the blood for several hours. The polymer coated cells may also be protected from the immune response of the host. These coatings may protect the cell therapeutic while allowing passage of vital nutrients including oxygen.

The selection of cell type is a function of the disease which is being treated, the cell type being coated and forming part of the living-cell biophoton radiator. For example, skeletal myocytes would be injected into post-myocardial infarction scar tissue; neuronal cells would be administered to the brain of patients with Parkinson's Disease. Cell sources which may be used for the living-cell biophoton radiator of this invention include embryonic stem (ES) cells, adult stem cells, progenitor cells such as skeletal myoblasts, fetal and neonatal cardiomyocytes, and chord blood.

As an example of cells contained in the above noted polymer for the living-cell biophoton radiator of this invention, cardiovascular and lung tissues may also contain progenitor or stem cells that under the correct conditions could be induced to proliferate and repair cellular damage. For instance, recent findings suggest that a sub-population of fetal proliferative alveolar epithelial stem cells is present in adult lung. In addition, other tissues such as skin, liver, brain, and muscle have progenitor or stem cell populations that may provide additional sources of cells for cellular therapies.

For neovascularization of ischemic myocardium, endothelial progenitor cells for the living-cell biophoton radiator of this invention may be injected into the target area to promote new vessel growth. The cells are isolated from the mononuclear cell fraction of bone marrow or peripheral blood. The cells may be whole isolated cells or the cells may first be expanded in culture. Other examples for the living-cell biophoton radiator of this invention include treatment of skin disease with replacement grafts. Skeletal stem cell implantation may be used for bone regeneration. Chondrocytes may be used to repair joint cartilage. Acute and chronic renal failure may be treated with stem/progenitor cells using the living-cell biophoton radiator of this invention.

The cell source for the living-cell biophoton radiator of this invention may be either an autologous source or a non-autologous source. In some embodiments, the cells may be genetically modified. In cases where an adequate supply of cells is not possible from the patient due to the disease or other condition, non-autologous sources may be used. Non-autologous cells include allogeneic and xenogeneic cells. Non-autologous sources must overcome the natural host immunologic rejection processes. The polymer coating according to the embodiments provides protection from the host immune response.

The use of autologous cells generally involves obtaining the patient's own cells, expanding the cells in vitro in large quantities over several weeks, and reintroducing the cells in a site-specific manner.

A variety of means for administering cells for the living-cell biophoton radiators of this invention will be apparent to those of skill in the art. Such methods include injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the embodiments can be introduced into the subject at a desired location. In a preferred embodiment, cells are formulated for administration into a blood vessel via a catheter (where the term "catheter" is intended to include any of the various tube-like systems for delivery of substances to a blood vessel). The cells may be prepared for delivery in a variety of different forms. For example, the cells may be suspended in a solution or gel. Cells may be mixed with a pharmaceutically acceptable carrier or diluent in which the cells of the embodiments remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the polymer coated cells include but are not limited to systemic intracardiac, intracoronary, intravenous or intra-arterial injection and injection directly into the tissue at the intended site of activity. The preparation can be administered by any convenient route, for example by infusion or bolus injection and can be administered together with other biologically active agents. Administration is preferably systemic. Most preferably, the site of administration is close to or nearest the intended site of activity. In some embodiments, the polymer coated cells will migrate or home to the tissue or organ in need of treatment in response to chemotactic factors produced due to the injury without specific modification of the polymer coated cells for targeting.

Modifications of the polymer coating can provide for homing of the cells for the living-cell biophoton radiators of this invention to the target site. Protein targeting agents such as antibodies or proteins that bind to specific membrane sites may be used to target the polymer coated cells to the target organ or tissue. In some embodiments of the methods described herein, the polymer coated cells are modified prior to implantation into the individual so as to promote their targeting to tissue or organ in need of treatment. For example, the polymer may include an antibody which binds an antigen that is abundant at the target site, that is, at the site of the tissue or organ which is diseased or in need of treatment.

For example, monoclonal antibodies are known that specifically target cancer cells. Many of these are antibodies to growth factor receptors which are preferentially expressed on the surface of cancer cells. These include the humanized monoclonal antibody trastuzumab (Herceptin) which targets the HER-2/neu oncogene (Sato, et al. (2005) Int. J. Radiation Oncology Biol. Phys. vol. 61 (1): 203-211). The HER-2/neu oncogene is found in ovarian cancer, lung cancer, gastric cancer, oral squamous cell carcinoma, breast cancer, and esophageal cancer. BLCA-38 monoclonal antibody has been shown to target prostate and bladder cancer (Russell, et al. (2004) Cancer Immunol Immunother. vol. 53:995-1004). Other monoclonal antibodies are known and it is within the level of skill in the art to select a monoclonal antibody appropriate to the cancer or other disease or injury to be treated.

Migration of polymer coated cells for the living-cell biophoton radiators of this invention to target tissues may be enhanced by genetic modification, e.g., introduction of an exogenous nucleic acid encoding a homing molecule into the cells. Examples of homing molecules include receptors specific to the target tissue such as chemokine receptors, interleukin receptors, estrogen receptors, and integrin receptors.

In various embodiments, a receptor ligand such as transferrin or epidermal growth factor can be included in the polymer for homing to cancer cells. These ligands provide specific targeting to receptors on tumor cells. Thus, delivery of the coated cells is localized to the area in need of treatment for maximum effectiveness.

Another method of homing a cell such as a stem cell to an injured tissue is carried out by increasing the amount of an injury-associated polypeptide, e.g., a cytokine or adhesion protein, in the injured tissue. The method increases the number of stem cells in an area of injured tissue compared to the number of stem cells in the area in the absence of an exogenous injury-associated polypeptide or nucleic acid encoding such a polypeptide. For example, identification of injury-associated polypeptides, e.g., growth factors, activate endogenous mechanisms of repair in the heart such as proliferation and differentiation of cardiac progenitor cells. These effects can give rise to biophoton radiation supplementing healing in adjacent cells. The injured tissue is contacted with a nucleic acid encoding a protein such as a cytokine or adhesion protein. Alternatively, cells such as fibroblast cells expressing exogenous nucleic acid molecules encoding the cytokine or adhesion protein are introduced to the site of injury.

In one embodiment for the living-cell biophoton radiators of this invention, the cells optionally can contain an exogenous nucleic acid encoding a gene product, which increases endocrine action of the cell, e.g., a gene encoding a hormone, or a paracrine action of the cell. For example, stem cells are genetically modified to contain an exogenous nucleic acid encoding a bone morphogenetic factor and engrafted into bone, cartilage, or tooth tissue, e.g., to treat periodontitis.

The cells for the living-cell biophoton radiator of this invention, optionally also include nucleic acids encoding other biologically active or therapeutic proteins or polypeptides, e.g., angiogenic factors, extracellular matrix proteins, cytokines or growth factors. For example, cells to be engrafted into pancreatic tissue contain a nucleic acid(s) encoding insulin or insulin precursor molecules. The cells also optionally include nucleic acids encoding gene products that decrease transplant rejection, e.g., CTLA4Ig CD40 ligand, or decrease development of transplant arteriosclerosis, e.g., inducible nitric oxide synthase (iNOS).

Tissue specificity is a fundamental problem for gene therapy as proteins that are therapeutic in target cells also may be harmful to normal tissue. Thus, non cell-specific expression of a transgene has the potential for inducing metabolic and physiologic mechanisms that could result in pathology over the long term. Localized injections can provide certain degree of localized expression of the targeting vector, however, there may still be a spill over into the circulation which will affect other cells and organs. In some embodiments, transcriptionally targeted vectors may be used that can restrict the expression of the therapeutic proteins primarily to the target cells by the use of tissue-specific promoters.

Once the cells for the living-cell biophoton radiator of this invention are implanted, maintenance of the cells is dependent upon adequate nutrient and oxygen delivery to the implanted cells. The polymer cell coating according to the embodiments can allow for entry of oxygen and other nutrients into the coated cell.

In one embodiment of the present invention, a selected portion of cells in an organ can ne be subjected to stress. Accordingly, in this embodiment, a number of sources of stress can be used to introduce at least one of chemical and physical stresses on the selected portion of cells in the organ. For example, ultrasonic waves concentrated on a particular region of the organ could induce mechanical stresses (e.g., compression and/or elongation of the cell membranes) changing the transport of nutrients across the membrane, thereby stressing those cells to induce biophoton emission.

In another example, localized cooling of tissues in one part of an organ would produce stress in the cells to induce biophoton emission. In another example, localized heating of tissues in one part of an organ would produce stress in the cells undergoing the local heating to induce biophoton emission.

In this example, microwave hyperthermia treatment systems such as those described in U.S. Pat. No. 9,079,011 (the entire contents of which are incorporated herein by reference) could be used to locally heat tissues in one part of an organ, producing stress in those cells to induce biophoton emission. Conventionally, hyperthermia has been used to elevate the temperature of tissues for a variety of purposes including: (i) destroying tissues such as tumors by the application of heat, (ii) increasing the susceptibility of heated tissue to chemical or radiation therapy, and (iii) triggering heat activated or released drugs. It is generally known to use microwave electromagnetic radiation for hyperthermia treatment.

Figure 14:
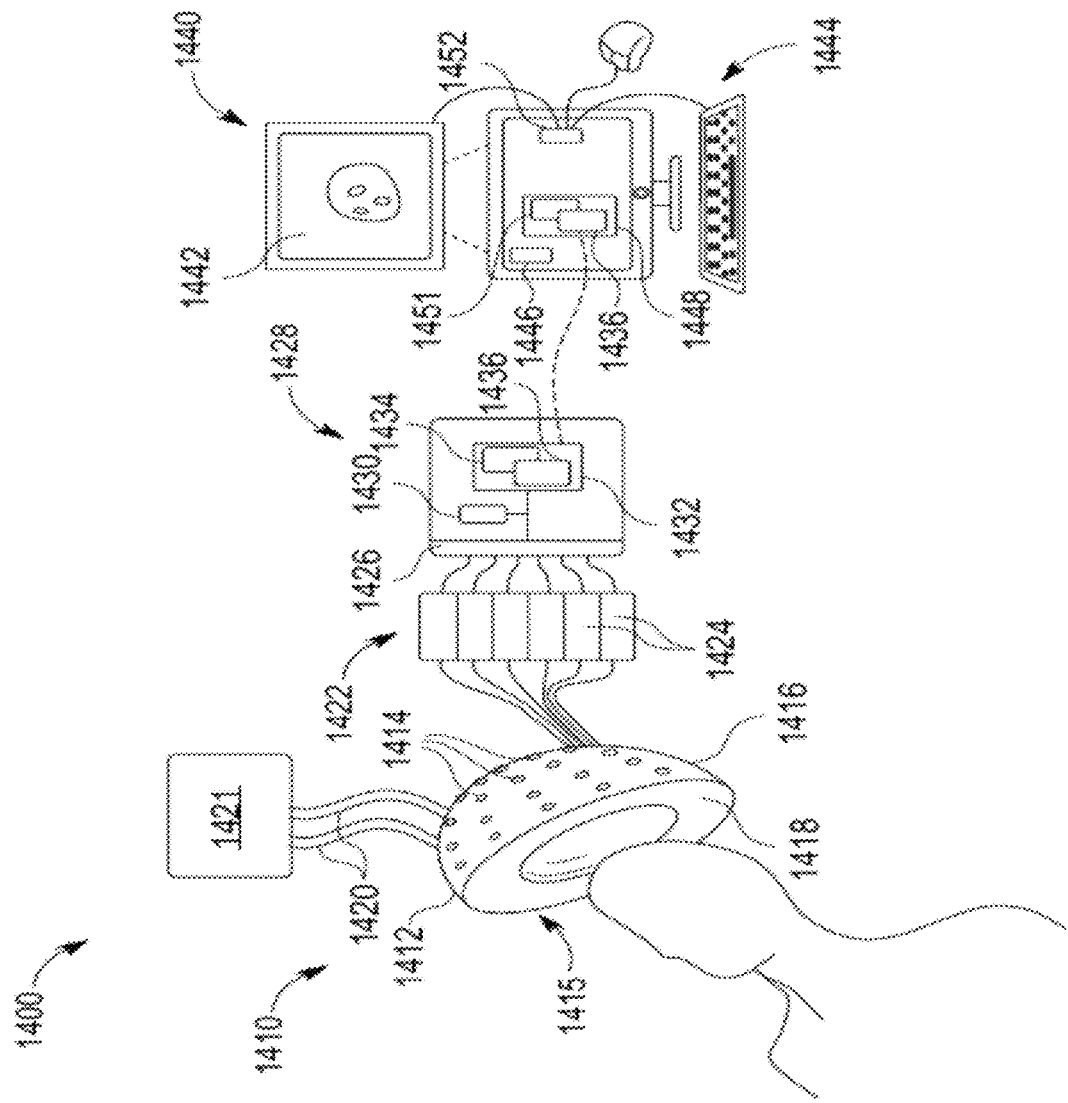
FIG. 14 is a depiction of a system 1400 of the present invention for application of microwave energy to a target region to locally heat the cells in the target region and thereby induce biophoton emission.

FIG. 14 is a depiction of a system 1400 of the present invention for application of microwave energy to a target region to locally heat the cells in the target region and thereby induce biophoton emission.

System 1400 of the present invention can have an antenna fixture 1412 supporting a plurality of antennas 1414 about a treatment volume 1415. In one embodiment, the treatment volume may be defined by a substantially hemispherical shell 1416 whose inner surface may contain a collar 1418 receiving and supporting the top of the patient's head. The collar may be filled with de-ionized water that may be circulated through connecting hoses 1420 with a cooler/pump 1421 providing skin cooling of at approximately 15 degrees centigrade of the patient's head to minimize surface heating of the skin by microwave energy from the antennas 14.

The antennas 1414 preferably direct microwave energy inward toward the treatment volume 1415 and may, for example, be microwave horns or patch antennas or other antennas of a type known in the art and are spaced to provide for substantially uniform separation of less than six centimeters.

Each antenna 1414 may be connected to a radiofrequency power source 1422 providing independent phase (phi) and amplitude (A) control of the radiofrequency power applied to the antenna. The radiofrequency power source 1422 may provide a separate radiofrequency amplifier/synthesizer 1424 for each antenna 1414 or may use a single radiofrequency power source with separate amplitude and phase shifters. In one embodiment, a set of discrete phases and amplitudes may be implemented in a switching fashion.

The radiofrequency power source 1422 may be controlled by a treatment controller 1428 via an interface board 1426, for example, providing a multiplexed A/D converter outputting phase and amplitude values from the treatment controller 1428. The treatment controller 1428 may include a processor 1430 communicating with a memory 1432 holding a stored program 1434 and treatment plan data 1436 describing a treatment schedule of changing phases and amplitudes of microwave frequency to be applied to the antennas 14 during treatment.

The treatment plan data 1436 may be developed on the treatment controller 1428 but also can be developed off-line on a separate workstation 1440 having a display 1442 for displaying treatment maps for physician input, as will be described, generated by a communicating standard desktop computer 1444 also having a processor 1446, a stored memory 1448 holding a treatment planning program 1451 and the treatment plan data 1436, the latter which may be transferred to treatment controller 1428. The desktop computer 1444 may also communicate with input devices 1450 by interface 1452 according to well understood techniques for physician input as will be described. It will be appreciated that the processing and data storage required by the present invention may be freely distributed among one or more processors and different types of computers according to well-understood techniques.

Microwaves provide a number of advantages including an ability to pass though some body structures such as the skull for treatment of the brain, and an ability to be focused to permit, for example, localized treatment of a tumor surrounded by tissue with reduced damage to the surrounding tissue. However, in this embodiment of the invention, localized and focused heating of selected portion of cells in an organ preferentially stops short of cell death, as dead cells would not emit biophoton radiation. Rather, the treatment plan stresses living cells in the targeted region to emit biophoton radiation.

In another example, stress could be applied by UV light at a non-lethal dose level using external sources of UV light "piped" into the subject (using for example the hollow cavity waveguide described above), or using phosphors under high energy or x-ray irradiation to produce internally within an organ localized stress.

Artificial Ex-Vivo Biophoton Radiators

On the market today is at least one commercial biophoton source, the BEP-AN15 made by Biolight, a Korean company. The Biolight source is reported to radiate ultra-weak photon emission, generating energy through modulation of visible light, and delivers the energy at a frequency similar to "biophotons by voluntary absorption."

Joohyeong Lee et al in "Oocyte maturation under a biophoton generator improves preimplantation development of pig embryos derived by parthenogenesis and somatic cell nuclear transfer." Korean J Vet Res (2017) 57 (2), pp. 89-95 (the entire contents of which are incorporated herein by reference) report the use of the artificial source of biophoton radiation noted above, the BEP-AN15 made by Biolight. Their work reported to shown that biophoton treatments during in vitro maturation improved the "developmental competence" of parthenogenesis and somatic cell nuclear transfer derived embryos. In their paper, Lee et al described that, in prior work, "leakage of a very small amount of photons from external sources has been shown to alter ultraweak photon emissions and cell-to-cell communication."

Accordingly, in one embodiment of the invention, an artificial ex vivo (or in vivo) biophoton generator is used to produce biophoton radiation or to affect ultraweak photon emissions and cell-to-cell communication.

One possible artificial source for biophoton radiation includes the device(s) described in U.S. Pat. No. 5,800,479 (the entire contents of which are incorporated herein by reference) owned by Biolight Patent Holding AB (Danderyd, SE). The '479 patent describes a device for an external medical treatment with the aid of light, including a light emitting element which is intended to lie against or be held close to a wound or sore on the body of an individual. The light emitting element included light emitting diodes or like devices and was constructed to (1) to emit infrared light in a first stage for a first predetermined length of time and thereafter to emit visible light in a second stage for a second predetermined length of time.

Another possible artificial source for biophoton radiation includes the device(s) described in U.S. Pat. No. 6,238,424 (the entire contents of which are incorporated herein by reference) owned by Biolight Patent Holding AB (Danderyd, SE). The '424 patent describes an apparatus for external medical treatment with light. A light-emitting device in the '424 patent is provided in close proximity to the body of an individual and that includes light-emitting diodes or corresponding elements that are adapted to emit monochromatic light of a first wavelength. The light emitting device is driven by a drive arrangement for causing the light-emitting device to emit the monochromatic light over a first predetermined time period in a first state, and thereafter emit selectively monochromatic light of a different wavelength than the first wavelength and over a second predetermined time period in a possible second state. The drive arrangement causes the light-emitting device to pulsate the emitted light in accordance with a predetermined pulse frequency or series of pulse frequencies over the respective time periods, and causes the light-emitting device to emit the pulsating light with a pulse length that lies within an interval of about 60% to about 90% of the time between respective start edges of two mutually sequential pulse.

Another possible artificial source for biophoton radiation includes the device(s) described in U.S. Pat. No. 6,537,303 (the entire contents of which are incorporated herein by reference) owned by Biolight Patent Holding AB (Danderyd, SE). The '303 patent describes a method for treatment of mammals by draining lymph along a lymph pathway within a mammal's body. In the '303 patent, an infrared-light-emitting device is used to emit pulsating infrared light at a low pulse repetition frequency. The light-emitting device is brought into contact with the body and is moved along a lymph pathway in a direction toward the lymphatic gland to which the pathway of the lymph vessel in question leads.

In one embodiment of the present invention, these artificial sources would be attenuated to produce weak or ultra-weak light emissions with duty cycles and wavelengths that mimic natural biophoton radiators. For example, UV emitting light emitting diodes could be used along with the visible and infrared light emitting diodes described above. UV light emitting diode are described in U.S. Pat. No. 8,907,320 (the entire contents of which are incorporated herein by reference) as including an n-type semiconductor layer, an active layer disposed on the n-type semiconductor layer, a p-type semiconductor layer disposed on the active layer and formed of p-type AlGaN, and a p-type graphene layer disposed on the p-type semiconductor layer and formed of graphene doped with a p-type dopant.

In one embodiment of the invention, a target cell to be treated is analyzed first to ascertain its biophoton emission characteristics. If the target cell is a known cancer strain, representative cancer lines could be analyzed. Alternatively, biopsies could remove small regions of the cancerous tumor. These representative or biopsied samples could be subject to cell death and the natural biophoton radiation could be observed. Once characteristics (e.g., wavelengths, duty cycle, total emittance) are known or inferred or estimated, the configuration and driving of the LED array elements can be used to mimic the natural biophoton spectra.

From the literature results noted above, in one embodiment of the invention, the mimic spectra could have one or more of the following characteristics:
  emissions in 190-250 nm wavelength range;
  emissions in the 330-340 nm wavelength range;
  a combination of emissions in the 190-250 nm and in the 330-340 nm wavelength ranges;
  emissions across the range of 250 nm to 600 nm;
  emissions in the infrared range;
  a duration of emission in short bursts of approximately a millisecond at a repetition frequency of 10 to 100 Hz; and
  a range of photon flux from a few to a 1000 photons/(sec·cm$^2$) or higher.

These characteristics are merely exemplary and would be designed in one embodiment as discussed above to mimic the natural biophoton spectra of a target cell to be treated.

Light from the external biophoton radiators would be coupled to the diseased or malignant site using the biophoton bypass noted above.

In Vivo Point of Use Biophoton Generator

The present invention can use any desired energy converter, including, but not limited to, organic fluorescent molecules or inorganic particles capable of fluorescence and/or phosphorescence having crystalline, polycrystalline or amorphous micro-structures.

Organic fluorescent compounds with high quantum yield include, but are not limited to:
  naphthalene, pyrene, perylene, anthracene, phenanthrene, p-terphenyl, p-quaterphenyl, trans-stilbene, tetraphenylbutadiene, distyrylbenzene, 2,5-diphenyloxazole, 4-methyl-7-diethylaminocoumarin, 2-phenyl-5-(4-biphenyl)-1,3,4-oxadiazole, 3-phenylcarbostyryl, 1,3,5-triphenyl-2-pyrazoline, 1,8-naphthoylene-1',2'-benzimidazole, 4-amino-n-phenyl-naphthalimide.

Inorganic fluorescent and/or phosphorescent materials span a wide variety of materials. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, $ZnS$, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4:Pr^{3+}$. Examples further include the alkali earth chalcogenide phosphors which are in turn exemplified by the following non-inclusive list: $MgS:Eu^{3+}$, $CaS:Mn^{2+}$, $CaS:Cu$, $CaS:Sb$, $CaS:Ce^{3+}$, $CaS:Eu^{2+}$, $CaS:Eu^{2+}Ce^{3+}$, $CaS:Sm^{3+}$, $CaS:Pb^{2+}$, $CaO:Mn^{2+}$, $CaO:Pb^{2+}$.

Further examples include the ZnS type phosphors that encompass various derivatives: ZnS:Cu,Al(Cl), ZnS:Cl(Al), ZnS:Cu,I(Cl), ZnS:Cu, ZnS:Cu,In.

Also included are the compound IIIb-Vb phosphors which include the group Mb and Vb elements of the periodic table. These semiconductors include BN, BP, BSb, AlN, AlP, AlAs, AlSb, GaN, GaP, GaAs, GaSb, InN, InP, InAs, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn,O, GaP:NN, Gap:N and GaP, which emit colors Red, Yellow, Green and Pure Green respectively.

The materials can further include such materials as GaAs with compositional variation of the following sort: $In_{1-y}(Ga_{1-x}AlO_x)_yP$.

Also included is silicon carbide SiC, which has commercial relevancy as a luminescent platform in blue light emitting diodes. These include the polytypes 3C-SiC 6H-SiC, 4H-SiC with donors such as N and Al and acceptors such as Ga and B.

Further examples include multiband luminescent materials include, but not limited to, the following compositions (Sr, Ca, Ba)$_5$(PO$_4$)$_3$Cl:Eu$^{2+}$, BaMg$_2$Al$_{16}$O$_{27}$:Eu$^{2+}$, CeMgAl$_{11}$O$_{19}$:Ce$^{3+}$:Tb$^{3+}$, LaPO$_4$:Ce$^{3+}$:Tb$^{3+}$, GdMgB$_5$O$_{10}$:Ce$_3$:Tb$^{3+}$, Y$_2$O$_3$:Eu$^{3+}$, (Ba,Ca,Mg)$_5$(PO$_4$)$_3$Cl:Eu$^{2+}$, 2SrO$_{0.84}$P2O50.16B2O3:Eu$^{2+}$, Sr$_4$Al$_{14}$O$_{25}$Eu$^{2+}$.

Materials typically used for fluorescent high pressure mercury discharge lamps are also included. These can be excited with X-Ray and are exemplified by way of family designation as follows: Phosphates (Sr, M)(PO$_4$)$_2$:Sn$^{2+}$, Mg or Zn activator, Germanate 4MgO·GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^+$, Halo-Silicate $Sr_2Si_3O_8 \cdot 2SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: $3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$, $Sr_{10}(PO_4)_6Cl_2:Eu^{2+}$, $(Sr,Ca)_{10}(PO_4)_6O_2:Eu^{2+}$, $(Sr, Ca)_{10}(PO_4)_6 \cdot nB_2O_3:Eu^{3+}$, $(Sr, Ca, Mg)_{10}(PO_4)_6Cl_2:Eu^{2+}$. The phosphate phosphors include, but are not limited to: $Sr_2P_2O_7:Sn^{2+}$, $(Sr,Mg)_3(PO_4)_2:Sn^{2+}$, $Ca_3(PO_4)_2 \cdot Sn^{2+}$, $Ca_3(PO_4)_2:Tl^+$, $(Ca,Zn)_3(PO_4)_2:Tl^+$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3 \cdot 0.2SiO_2 \cdot 0.9P_2O_5:Ce^{3+} \cdot Tb^{3+}$, $BaO \cdot TiO_2 \cdot P_2O_5$. The silicate phosphors $Zn_2SiO_4:Mn^{2+}$, $CaSiO_3:Pb^{2+}/Mn^{2+}$, $(Ba, Sr, Mg) \cdot 3Si_2O_7:Pb^{2+}$, $BaSi_2O_5:Pb^{2+}$, $Sr_2Si_3O_8 \cdot 2SrCl_2:Eu^{2+}$, $Ba_3MgSi_2O_8:Eu^{2+}$, $(Sr,Ba)Al_2Si_2O_8:Eu^{2+}$.

The aluminate phosphors include, but are not limited to: $LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include: $Cd_2B_2O_5:Mn^{2+}$, $SrB_4O_7:F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include, but are not limited to: $CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO \cdot As_2O_5:Mn^{2+}$, $3.5Mg \cdot 0.5MgF_2 \cdot GeO_2:Mn^{4+}$.

The activators to the various doped phosphors include, but are not limited to: $Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$. The luminescence center $Tl^+$ is used with a chemical composition such as: $(Ca,Zn)_3(PO_4)_2:Tl^+$, $Ca_3(PO_4)_2:Tl^+$. The luminescence center $Mn^{2+}$ is used with chemical compositions such as $MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2 \cdot Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$. The luminescence center Sn2+ is used with chemical compositions such as: $Sr_2P_2O_7:Sn^{21}$, $(Sr,Mg)_3(PO_4)_2:Sn^{2+}$. The luminescence center $Eu^{2+}$ is used with chemical compositions such as: $SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$. The luminescence center $Pb^{2+}$ is used with chemical compositions such as: $(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ is used with chemical compositions such as: $3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$.

The luminescence center $Tb^{3+}$ is used with chemical compositions such as: $CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$. The luminescence center $Eu^{3+}$ is used with chemical compositions such as: $Y_2O_3:Eu^{3+}$, $Y(V,P)O_4:Eu^{3+}$. The luminescence center $Dy^{3+}$ is used with chemical compositions such as: $YVO_4:Dy^{3+}$. The luminescence center $Fe^{3+}$ is used with chemical compositions such as: $LiAlO_2:Fe^{3+}$. The luminescence center $Mn^{4+}$ is used with chemical compositions such as: $6MgO \cdot As_2O_5:Mn^{4+}$, $3.5MgO0.5MgF_2 \cdot GeO_2:Mn^{4+}$. The luminescence center $Ce^{3+}$ is used with chemical compositions such as: $Ca_2MgSi_2O_7:Ce^{3+}$ and $Y_2SiO_5:Ce^{3+}$. The luminescence center $WO_4^{2-}$ is used with chemical compositions such as: $CaWO_4$, $(Ca,Pb)WO_4$, $MgWO_4$. The luminescence center $TiO_4^{4-}$ is used with chemical compositions such as: $BaO \cdot TiO_2 \cdot P_2O_5$. Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr: Tb^{3+}$ | 38.92 keV |
| $LaOBr: Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| $ZnS:Ag$ | 9.66 keV |
| $(Zn, Cd)S:Ag$ | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors would mimic the natural biophoton spectra of a target cell to be treated, similar to that described above where exemplary characteristics could include:

emissions in 190-250 nm wavelength range;
emissions in the 330-340 nm wavelength range;
a combination of emissions in the 190-250 nm and in the 330-340 nm wavelength ranges;
emissions across the range of 250 nm to 600 nm;
emissions in the infrared range;
a duration of emission in short bursts of approximately a millisecond at a repetition frequency of 10 to 100 Hz; and
a range of photon flux from a few to a 1000 photons/(sec·cm2) or higher.

Thus, in one embodiment of the invention, ultraviolet and visible emissions can be used for the inventive in vivo biophoton source.

Figure 15:
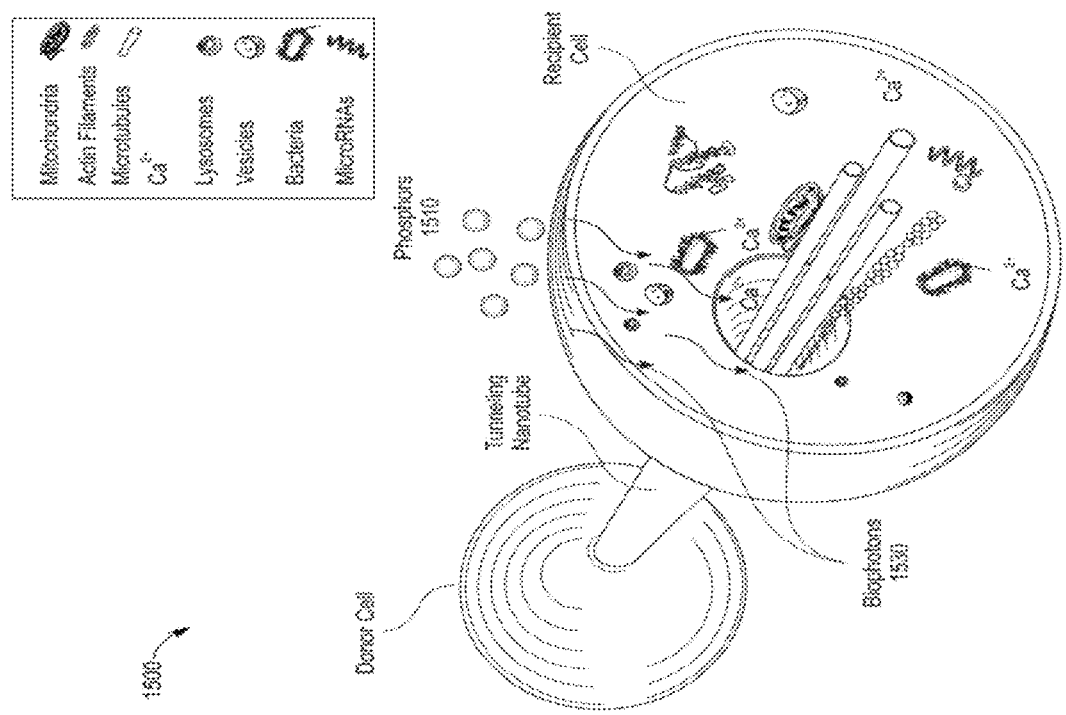
FIG. 15 is a depiction of an in vivo biophoton source 1500 according to one embodiment of the present invention.

FIG. 15 is a depiction of an in vivo biophoton source 1500 where phosphors 1510 in proximity to the cells are excited by high energy such as x-rays or e-beams to generate biophoton radiation 1530 mimicking the characteristics known or measured from the target cells for their biophoton radiation.

In the depiction of FIG. 15, the biophotons 1530 can penetrate the cell and interact with the interior components of the cell such as the mitochondria and bacteria in the cell. In one embodiment of the invention, the biophotons 1530 can be transmitted to the donor cell by transmission through the tunneling nanotube joining the cells. A more thorough discussion of tunneling nanotubes is given later. In one embodiment of the invention, the biophoton radiation may change the chemical and charge transport along the tunneling nanotubes by photoionization events which place charge on the interior walls of the tunneling nanotubes.

Accordingly, in one embodiment of the invention, the photon flux from the inventive biophoton sources can be, but is not necessarily, a low photon flux source (in the range of single photons and therefore not operating as a classical light wavefront subject to scattering and absorption). Higher flux may be used with the expectation that beneficial results would still follow, especially under conditions where the natural absorption/scatter in the subject would result in appropriate photon fluxes within the treatment region.

With the in vivo point of use biophoton generator, the duty cycle of the x-ray unit would determine the duty cycle of the biophoton radiation produced, the phosphor selection or combination of phosphors would determine the wavelength emission characteristics, and external coatings on the phosphors would serve to attenuate the level of light emitted at the target site.

Moreover, since the level of light emission for biophotons is low, the x-ray dose to the patient for a biophoton radiation treatment can be significantly lower than that for other radiation treatments.

In this embodiment, a downconverting energy modulation agent (e.g., a down converting phosphor) can comprise inorganic particulates selected from the group consisting of: metal oxides; metal sulfides; doped metal oxides; and mixed metal chalcogenides. In one aspect of the invention, the downconverting material can comprise at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS and alkali lead silicate including compositions of $SiO_2$, $B_2O_3$, $Na_2O$, $K_2O$, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration. U.S. Pat. Appl. Publ. Nos. 2017/0157418 and 2017/0239489 (the entire contents of both are incorporated herein by reference) provided details of these and other suitable phosphors.

In one aspect of the invention, the downconverting energy modulation agent can comprise materials such as ZnSeS:Cu, Ag, Ce, Tb; CaS:Ce, Sm; $La_2O_2S$:Tb; $Y_2O_2S$:Tb; $Gd_2O_2S$: Pr, Ce, F; $LaPO_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include $ZnSe_xS_y$:Cu, Ag, Ce, Tb, where the following x, y values and intermediate values are acceptable: x:y; respectively 0:1; 0.1:0.9; 0.2:0.8; 0.3:0.7; 0.4:0.6; 0.5: 0.5; 0.6:0.4; 0.7:0.3; 0.8:0.2; 0.9:0.1; and 1.0:0.0.

In other aspects of the invention, the downconverting energy modulation agent can be materials such as sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3Tb$), gadolinium oxysulphide:europium ($Gd_2O_2S$:Eu), lanthanum oxysulphide:europium ($La_2O_2S$: Eu), and gadolinium oxysulphide:promethium, cerium, fluorine ($Gd_2O_2S$:Pr,Ce,F), $YPO_4$:Nd, $LaPO_4$:Pr, (Ca,Mg)$SO_4$: Pb, $YBO_3$:Pr, $Y_2SiO_5$:Pr, $Y_2Si_2O_7$:Pr, $SrLi_2SiO_4$:Pr,Na, and $CaLi_2SiO_4$:Pr.

In other aspects of the invention, the downconverting energy modulation agent can be near-infrared (NIR) downconversion (DC) phosphors such as $KSrPO_4$:$Eu^{2+}$, $Pr^{3+}$, or $NaGdF_4$:Eu or $Zn_2SiO_4$:$Tb^{3+}$, $Yb^{3+}$ or β-$NaGdF_4$ co-doped with $Ce^{3+}$ and $Tb^{3+}$ ions or $Gd_2O_2S$:Tm or $BaYF_5$:$Eu^{3+}$ or other down converters which emit NIR from visible or UV light exposure (as in a cascade from x-ray to UV to NIR) or which emit NIR directly after x-ray or e-beam exposure.

In one aspect of the invention, an up converting energy modulation agent can also be used such as at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

In one aspect of the invention, the energy modulation agents can be used singly or in combination with other down converting or up converting materials.

TABLE 1 shows a list of other suitable phosphors:

TABLE 1

| # | Phosphor | Emission Spectrum Peak Emission (nm) | X-ray Absorption Emiss Eff (%) | X-ray Absorption Eff (Z) | X-ray Absorption K-edge (keV) | Microstructure Specific Gravity | Microstructure Crystal Structure | Hygroscopic |
|---|---|---|---|---|---|---|---|---|
| 1 | BaFCl:$Eu^{2+}$ | 380 | 13 | 49.3 | 37.38 | 4.7 | Tetragonal | N |
| 2 | $BaSO_4$–:$Eu^{2+}$ | 390 | 6 | 45.5 | 37.38 | 4.5 | Rhombic | N |
| 3 | LaOBr:$Tm^{3+}$ | 360, 460 | 14 | 49.3 | 38.92 | 6.3 | Tetragonal | N |
| 4 | $YTaO_4$ | 337 | | 59.8 | 67.42 | 7.5 | Monolithic | N |
| 5 | $YTaO_4$:Nb (*) | 410 | 11 | 59.8 | 67.42 | 7.5 | Monolithic | N |
| 6 | $CaWO_4$ | 420 | 5 | 61.8 | 69.48 | 6.1 | Tetragonal | N |
| 7 | LaOBr:$Tb^{3+}$ | 420 | 20 | 49.3 | 38.92 | 6.3 | Tetragonal | N |
| 8 | $Y_2O_2S$:$Tb^{3+}$ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn,Cd)S:Ag | 530 | 19 | 38.4 | 9.66/26.7 | 4.8 | Hexgonal | N |
| 11 | $Gd_2O_2S$:$Tb^{3+}$ | 545 | 13 | 59.5 | 50.22 | 7.3 | Hexgonal | N |
| 12 | $La_2O_2S$:$Tb^{3+}$ | 545 | 12.5 | 52.6 | 38.92 | 6.5 | Hexgonal | N |

In one embodiment of the invention, besides the $YTaO_4$, noted above, other energy modulation agents can include phosphors were obtained from the following sources. "Ruby Red" obtained from Voltarc, Masonlite & Kulka, Orange, Conn., and referred to as "Neo Ruby"; "Flamingo Red" obtained from EGL Lighting. Berkeley Heights, N.J, and referred to as "Flamingo"; "Green" obtained from EGL Lighting, Berkeley Heights, N.J. and referred to as "Tropic Green"; "Orange" obtained from Voltarc, Masonlite & Kulka. Orange, Conn, and referred to as "Majestic Orange"; "Yellow" obtained from Voltarc. Masonlite & Kulka, Orange. Conn., and referred to as "Clear Bright Yellow." The "BP" phosphors are shown in detail below in TABLE 2:

TABLE 2

| Code | Phosphor Material Color | Emission Spectrum Peak Emission (nm) | Emiss Eff (%) | Eff (Z) | X-Ray Absorption K-edge (keV) | Density g/cc Specific Gravity | Xtal Crystal Structure | Hygroscopic |
|---|---|---|---|---|---|---|---|---|
| BP1 | CaWO4:Pb | 425 | | | | | | N |
| BP2 | Y2SiO5:Ce | 410 | | | | | | N |
| BP3 | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF-1 | 460 | | | | | | |
| BP5 | BASF-2 | 490 | | | | | | |
| BP6 | YTaO4:Nb (*) | 410 | 11 | 59.8 | 67.42 | 7.5 | Monolithic | N |
| BP6-C | YTaO4:Nb (*) | | | | | | | |
| BP7-C | LaOBr:Tm3+ (coated) | 360, 460 | 14 | 49.3 | 38.92 | 6.3 | Tetragonal | N |
| BP8-C | LaF3:Ce | 280 | | | | | | |
| BP9 | Y2O3 | 365 | | | | | | |
| BP-10 | BaSO4-:Eu2+ (coated) | 390 | 6 | 45.5 | 37.38 | 4.5 | Rhombic | N |
| BP10-C | BaSO4-:Eu2+ (coated) | 390 | 6 | 45.5 | 37.38 | 4.5 | Rhombic | N |
| BP11 | LaOCl:Tm | | | | | | | |
| BP12 | Y2O2S:Tm | | | | | | | |
| BP13 | BaSi2O5:Pb2+ | 350 | | | | | | N |
| | SrB6O10:Pb | 360 | | | | | | N |
| | CaI:Na (Coated) | 338 | | | | | | Y |
| | Gd2O2S:Tm | Blue to Green | | | | | | Y |

The "BP" phosphors are available from PhosphorTech Corporation of Kennesaw, Ga., from BASF Corporation, or from Phosphor Technology Ltd, Norton Park, Norton Road Stevenage, Herts, SG1 2BB, England.

Other useful energy modulation agents include semiconductor materials including for example $TiO_2$, ZnO, and $Fe_2O_3$ which are biocompatible, and CdTe and CdSe which would preferably be encapsulated because of their expected toxicity. Other useful energy modulation agents include ZnS, CaS, BaS, SrS and $Y_2O_3$ which are less toxic. Other suitable energy modulation agents which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles. $Yb^{3+}$ doped $CsMnCl_3$ and $RbMnCl_3$. $BaFBr:Eu^{2+}$ nanoparticles, cesium iodide, bismuth germanate, cadmium tungstate, and CsBr doped with divalent Eu. Table 4 below provides a list of various useful energy modulation agents In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

As a non-limiting list, the following are also suitable energy modulation agents: $Y_2O_3ZnS$; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb $ZnS:Tb^{3+}$, $Er^{3+}$; $ZnS:Tb^{3+}$; $Y_2O_3:Tb^{3+}$, $Y_2O_3:Tb^{3+}$, $Er^{3+}$; $ZnS:Mn^{2+}$; $ZnS:Mn,Er^{3+}$, $CaWO_4$, $YaTO_4$, $YaTO_4:Nb$, $BaSO_4:Eu$, $La_2O_2S:Tb$, $BaSi_2O_5:Pb$, NaI(Tl), CsI(Tl), CsI(Na), CsI(pure), CsF, KI(Tl), LiI(Eu), $BaF_2$, CaF, $CaF_2(Eu)$, ZnS(Ag), $CaWO_4$, $CdWO_4$, YAG(Ce) ($Y_3Al_5O_{12}(Ce)$), BGO bismuth germanate, GSO gadolinium oxyorthosilicate, LSO lutetium oxyorthosilicate. $LaCl_3(Ce)$. $LaBr_3(Ce)$. $LaPO_4$; Ce, Tb (doped). $Zn_2SiO_4:Mn$ with Mn doped between 0.05-10%, and $YTaO_4$.

TABLE 3

| Item # | Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|---|
| 24 | Zn3(PO4)2:Tl+ | 310 | | | | | | N |
| 33 | BaF2 | 310 | | | | | | Slightly |
| 30 | CsI | 315 | | | | | | N |
| 23 | Ca3(PO4)2:Tl+ | 330 | | | | | | N |
| 4 | YTaO4 | 337 | | 59.8 | 67.42 | 7.5 | Monolithic | N |
| 38 | CsI:Na | 338 | | | | | | Y |
| 14 | BaSi2O5:Pb2+ | 350 | | | | | | N |
| 27 | Borosilicate | 350 | | | | | | N |
| 34 | LaCl3(Ce) | 350 | | | | | | Y |
| 16 | SrB4O7F:Eu2+ | 360 | | | | | | N |

TABLE 3-continued

| Item # | Phosphor | Emission Spectrum Peak Emission Color (nm) | Emiss Eff (%) | Eff (Z) | X-Ray Absorption K-edge (keV) | Specific Gravity | Crystal Structure | Hygroscopic |
|---|---|---|---|---|---|---|---|---|
| 20 | RbBr:Tl+ | 360 | | | | | | ? |
| 15 | (Ba, Sr, Mg)3Si2O7:Pb2+ | 370 | | | | | | N |
| 17 | YAlO3:Ce3+ | 370 | | | | | | N |
| 37 | BC-422 | 370 | | | | | Organic | ? |
| 1 | BaFCl:Eu2+ | 380 | 13 | 49.3 | 37.38 | 4.7 | Tetragonal | N |
| 2 | BaSO4:Eu2+ | 390 | 6 | 45.5 | 37.38 | 4.5 | Rhombic | N |
| 19 | BaFBr:Eu2+ | 390 | | | | | | ? |
| 36 | BC-420 | 391 | | | | | Organic | ? |
| 35 | BC-414 | 392 | | | | | Organic | ? |
| 25 | SrMgP2O7:Eu2+ | 394 | | | | | | N |
| 18 | BaBr2:Eu2+ | 400 | | | | | | N |
| 22 | (Sr, Ba)Al2Sl2O8:Eu2+ | 400 | | | | | | N |
| 5 | YTaO4:Nb (*) | 410 | 11 | 59.8 | 67.42 | 7.5 | Monolithic | N |
| 21 | Y2SiO5:Ce3+ | 410 | | | | | | N |
| 6 | CaWO4 | 420 | 5 | 61.8 | 69.48 | 6.1 | Tetragonal | N |
| 7 | LaOBr:Tb3+ | 420 | 20 | 49.3 | 38.92 | 6.3 | Tetragonal | N |
| 8 | Y2O2S:Tb3+ | 420 | 18 | 34.9 | 17.04 | 4.9 | Hexgonal | N |
| 13 | Lu2SiO5:Ce3+ | 420 | | | | | | N |
| 26 | LuL8Y0.2SiO5:Ce | 420 | | | | | | N |
| 9 | ZnS:Ag | 450 | 17 | 26.7 | 9.66 | 3.9 | Hexgonal | N |
| 29 | CdWO4 | 475 | | | | | | Slightly |
| 28 | Bi4Ge3O12 (BGO) | 480 | | | | | | N |
| 10 | (Zn, Cd)S:Ag | 530 | 19 | 38.4 | 9.66/26.7 | 4.8 | Hexgonal | N |
| 11 | Gd2O2S:Tb3+ | 545 | 13 | 59.5 | 50.22 | 7.2 | Hexgonal | N |
| 12 | La2O2S:Tb3+ | 545 | 12.5 | 52.6 | 38.92 | 6.5 | Hexgonal | N |
| 31 | Y3AlSO12 (Ce) | 550 | | | | | | N |
| 3 | LaOBr:Tm3+ | 360, 460 | 14 | 49.3 | 38.92 | 6.3 | Tetragonal | N |
| 32 | CaF2(Eu) | 435/300 | | | | | | N |

In one embodiment, phosphors used in the invention as energy modulation agents can include phosphor particles, ionic doped phosphor particles, single crystal or poly-crystalline powders, single crystal or poly-crystalline monoliths, scintillator particles, a metallic shell encapsulating at least a fraction of a surface of the phosphors, a semiconductor shell encapsulating at least a fraction of a surface of the phosphors, and an insulator shell encapsulating at least a fraction of a surface of the phosphors, and phosphors of a distributed particle size.

In one embodiment of this invention, the phosphors for the in vivo point of use biophoton generator can be coated with the '117 publication polymers noted above for homing of the phosphors for the in vivo point of use biophoton generator to the target site.

With the capability to produce in vivo or deliver in vivo, specified wavelengths of light, the present invention may utilize a hybrid process in which both biophoton radiation and "activation" radiation are available for treatment. An activation radiation would be radiation of a specific wavelength to activate a photoactivatable drug such as psoralen or coumarin.

The selection of activatable pharmaceutical agents depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms. An activatable agent may be a small molecule; a biological molecule such as a protein, a nucleic acid or lipid; a supramolecular assembly; a nanoparticle; or any other molecular entity having a pharmaceutical activity once activated.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one embodiment, the activatable pharmaceutical agent is capable of chemically binding to the DNA or mitochondria at a therapeutically effective amount. In this embodiment, the activatable pharmaceutical agent, preferably a photoactivatable agent, is exposed to an activating energy emitted from an energy modulation agent (e.g. a phosphor), which, in turn receives energy from an initiation energy source (e.g. an x-ray source).

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and naphthoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

In one embodiment of the invention, a hybrid treatment is used. In one embodiment of the hybrid treatment, a control region inside a patient containing phosphors is exposed to x-rays, from which ultraviolet light and visible light of a spectrum to activate one of the activatable agents noted above. The photoactivated agents induce apoptosis, causing the cancer cells to emit naturally biophoton radiation. Simultaneously, phosphors mimicking the natural biophoton radiation are exposed with the same x-rays and emit also biophoton radiation.

In one embodiment of the invention, since cell death induced by the photoactivated agents occurs over a longer duration than the x-ray exposure, the simultaneous generation in situ of the biophoton radiation can be viewed as "signaling" adjacent cells not affected by the photoactivated agent of the cell death event.

In one embodiment of the invention, the photoactivated x-ray treatment can proceed the generation of biophotons in vivo by first dosing the diseased site with the phosphors for photoactivation and then later dosing the diseased site with phosphors for biophoton generation. Since the level of light for biophotons is low, the x-ray dose to the patient for biophoton radiation can be significantly lower than that for activation of the photoactivated agents.

Biophoton Stimulator

In one embodiment of the invention, a light source is used, not to mimic the natural biophoton spectra of a target cell to be treated, but rather to stimulate natural biophoton radiation. It is known that the entire range of visible light can stimulate a living system to emit a biophoton signal. It is also known that non-damaging ultraviolet radiation also stimulates living systems to emit biophoton signals. For example, it has been observed that light in the 300 to 450 nm wavelength range can induce ultraweak photon emission. The strongest emission observed occurred when the living cells were stimulated at 350 nm. In another example, "white light" also induced biophoton emission.

Thus, in this embodiment, the phosphors and combinations noted above for the in vivo biphoton generator embodiment can be remixed/reselected such the phosphor selection under x-ray or other high energy source irradiation, would emit light from the phosphors which would stimulate living tissue in a subject to generate its own natural biphoton radiation.

In one embodiment of the present invention, stimulated emission coherence is achieved because the living cells themselves (under stimulation) as in nature will generate coherent emissions. For example, without chemical toxins or high energy radiation, one can induce cancer cells (by exposure to "white light" or 350 nm light) to emit biophotons as if they themselves are undergoing apoptosis. The neighboring cancer cells would then respond to this "signaling" and die, and during the stress leading to death rebroadcast actual biophoton signals associated with cell death to their neighbors. Since the "rebroadcast" is from living cells, natural coherence would be obtained.

Coherence is considered advantageous if, at a distance from the coherent emission, constructive interference could promote a biological, physical, or chemical reaction. Coherence is considered advantageous if, at a distance from the coherent emission, long-range dynamic order is to be promoted and/or controlled. For example, electrically polar structures of biomolecules that contain electric charges can generate electromagnetic fields when they vibrate, thereby producing an endogenous electromagnetic field of the organism with coherent modes. In relation to this, the majority of proteins are electrically polar structures typically immersed in water, a highly polar liquid. When metabolic energy exceeds a critical level, these polar structures engage in a steady state of nonlinear vibration, and energy is stored in a highly ordered manner, as a coherent excitation. This order expresses itself as a long range phase correlation. The order in biological systems is considered not just spatial, but dynamic, and can include long-range coherence within the entire organism.

The cytoskeleton of living cells include microtubules, tree-like structures, throughout the cytoplasm. These microtubules are electrically polar structures that can be excited and are expected to generate an endogenous coherent electric field that could have a dominant effect directing the transport of molecules and electrons throughout the cell. Moreover, connective tissue with an extracellular matrix composed of collagen that interconnects cells throughout the body is another possible network for the collective bioplasma state.

Others have predicted resonant frequencies of the biological field in the microwave region of the electromagnetic spectrum between 100-1000 GHz. Thus, in another embodiment, the biophoton stimulator of the invention is a microwave source operating in this frequency range to "drive resonance" or otherwise influence the behavior of this bioplasma collective system.

Target Treatments

Exemplary conditions, disorders or diseases which may be treated with the present invention can include, but are not limited to, cancer, autoimmune diseases, cardiac ablasion (e.g., cardiac arrhythmiand atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthrisis, joint conditions, lymph node conditions, and cognitive and behavioral conditions.

Although not intending to be bound by any particular theory or be otherwise limited in any way, the following theoretical discussion of scientific principles and definitions are provided to help the reader gain an understanding and appreciation of the present invention.

As used here, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmi- and atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthritis, joint conditions, and lymph node conditions.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

The inventive treatments may be used in one embodiment to induce an auto vaccine effect for malignant cells, including those in solid tumors. To the extent that any rapidly dividing cells or stem cells may be damaged by a systemic treatment, then it may be preferable to direct any signals, chemical agents, biological agents, or blocking agents directly into the first region, preventing damage directly to normal, healthy cells or stem cells in the second (or treatment) region can be induced by activating a chemiluminescent, phosphorescent or bioluminescent compound with an appropriate activation energy, either outside the subject or inside the subject.

Candidates might be 1) in vivo stimulated regrowth of organ tissue, 2) generation of alternative pathways for nerve cell to nerve cell communication perhaps by promotion of TNTs, and 3) anti-inflammatory responses.

Assisted Photobiomodulation

Photobiomodulation, which is also traditionally known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

In one embodiment of this invention, wavelengths of biophoton radiation can be applied to or emitted from within a first region can for example, aid tissue regeneration, resolve inflammation, relieve pain and boost the immune system. Observed biological and physiological effects to be expected include changes in cell membrane permeability, and up-regulation and down-regulation of adenosine triphosphate and nitric oxide. All of these changes in the biological material of the first region can, according to one embodiment of the invention, be responsible for inducing corresponding changes in a second or treatment region.

Clinical applications of photobiomodulation suitable for causing or initiating changes in the biological material of the first or target region of this invention include, for example, treating soft tissue and bone injuries, chronic pain, wound healing and nerve and sensory regeneration/restoration, and possibly even resolving viral and bacterial infections, treating neurological and psychiatric diseases (e.g., epilepsy and Parkinson's disease) (e.g., Zhang F., et al., Nature, 446: 617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One other suitable clinical application is the treatment of inflammation, where the anti-inflammatory effect of location-and-dose-specific laser irradiation produces similar outcomes as NSAIDs, but without the potentially harmful side-effects (Bjordal J M, Couppé C, Chow R T, Tunér J, Ljunggren E A (2003). "A systematic review of low level laser therapy with location-specific doses for pain from chronic joint disorders". The Australian journal of physiotherapy 49(2):107-16). Accordingly, in one embodiment of the present invention, biophoton irradiation from the biophoton radiation sources noted above can be applied to the biological material of the first or target region, and thereby inducing changes in the second or target region which may treat in the second region soft tissue and bone injuries, chronic pain, wound healing and nerve and sensory regeneration/restoration, and possibly even resolve viral and bacterial infections, and treat neurological and psychiatric diseases.

An NIR light treatment has been shown to prevent cell death (apoptosis) in cultured neurons (brain) cells (Wong-Reiley M T, et al., J B C, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)). Accordingly, in one embodiment of the present invention, biophoton radiation from the biophoton sources noted above and NIR light can be applied or internally generated in the biological material of the first or target region, and thereby inducing changes in the second or target region to address the disorders noted above.

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells viabsorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)). Accordingly, in one embodiment of the present invention, low power laser therapy along with biophoton radiation from the biophoton sources noted above can be applied or internally generated in the biological material of the first or target region, and thereby inducing changes in the second or target region to address the disorders noted above.

When photoacceptors absorb photons, electronic excitation followed by photochemical reactions occurring from lower excitation states (first singlet and triplet) takes place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu, T I, et al., (1998). The Science of Low Power Laser Therapy. Gordon and Breach Sci. Publ., London). Accordingly, in one embodiment of the present invention, the absorption of photons in the biological material of the first or target region (e.g., from the biophoton sources noted above) can contribute to changes in the first region, thereby inducing changes in the second or target region to alter the pathways noted above.

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes). Accordingly, in one embodiment of the present invention, the absorption of photons in the biological material of the first or target region (e.g., from the biophoton sources noted above) can induce changes in the first region, thereby inducing changes in the second or target region to affect the respiratory chain as noted above Far red and NIR radiation have been shown to promote wound healing, e.g., infected, ischemic, and hypoxic wounds (Wong-Reley, W T T, J B C, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Another clinical application of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vasc. Interv. Radiol., 18(6):811 (2007)). When the laser is slowly withdrawn, heat is applied to the vein walls, causing the vein to permanently close and disappear. Accordingly, in one embodiment of the present invention, the absorption of red and IR photons in the biological material of the first or target region along with biophoton radiation can cause changes in the first region, thereby inducing changes in the second or target region to promote wound healing, e.g., infected, ischemic, and hypoxic wounds and/or help repair soft tissue, noted above.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated, that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations. Accordingly, in one embodiment of the present invention, the absorption of NIR in the biological material of the first or target region coupled to brain tissue along with biophoton radiation the biophoton sources noted above can directly cause changes in the first region, thereby inducing changes in the second or target region in the actual brain tissue for control of brain cell activity, as noted above.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE). Accordingly, in one embodiment of the present invention, the absorption of He—Ne laser radiation in the biological material of the first or target region coupled to cancerous tissue along with biophoton radiation the biophoton sources noted above can cause changes in the first region, thereby inducing changes in the second or target region in the actual cancerous tissue.

Assisted Photostimulation

One photostimulation technique involves chemical modification of ion channels and receptors to render them light-responsive. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself. Here, the phosphor configurations of the invention can be programmed or instructed or configured to deliver light for direct control of neuronal activity.

In living organisms, scientists have been able to cause worms, C. elegans, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. The mice resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients, but they don't know precisely why. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another embodiment of the present invention is the stimulation of neural communications. Because neurons communicate by generating patterns of signals-sometimes on and sometimes off like the 0s and 1s of binary computer code-flashing blue and yellow lights in these patterns could compel neurons to emit messages that correspond to real neural instructions. The present invention can be used to test and tune sophisticated neuron behaviors. The ability to artificially stimulate neural signals, such as movement instructions using the present invention may allow doctors to bridge blockages in damaged spinal columns, perhaps restoring some function to the limbs of paralyzed patients.

Accordingly, in one embodiment of the present invention, the absorption of photons designed for photostimulation in the biological material of the first or target region along with biophoton radiation from one of the biophoton sources noted above can cause or induce changes in the first region via photostimulation, thereby inducing changes in the second or target region for stimulation and/or control of neural communication and other neuron activities.

In Vivo or In Vitro Internal Light Sources

In one embodiment, sources of internal light can be used in this invention to stimulate bioactivity (as discussed above and elsewhere) and or to simulate natural biophoton sources. In one embodiment, the sources of internal light for use in this invention can include persistent after-glow phosphor materials emitting light in the visible to near ultraviolet and ultraviolet range. These sources of internal light can be either sources inside a patient or inside an artificial construct containing biological material to be exposed to the light where the sources comprise up converting or down converting phosphors or fluorescent agents, and preferably down converting phosphors or fluorescent agents which, upon exposure to x-rays (or other high energy waves or particles) emit ultraviolet and/or visible light at the known emission bands of these phosphors and fluorescent agents. These sources of internal light can be those described above for the in vivo point of use biophoton generator and the biophoton stimulator.

In one embodiment, Eu-doped strontium aluminate is used as an internal light source in which deep UV light or x-ray or electron beams "charge" the photoluminescence such that these phosphors can, for example, be charged outside a patient and then injected into a target or diseased site where UV photons would be emitted. In another embodiment, gadolinium strontium magnesium aluminate is used as an internal light source in which deep UV light or x-ray or electron beams "charge" the photoluminescence such that these phosphors can, for example, be charged outside a patient and then injected into a target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful internal light sources for this invention, making note of emission spectra between 300 nm and 320 nm for a $Sr(Al,Mg)_{12}O_{19}$:Gd phosphor and two 312 nm line emitting phosphors, $YMgB_5O_{10}$:Gd, Ce and $YMgB_5O_{10}$:Gd, Ce, Pr WO2016200349 (the entire contents of which are incorporated herein by reference) describes long lasting yellowishgreen emitting phosphorescent pigments in the strontium aluminate (SrAl2O4) system, which could serve as internal light sources in the present invention. WO 2016200348 (the entire contents of which are incorporated herein by reference) describes long lasting bluish-green emitting phosphorescent pigments in the strontium aluminate (Sr4Al14O25) system, which could serve as internal light sources in the present invention. Xiong et al in "Recent advances in ultraviolet persistent phosphors," Optical Materials X 2 (2019) (the entire contents of which are incorporated herein by reference) describes a number of ultraviolet persistent phosphors that could serve as internal light sources in the present invention. The table below provides a listing of such persistent phosphors:

| | | |
|---|---|---|
| $SrO:Pb^{2+}$ | 390 | >1 h |
| $CaAl_2O_4:Ce^{3+}$ $Tb^{3+}$ | 400 | >10 h |
| $CaAl_2O_4:Ce^{3+}$ $Tb^{3+}$ | 413 | >10 h |
| $Sr_2Al_2SiO_2:Ce^{3+}$ | 400 | several minutes |
| $SrZrO_3$ | 395 | <1000 s |
| $BaZrO_3:Mg^{2+}$ | 400 | >2400 s |
| $SrZrO_3:Pr^{3+}$ | 356 | |
| $CdSiO_3:Bi^{3+}$ | 360 | |
| $CdSiO_3:Bi^{3+}$ $Dy^{3+}$ | 360 | |
| $CdSiO_3:Bi^{3+}$ $Gd^{3+}$ | 344 | >6 h |
| $Sr_2MgGe_2O_7:Pb^{2+}$ | 370 | >12 h |
| $NaLuGeO_4:Bi^{3+}$ $Eu^{3+}$ | 400 | >63 h |
| $CaZnGe_2O_6: Bi^{3+}$ | 300-700 | >12 h |
| $Cs_2NaYF_6:Pr^{3+}$ | 250 | >2 h |

In one embodiment, the phosphor described by Xiong et al as $CaAl_2O_4:Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site (or at a site to be treated) and then exposed to x-rays producing a persistent internal light source.

In another embodiment, a combined electromagnetic energy harvester molecule could be used as an internal light source, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. In another embodiment, a Stokes shift of an emitting source or a series of emitting sources arranged in a cascade is selected to convert a shorter wavelength energy, such as X-rays, to a longer wavelength fluorescence emission such an optical or UV-A.

In one embodiment, a lanthanide chelate capable of intense luminescence is used as an internal light source. In another embodiment, a biocompatible, endogenous fluorophore emitter can be used as an internal light source.

In one embodiment, the internal light source of this invention can include visible and UV-light emitting bioluminescent materials. In one embodiment, bioluminescent materials such as coelenterate-type luciferin analogues could be used including amide monoanion known to emit at 480 nm and oxyluciferin known to emit at 395 nm.

In another embodiment of the invention, mechano-luminescent materials can be used as internal light sources.

Mechano-luminescent materials convert ultrasonic or mechanical energy (such as vibrations naturally existing on an article such as motor or vibrations from driven by transducers) into visible light. Here, for example, the mechano-luminescent materials would be placed in a vicinity of a diseased site or at a site or sites to be treated with internally generated light.

Within the context of the present invention, the phrase "in a vicinity of", and variations thereof, includes near, adjacent, or within/inside a diseased site or site or sites to be treated.

Various mechano-luminescent materials suitable for the present invention include $ZnS:Mn^{2+}$, $SrAl_2O_4:Eu^{2+}$, ZnS: Cu, $SrAMgSi_2O_7:Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$ (x<¼), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ (1≤n≤2), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

In one embodiment, a europium-holmium co-doped strontium aluminate can be used as a mechano-luminescent material (i.e., an internal light source). The europium-holmium co-doped strontium aluminate and the other mechano-luminescent materials convert sonic or acoustic energy into photon emissions which may be placed in a vicinity of a diseased site or at a site or sites to be treated with internally generated light.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention, such composites made of a piezoelectric material and an electroluminescent material, hereinafter "composite mechanoluminescent emitters," provides a structure that, upon stimulation with mechanical or vibrational energy such as from an acoustic or ultrasonic transducer, emit light to a diseased site or at a site or sites to be treated with internally generated light.

The present invention in various embodiments can utilize organic fluorescent molecules or inorganic particles capable or fluorescence and phosphorescence having crystalline, polycrystalline or amorphous micro-structures for the internal light sources of this invention generating light at a diseased site or at a site or sites to be treated with internally generated light.

The list of inorganic molecules that can be used for the electroluminescence and phosphorescent materials described below include but is not limited to the following inorganic electroluminescent phosphor materials:

SrS:Ce
CaGa$_2$S$_4$:Ce$^{3+}$
SrS:Cu$^+$
CaS:Pb$^{2+}$
BaAl$_2$S$_4$:Eu$^{2+}$
ZnS:Tb$^{3+}$
ZnMgS:Mn$^{2+}$
SrGa$_2$S$_4$:Eu$^{2+}$
CaAl$_2$S$_4$:Eu$^{2+}$
BaAl$_2$S$_4$:Eu$^{2+}$
ZnS:Mn$^{2+}$
MgGa$_2$O$_4$:Eu$^{3+}$
(Ca, Sr)Y$_2$S$_4$:Eu$^{2+}$
BaAl$_2$S$_4$:Eu$^{2+}$

Organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole,
3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation and can be used for the internal light sources of this invention generating light at a diseased site or at a site or sites to be treated with internally generated light.

Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

CaF$_2$, ZnF$_2$, KMgF$_3$, ZnGa$_2$O$_4$, ZnAl$_2$O$_4$, Zn$_2$SiO$_4$, Zn$_2$GeO$_4$, Ca$_5$(PO$_4$)$_3$F, Sr$_5$(PO$_4$)$_3$F, CaSiO$_3$, MgSiO$_3$, ZnS, MgGa$_2$O$_4$, LaAl$_{11}$O$_{18}$, Zn$_2$SiO$_4$, Ca$_5$(PO$_4$)$_3$F, Mg$_4$Ta$_2$O$_9$, CaF$_2$, LiAl$_5$O$_8$, LiAlO$_2$, CaPO$_3$, AlF$_3$.

Further included are alkali earth chalcogenide phosphors which are in turn exemplified by the following non-inclusive list:

MgS:Eu$^{3+}$, CaS:Mn$^{2+}$, CaS:Cu, CaS:Sb, CaS:Ce$^{3+}$, CaS:Eu$^{2+}$, CaS:Eu$^{2+}$Ce$^3$, CaS:SM$^{3+}$, CaS:Pb$^{2+}$, CaO:Mn$^{2+}$, CaO:Pb$^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group Mb and Vb elements of the periodic table are suitable phosphors. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1-y(Ga1-xAlx)yP (provides a simple example).

Silicon Carbide SiC as a luminescent platform has commercial relevancy for blue light emitting diodes and could be used as an internal light source if appropriately powered from the outside. The SiC luminescent platform could include the polytypes 3C-SiC, 6H-SiC, 4H-SiC with donors such as N and Al and acceptors such as Ga and B.

Multiband luminescent materials suitable for converter materials include for example the following compositions:

(Sr, Ca, Ba)$_5$(PO$_4$)$_3$Cl:Eu$^{2+}$, BaMg$_2$Al$_{16}$O$_{27}$·Eu$^{2+}$, CeMgAl$_{11}$O$_{19}$·Ce$^{3+}$·Tb$^{3+}$, LaPO$_4$:Ce$^{3+}$:Tb$^{3+}$, GdMgB$_5$O$_{10}$:Ce$^{3+}$:Tb$^{3+}$, Y$_2$O$_3$:Eu$^{3+}$, (Ba,Ca,Mg)$_5$(PO$_4$)$_3$Cl:Eu$^{2+}$, 2SrO$_{0.84}$P$_2$O$_5$.16B$_2$O$_3$:Eu$^{2+}$, Sr$_4$Al$_{14}$O$_{25}$:Eu$^{2+}$.

Other materials suitable for the internal light sources of this invention generating light at a diseased site or at a site or sites to be treated with internally generated light include those materials typically used for fluorescent high pressure mercury discharge lamps but which can be excited with X-Ray and are exemplified by way of family designation as follows:

Phosphates (Sr, M)(PO$_4$)$_2$:Sn$^{2+}$, Mg or Zn activator, Germanate 4MgO·GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^+$, Halo-Silicate Sr2Si3O$_8$.2SrCl$_2$:Eu$^{2+}$, Aluminate (Ba,Mg)$_2$Al$_{16}$O$_{24}$:Eu$^{2+}$, (Ba, Mg)$_2$Al$_{16}$O$_{24}$:Eu$^{2+}$,Mn$^{2+}$, Y$_2$O$_3$Al$_2$O$_3$:Tb$^{3+}$.

Another grouping of materials suitable for converter materials for the internal light source include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

3Ca$_3$(PO$_4$)$_2$·Ca(F,Cl)$_2$:Sb$^{3+}$, 3Ca$_3$(PO$_4$)$_2$·Ca(F,Cl)$_2$:Sb$^{3+}$/Mn$^{2+}$, Sr$_{10}$(PO$_4$)$_6$Cl$_2$:Eu$^{2+}$, (Sr,Ca)$_{10}$(PO$_4$)$_6$Cl$_2$:Eu$^{2+}$, (Sr,Ca)$_{10}$(PO$_4$)$_6$·nB$_2$O$_3$:Eu$^{3+}$, (Sr, Ca,Mg)$_{10}$(PO$_4$)$_6$Cl$_2$:Eu$^{2+}$. The phosphate phosphors include by way of illustration Sr$_2$P$_2$O$_7$:Sn$^{2+}$, (Sr,Mg)$_3$(PO$_4$)$_2$:Sn$^{2+}$, Ca$_3$(PO$_4$)$_2$·Sn$^{2+}$, Ca$_3$(PO$_4$)$_2$:Tl$^+$, (Ca,Zn)$_3$(PO$_4$)$_2$:Tl$^+$, Sr$_2$P$_2$O$_7$:Eu$^{2+}$, SrMgP$_2$O$_7$:Eu$^{2+}$, Sr$_3$(PO$_4$)$_2$:Eu$^{2+}$, LaPO$_4$:Ce$^{3+}$, La$_2$O$_3$.0.2SiO$_2$.0.9P$_2$O$_5$:Ce$^{3+}$Tb$^{3+}$, BaO·TiO$_2$·P$_2$O$_5$. The silicate phosphors Zn$_2$SiO$_4$:Mn$^{2+}$, CaSiO$_3$:Pb$^{2+}$/Mn$^{2+}$, (Ba, Sr, Mg)·3Si$_2$O$_7$:Pb$^{2+}$, BaSi$_2$O$_5$:Pb$^{2+}$, Sr$_2$Si$_3$O$_8$·2SrCl$_2$:Eu$^{2+}$, Ba$_3$MgSi$_2$O$_8$:Eu$^{2+}$, (Sr,Ba)Al$_2$Si$_2$O$_8$:Eu$^{2+}$.

The aluminate phosphors include:

LiAlO$_2$:Fe$^{3+}$, BaAl$_8$O$_{13}$:Eu$^{2+}$, BaMg$_2$Al$_{16}$O$_{27}$:Eu$^{2+}$, BaMg$_2$Al$_{16}$O$_{27}$:Eu$^{2+}$/Mn$^{2+}$, Sr$_4$Al$_{14}$O$_{25}$:Eu$^{2+}$, CeMgAl$_{11}$O$_{19}$:Ce$^{3+}$/Tb$^{3+}$.

The borate phosphors include:

Cd$_2$B$_2$O$_5$:Mn$^{2+}$, SrB$_4$O$_7$F:Eu$^{2+}$, GdMgB$_5$O$_{10}$:Ce$^{3+}$/Tb$^{3+}$, GdMgB$_5$O$_{10}$:Ce$^{3+}$/Mn$^{3+}$, GdMgB$_5$O$_{10}$:Ce$^{3+}$/Tb$^{3+}$/Mn$^{2+}$.

The tungstate phosphors include:

$CaWO_4$, $(Ca,Pb)WO_4$, $MgWO_4$. Other phosphors $Y_2O_3$:$Eu^{3+}$, $Y(V,P)O_4$:$Eu^{2+}$, $YVO_4$:$Dy^{3+}$, $MgGa_2O_4$:$Mn^{2+}$, $6MgOAs_2O_5$:$Mn^{2+}$, $3.5MgO \cdot 0.5MgF_2 \cdot GeO_2$:$Mn^{4+}$.

Activators of relevance to the various doped phosphors include the following list:

$Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center Tl+ can be used with a chemical composition such as:

$(Ca,Zn)_3(PO_4)_2$:$Tl^+$, $Ca_3(PO_4)_2$:$Tl^+$.

Similarly, the luminescence center Mn2+ can be used with chemical compositions such as $MgGa_2O_4$:$Mn^{2+}$, $BaMg_2Al_{16}O_{27}$:$Eu^{2+}/Mn^{2+}$, $Zn_2SiO_4$:$Mn^{2+}$, $3Ca_3(PO_4)_2 \cdot Ca(F,Cl)_2$:$Sb^{2+}/Mn^{2+}$, $CaSiO_3$:$Pb^{2+}/Mn^{2+}/Mn^{2+}$, $Cd_2B_2O_5$:$Mn^{2+}$, $CdB_2O_5$:$Mn^{2+}$, $GdMgB_5O_{10}$:$Ce^{3+}/Mn^{2+}$, $GdMgB_5O_{10}$:$Ce^{3+}/Tb^{3+}/Mn^2$.

Further, the luminescence center $Sn^{2+}$ can be used with chemical compositions such as:

$Sr_2P_2O_7$:$Sn^{2+}$, $(Sr,Mg)_3(PO_4)_2$:$Sn^{2+}$.

The luminescence center $Eu^{2+}$ can also be used with chemical compositions such as:

$SrB_4O_7F$:$Eu^{2+}$, $(Sr,Ba)Al_2Si_2O_8$:$Eu^{2+}$, $Sr_3(PO_4)_2$:$Eu^{2+}$, $Sr_2P_2O_7$:$Eu^{2+}$, $Ba_3MgSi_2O_8$:$Eu^{2+}$, $Sr_{10}(PO_4)_6Cl_2$:$Eu^{2+}$, $BaMg_2Al_{16}O_{27}$:$Eu^{2+}/Mn^{2+}$, $(Sr,Ca)_{10}(PO_4)_6Cl_2$:$Eu^{2+}$.

The luminescence center $Pb^{2+}$ can be used with chemical compositions such as:

$(Ba,Mg,Zn)_3Si_2O_7$:$Pb^{2+}$, $BaSi_2O_5 \cdot Pb^{2+}$, $(Ba,Sr)_3Si_2O_7$:$Pb^{2+}$.

The luminescence center $Sb^{2+}$ can be used with chemical compositions such as:

$3Ca_3(PO_4)_2 \cdot Ca(F,Cl)_2$:$Sb^{3+}$, $3Ca_3(PO_4)_2$—$Ca(F,Cl)_2$:$Sb^{3+}/Mn^{2+}$.

The luminescence center Tb3+ can be used with chemical compositions such as:

$CeMgAl_{11}O_{19}$:$Ce^{3+}/Tb^{3+}$, $LaPO_4$:$Ce^3/Tb^{3+}$, $Y_2SiO_5$:$Ce^{3+}/Tb^{3+}$, $GdMgB_5O_{10}$:$Ce^{3+}/Tb^{3+}$.

The luminescence center $Eu^{3+}$ can be used with chemical compositions such as:

$Y_2O_3$:$Eu^{3+}$, $Y(V,P)O_4$:$Eu^{3+}$.

The luminescence center $Dy^{3+}$ can be used with chemical compositions such as:

$YVO_4$:$Dy^{3+}$.

The luminescence center $Fe^3$ can be used with chemical compositions such as:

$Li\ AlO_2$:$Fe^{3+}$.

The luminescence center $Mn^{4+}$ can be used with chemical compositions such as:

$6MgO \cdot As_2O_5$:$Mn^{4+}$, $3.5MgO0.5MgF_2 \cdot GeO_2$:$Mn^{4+}$.

The luminescence center $Ce^{3+}$ can be used with chemical compositions such as:

$Ca_2MgSi_2O_7$:$Ce^{3+}$ and $Y_2SiO_5$:$Ce^{3+}$.

The luminescence center $WO_4^{2-}$ can be used with chemical compositions such as:

$CaWO_4$, $(Ca,Pb)WO_4$, $MgWO_4$.

The luminescence center $TiO_4^{4-}$ can be used with chemical compositions such as:

$BaO \cdot TiO_2 \cdot P_2O_5$.

In various embodiments of this invention, the phosphor chemistry utilized in x-ray excitations can be used for the internal light sources of this invention generating light at a diseased site or at a site or sites to be treated with internally generated light.

Of particular interest is the k-edge of these phosphors. Low energy excitation can lead to intense luminescence in materials with low k-edge. Some of these chemistries and the corresponding k-edge are included as follows:

| | |
|---|---|
| $BaFCl$:$Eu^{2+}$ | 37.38 keV |
| $BaSO_4$:$Eu^{2+}$ | 37.38 keV |
| $CaWO_4$ | 69.48 keV |
| $Gd_2O_2S$:$Tb^{3+}$ | 50.22 keV |
| $LaOBr$:$Tb^{3+}$ | 38.92 keV |
| $LaOBr$:$Tm^{3+}$ | 38.92 keV |
| $La_2O_2S$:$Tb^{3+}$ | 38.92 keV |
| $Y_2O_2S$:$Tb^{3+}$ | 17.04 keV |
| $YTaO_4$ | 67.42 keV |
| $YTaO_4$:Nb | 67.42 keV |
| $ZnS$:Ag | 9.66 keV |
| $(Zn, Cd)S$:Ag | 9.66/26.7 keV |

In one embodiment of this invention, light from these materials (excited for example by high energy particles including x-rays, gamma rays, protons, and electrons) can have their emissions act as the internal light sources of this invention generating light at a diseased site or at a site or sites to be treated with internally generated light.

Various materials used for the electro-luminescence can be used for the internal light sources of this invention generating light at a diseased site or at a site or sites to be treated with internally generated light. The electro-luminescence materials can include but are not limited to:

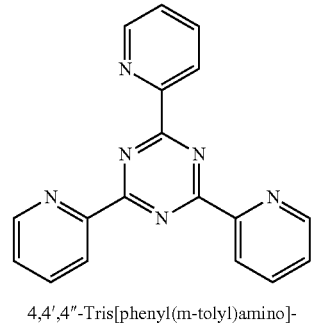

4,4′,4″-Tris[phenyl(m-tolyl)amino]-triphenylamine (m-MTDATA)
N,N′-Bis(3-methylphenyl)-N,N′-diphenylbenzidine (TPD)
4,4′,4″-Tris[phenyl(m-tolyl)amino]-triphenylamine (m-MTDATA)
N,N′-Bis(3-methylphenyl)-N,N′-diphenylbenzidine (TPD)
Tris-(8-hydroxyquinoline)-aluminum
2,4,6-Tris(2-pyridyl)-s-triazine (TPT)

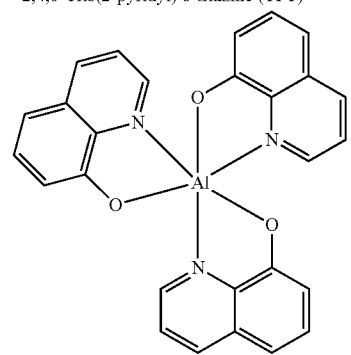

2,2′,2″-(1,3,5-Benzinetriyl)-tris(1-phenyl-1-H-benzimidazole) Alq

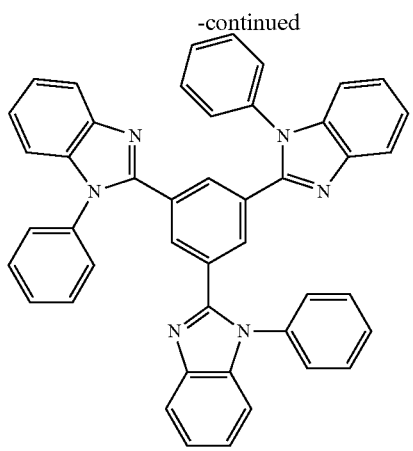

2,2′,2″-(1,3,5-Benzinetriyl)-tris(1-phenyl-1-H-benzimidazole) TPBI

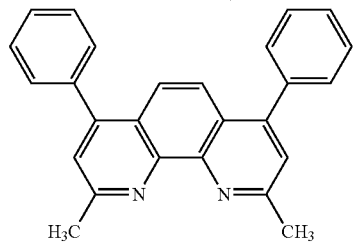

2,9-Dimethyl-4,7-diphenyl-1,10-phenanthroline, BCP2,9-Dimethyl-4,7-diphenyl-1,10-phenanthroline, BCP Stimulated Regeneration and Phototreatment In one embodiment of this invention, the photon radiation generated by the sources described above such as the in vivo point of use biophoton generator, the biophoton stimulator, and the in vivo and in vitro internal light sources described above (and the fluorescing materials and phosphors described herein) can be used as a source of light to stimulate bioactivity (as discussed above and elsewhere) and/or to simulate natural biophoton sources.

In prior work entitled "Conjugated polymers optically regulate the fate of endothelial colony-forming cells, conjugated polymers were used with visible light excitation to gain optical control of cell fate" by Lodola et al. in Science Advances 27 Sep. 2019: Vol. 5, no. 9, the entire contents of which are incorporated herein by reference, endothelial progenitor cells (EPCs) and, in particular, endothelial colony-forming cells (ECFCs) were evaluated for optical regulation. ECFCs can be mobilized from the bone marrow and vascular stem cell niche to reconstruct a vascular network destroyed by an ischemic insult and to restore local blood perfusion. ECFCs can be harvested from peripheral blood, and are known to display robust clonogenic potential, exhibit tube-forming capacity in vitro, and generate vessel-like structures in vivo.

This work by Lodola et al. demonstrated that polymer-mediated optical excitation during the first steps of ECFC growth could lead to a robust enhancement of both proliferation and tubulogenesis through the optical modulation of the $Ca^{2+}$-permeable transient receptor potential vanilloid 1 (TRPV1) channel and NF-κB-mediated gene expression. The material used for light absorption and phototransduction was regioregular poly(3-hexyl-thiophene) (P3HT), a thiophene-based conjugated polymer which acted as an exogenous, light-responsive actuator. This work by Lodola et al. used polymer thin films (approximate thickness, 150 nm) deposited by spin coating on top of polished glass substrates. Both polymer-coated and glass substrates have been thermally sterilized (120° C., 2 hours), coated with fibronectin, and, lastly, used as light-sensitive and control cell culturing substrates, respectively. ECFCs were seeded on top of polymer coated glass substrates.

This work by Lodola et al. provided optical excitation by a light-emitting diode (LED) source, with maximum emission wavelength at 525 nm, incident from the substrate side. A protocol based on 30-ms excitation pulses, followed by a 70-ms dark condition, at a photoexcitation density of 40 mW/cm$^2$ was used to minimize heating. The whole protocol is continuously repeated for a minimum of 4 up to 36 hours, depending on the type of functional assay, at controlled temperature (37° C.) and $CO_2$ levels (5%). This work found that optical excitation, properly mediated by biocompatible polymer substrates, positively affects ECFC fate by spatially and temporally selective activation of the TRPV1 channel which has been shown to be expressed and drive angiogenesis in human ECFCs.

More significantly, this work postulated that the P3HT polymer upon interaction with light induced an excited state of P3HT resulting in charged oxygen state $O_2^-$, subsequently producing hydrogen peroxide, triggering intracellular reactive oxygen species (ROS) enhancement.

Lesions have been treated with target light-sensitive molecules called photosensitizers (PSs). When irradiated with light, PSs generate reactive oxygen species (ROS) which very rapidly react with any nearby biomolecule and can eventually kill cells through apoptosis or necrosis. The technique, called chromophore-assisted light inactivation (CALI), has been used for the treatment of precancerous lesions and superficial tumors.

In one embodiment of this invention, the stimulated activity generated by the light internally generated in the medium to be treated promotes the formation of new blood vessels using at least one of ultraviolet and/or visible light emission into the medium to be treated. Here, the internal light sources generate the ultraviolet and/or the visible light which exposes a photosensitive material (for example the P3HT polymer noted above) contained within or in a vicinity of natural or artificial tissue cells containing endothelial progenitor cells. In one embodiment, the ultraviolet and/or the visible light generated within the photosensitive material generates reactive oxygen species which can promote an angiogenesis process within the natural or artificial tissue cells containing the endothelial progenitor cells. In one embodiment, the light internally generated in the medium is generated by phosphorescence or fluorescence of light emitting materials disposed within the photosensitive material (for example the P3HT polymer noted above) when the light emitting materials are exposed to x-rays.

In one embodiment, the phosphorescence or fluorescence light emitting materials are disposed in a biocompatible polymer that is not necessarily photosensitive. The biocompatible material is coated or else is to be located in vicinity to endothelial progenitor cells. X-ray exposure of this composite biocompatible polymer generates UV light emission from the phosphorescence or fluorescence light emitting materials which exits the composite biocompatible polymer and generates ROS in the medium about the endothelial progenitor cells, thereby stimulating blood vessel growth.

In other prior work, Andres Garcia of the Georgia Institute of Technology and his team have made blood vessels grow by shining light on skin. In this prior work, entitled "Light-triggered in vivo activation of adhesive peptides regulates cell adhesion, inflammation and vascularization of biomaterials, published in Nature Materials volume 14, pages 352-360 (2015), the entire contents of which are incorporated herein by reference, a RGB peptide (used to signal cells to grow on new tissues) and a photo-responsive blocker were impregnated into a water-based gel, or hydrogel, which was later activated by UV light from an external source. The UV light released the blocker and cell growth was observed. However, the depth of penetration of UV light from an external source limits the utility of this approach.

In one embodiment of the present invention, a water-based gel, or hydrogel, is impregnated with a RGB peptide and a material of one of the internal light sources described above such that activation for example by x-ray exposure generates within the hydrogel the ultraviolet and/or the visible light. When UV light from the internal light source in the hydrogel is generated, the UV light causes the blocker to be released, and the RGB peptide to become active.

In one embodiment, the hydrogel with the impregnated RGB peptide, the blocker, and the internal light source material is implanted into a patient and exposed to x-ray flux which generates within the hydrogel UV light which causes the blocker to be released, and the RGB peptide to become active within the patient.

In another embodiment, the hydrogel with the impregnated RGB peptide, the blocker, the internal light source material, and a vascular endothelial growth factor protein that stimulates the growth of new blood vessels is implanted into a patient and exposed to x-ray flux which generates within the hydrogel UV light which causes the blocker to be released, and the RGB peptide and the vascular endothelial growth factor protein to become active.

Thus, in one embodiment of the invention, there is provided a method for regenerative medicine using internal light sources within artificial or in vivo living cells to regrow cells of an organ in a patient in which light for the internal light sources stimulates or otherwise promote s the regrowth/regeneration of cells of the organ, for example where angiogenesis (blood vessel regrowth occurs as an example due to generation of reactive oxygen species or for example the removal of blocking proteins preventing endothelial progenitor cells from generating new cells.

In other prior work, Berkowitz et al. and his research team at John Hopkins in an article entitled "Melanopsin mediates light-dependent relaxation in blood vessels," in Proceedings of the National Academy of Sciences in North America, first published Nov. 17, 2014, vol. 11, no. 50 pp 17977-17982 (the entire contents of which are incorporated herein by reference) have found that delivering light to blood vessels can deter vascular disease. Accordingly, in another embodiment of the present invention, light from internal light sources inside blood vessels can stimulate blood vessels. It was learned by Berkowitz that melanopsin (opsin 4) is one group of nonimage-forming light receptors that are present in blood vessels elsewhere in the human body which help set the circadian rhythms that affect the body's daily cycle of physical, mental and behavioral changes. Berkowitz et al. reported a physiological role for Opn4 in regulating blood vessel function, particularly in the context of photorelaxation.

Berkowitz et al. further reported that opsin 4 (a classic G protein-coupled receptor) is expressed in blood vessels. Vasorelaxation was reported by Berkowitz et al. to be wavelength-specific, with a maximal response at vessels at low-intensity blue light (380-495 nm), which was reported by Berkowitz et al. to correspond to the optimal absorption wavelength for the mouse Opn4 receptor. In short, Berkowitz et al. found that exposure of the blood vessels to blue light increased blood flow.

In general, a variety of different microbial opsins and genetically modified opsins have been used and developed to date for optogenetic manipulations. In the art, the term opsin describes a light-responsive protein, independent of its chromophore type (e.g., retinal, flavin), mode of action (e.g., phosphorylation, ion conductance's), or function (e.g., phototaxis, vision).

Typically, two superfamilies are distinguished: (1) microbial opsins (type I), including opsins from prokaryotes, fungi, and algae and (2) animal opsins (type II), which are found in eumetazoans.

Although both opsin types are transmembrane proteins and may share a common origin, they differ significantly from each other. Microbial opsins are mainly light-activated ion pumps or channels, which directly transduce electromagnetic signals into electrical currents. On the other hand, all type II opsins belong to the family of G protein-coupled receptors (GPCRs), which initiates protein-protein interaction and subsequent intracellular signaling cascades.

Microbial opsins, of type I, utilize all-trans as a chromophor, which stays covalently bound to the opsins after photoisomerization, whereas type II opsins use cis to trans isomerization of retinal (retinaldehyde) to transmit light stimuli. All vertebrate tissues investigated so far already contain sufficient amounts of retinal to constitute the protein, so that no additional retinal has to be supplied.

After the establishment of channelrhodopsin 2 (ChR2), a blue light-gated cation-selective ion channel from green algae ChR2, as an excitatory optogenetic tool, the first inhibitory tool was described. NpHR, a chloride pump from *Natronomonas pharaonis*, was used to silence neurons in vitro and in vivo. NpHR has its excitation maximum around 600 nm. In addition to opsins that regulate chloride pumps, opsins that control outward proton pumps, i.e., bacteriorhodopsins, such as eBR, Arch, and Mac, have also demonstrated their ability to inhibit neuronal firing. These capabilities have raised the possibility that optogenetic therapies can treat degenerative diseases of the eyes, hearing loss, and spinal cord injuries, as well as play a role in deep brain stimulation therapies.

In general, light-gated actuators have been known to control neuronal activity. Specific light-sensitive elements in phototransduction machineries underlying animal vision were found to be membrane-embedded photopigments called rhodopsins, each rhodopsin molecule consisting of a protein called opsin (belonging to the family of G-protein-coupled receptors or GPCRs) covalently bound to a chromophore (a vitamin A-related compound called retinal or one of its derivatives). Upon illumination, the bound retinal molecule undergoes isomerization, which induces conformational changes in the opsin backbone and activates a G-protein signaling pathway. Indeed, the first light-actuated control systems were designed to modulate neuronal firing.

In this invention, the light from the internal light source materials noted above (e.g., phosphors, fluorescent agents, etc.) can be used to treat different types of diseases and disorders such as those described above. In one embodiment, the light from the internal light source materials noted above could be used to treat degenerative diseases of the eyes, hearing loss, and spinal cord injuries, as well as play a role in deep brain stimulation therapies. In one embodiment, the light from the internal light source materials noted above could be used to treat vascular disease including peripheral artery disease, aneurysms and Raynaud's disease (a condition causing people to feel numbness and cold in their fingers and toes due to the narrowing of the small arteries that supply blood to the skin) by emission of characteristic wavelengths of light which triggers the light receptors in blood vessels. Specifically, in one embodiment, the endothelial cells that line blood vessels can be exposed to blue light (380-495 nm) generated from the internal light sources noted above such that, upon patient exposure to x-rays, blue light emitted from the internal light source would affect blood flow.

In one embodiment of the invention, a phosphorescent or fluorescent or light emitting material such as those described above (e.g., x-ray induced persistent phosphors) would be encased with a biocompatible coating transparent to blue light and introduced into the blood stream or into the body of the blood vessel or nearby a blood vessel. Upon exposure to x-rays, the phosphorescent or fluorescent or light emitting material would emit blue light which would be absorbed in the walls of the blood vessel to affect a change in blood flow for example by way of triggering a response in melanopsin (opsin 4) in the blood vessel walls.

In other work, workers have sought to optically control $Ca^{2+}$ signals. $Ca^{2+}$ acts as a messenger to regulate a myriad of cellular activities, ranging from short-term reactions occurring within seconds (e.g., muscle contraction and neurotransmitter release) to long-term processes that last for hours or even days (e.g., gene transcription). The location, amplitude and frequency of $Ca^{2+}$ signals in mammalian cells undergo constant changes to maintain $Ca^{2+}$ homeostasis while meeting the diverse requirements of different $Ca^{2}$-modulated events. Activation of cell-surface receptors, such as G protein-coupled receptors (GPCRs) and receptor tyrosine kinases (RTKs), results in mobilization of $Ca^{2+}$ release from internal $Ca^{2+}$ stores. Upon ligand binding to these receptors, PLC is activated to hydrolyze the PM-bound lipid, phosphatidylinositol 4,5-bisphosphate (PIP2), generating two second messengers: inositol 1,4,5-trisphosphate(IP3) and diacylglycerol (DAG). DAG is an activator of protein kinase C (PKC) and may directly activate certain types of transient release potential (TRP) channels, resulting in $Ca^{2+}$ influx from the extracellular space. Photo-switchable DAG and its analogs based on the azobenzene photo-switch have been developed to modulate PKC dependent pathways.

In one embodiment of the present invention, the examples given above are but illustrative of the present invention's capability for use in optogenetics. More specifically, the present invention provides the capability to provide light to opsins and other light-driven actuator proteins in order to impact a number of physiological parameters ranging from membrane voltage and calcium concentration to metabolism.

Tunneling Nanotubes

Tunneling nanotubes TNTs have been found to exist between adjacent cells. Moreover, recent studies have found TNTs to be dynamic connections between cells, providing a route for cell-to-cell communication. TNTs are considered to play a role in intercellular exchanges of signals, molecules, organelles, and pathogens. TNTs can from in a number so cell types, including neuronal cells, epithelial cells, and almost all immune cells. In myeloid cells (e.g., macrophages, dendritic cells, and osteoclasts), intercellular communication via TNT is believed to contribute to their differentiation and immune functions. TNTs are believed to be one way for myeloid cells to communicate with a targeted neighboring or distant cell, as well as with other cell types, therefore creating a complex variety of cellular exchanges. TNTs may also contribute to pathogen spread as they are believed to serve as "corridors" from a cell to another.

Vignas et al have described in "Cell Connections by Tunneling Nanotubes: Effects of Mitochondrial Trafficking on Target Cell Metabolism, Homeostasis, and Response to Therapy," in Stem Cells Int. 2017; 2017: 6917941. (the entire contents of which are incorporated herein by reference) that TNTs can be a means of communication between cells devised to allow long-distance cell-to-cell contacts. This paper reported that the formation of tunneling nanotubes (TNTs) between these cells was initially reported in the rat pheochromocytoma-(PC12-)derived cells and in immune cells. These TNTS were long tubular structures, with diameters between 50 and 1500 nm, that could span several tens to hundreds of microns, connecting two cells together. In a characteristic manner, in 2D cultures, TNTs were not tethered to the extracellular matrix, rather floating in the culture medium. This paper reported that the tunneling nanotubes allowed a continuity in plasma membrane and cytoplasm between the connecting cells, thus allowing trafficking of a number of cellular components from one cell to the other.

Furthermore, this paper reported that cells of the immune system, notably macrophages, dendritic cells (DCs), NK, and B cells, extensively use TNTs to communicate. According to this paper, the transfer of antigenic information from migratory DCs to lymph node-residing DCs through TNTs has been shown to be critical for the induction of immune responses. TNT formation was also described in neural CAD cells (mouse cell line of catecholaminergic origin) and from bone marrow-derived dendritic cells to primary neurons.

Rustom in "The missing link: does tunneling nanotube-based supercellularity provide a new understanding of chronic and lifestyle diseases?," from http://rsob.royalsocietypublishing.org/on Sep. 3, 2018 (the entire contents of which are incorporated herein by reference) describes a number of ways for TNT formation. The paper notes that, in general, oxidative stress is defined as an imbalance between the production of free radicals and reactive metabolites, such as $H_2O_2$ or superoxide anions, and their elimination by the antioxidative cell defense system. The list of severe diseases that have been linked to oxidative stress is long, including neurodegenerative disorders, such as Alzheimer's and Parkinson's, chronic inflammation, diabetes and cancer. The paper notes that it is well accepted that most reactive oxygen species (ROS) are generated in cells by the mitochondrial respiratory chain.

The paper noted that to counter stress, "stressed cells" will distribute "'call-for-help' signals to determine the position of unstressed cells in their surrounding." The paper describes that, while the nature of these signals is still under debate, candidate molecules are advanced glycation end products (AGEs).

In this paper, local stress leads to increasing ROS levels and AGE distribution from the stressed cell (a-1). AGE and receptor for AGE (RAGE) interaction at the target cells leads to cROS increase (a-2) and AC-TNT formation via actin-based, filopodia-like cell protrusions in order to restore redox/metabolic homeostasis by intercellular material exchange (a-3). Further increasing ROS levels lead to MT-TNT formation (b-1), allowing for efficient redox/metabolic rescue of stressed cells, e.g. via motor protein-mediated intercellular transfer of mitochondria along microtubules (b-2). Finally, exaggerated ROS levels induce apoptosis (c-1). Note that prior to apoptosis, remaining TNT connections are severed in order to isolate and remove 'degenerated' cells from the collective (c-2)—probably controlled by altered cholesterol/oxysterol homeostasis.

Accordingly, in one embodiment of the present invention, the biophotonic sources described above and/or the biophotonic bypasses could be used to stimulate formation of TNT growth. For example, the live biophotonic sources described above could be stressed (in a number of conventional ways) or selected portions of organs could be stressed as noted elsewhere. The stressed cells would then emit "call-for-help signals" (which regardless of their origin and nature would stimulate formation of TNTs. For example, the artificial biophotonic sources or the above-noted biophoton stimulator would emit light at a frequency and dose level which could stimulate formation of TNTs. For example, Wang et al in "Transfer of mitochondria via tunneling nanotubes rescues apoptotic PC12 cells," in Cell Death Differ. 2015 July; 22(7): 1181-1191 (the entire contents of which are incorporated herein by reference) show that UV light induced TNT formation presumably through the stress induced on the cells by the UV light.

In one embodiment of the present invention, the network of TNTs induced by the cell communication would permit healthy cells to strengthen their interconnection with other healthy cells, thus providing resistance to infection from other diseased cells.

In one embodiment of the present invention, the network of TNTs induced would permit cancerous cells undergoing apoptosis to experience cell death at a higher rate, thus controlling tumor growth.

In one embodiment of the present invention, the network of TNTs induced would permit organs subject to inflammation to build their interconnection to other nearby cells, thus providing a mechanism for the inflammation to be reduced by permitting mesenchymal stem cells (MSCs) to be transferred. Such cells are known to contributes to tissue repair and immunosuppressive properties. Once at the inflammation site, MSCs prevent cellular destruction and damage to surrounding tissues. MSC immuno-suppression is mediated by the secretion of soluble factors like indoleamine 2,3-dioxygenase (IDO), IL-10, TSG-6 (TNF-α-stimulated gene/protein 6), prostaglandin E2 (PGE2), TGF-β-1, inducible nitric oxide synthase (iNOS) and human leukocyte antigen (HLA-G).

Building Blocks of the Invention

The present invention takes advantage of several fundamental building blocks by which it can affect a physical, chemical, and/or therapeutic change or a treatment area. Below is a non-limiting and non-exclusive discussion of these building blocks provided as guidance on implementing the procedures and tools described above.

One building block involves the phenomenon of cell-to-cell communication discussed above in which different cells in different regions "communicate" with each other even without necessarily being in physical or fluid contact with one another. As discussed above, there are a number of mechanisms in the literature for how the cell-to-cell communication can work. One mechanism discussed above and utilized in the present invention is by omission of a biophoton also known as mitogenic radiation. Other mechanisms discussed above and utilized in the present invention is by emission of electromagnetic radiation or sonic radiation. Another mechanism discussed above and utilized in the present invention is by coupling through coherent quantum states, where the change in the state at one location produces a concomitant change in the quantum state at another location. Another mechanism discussed above and utilized in the present invention is by coupling of excited states in a cellular bioplasma.

Closely related to the last two effects is that of quantum entanglement. Experiments with green fluorescent proteins in a biological living medium have shown the photons emitted from separated molecules to be related as "entangled pairs" with the photons' polarizations entangled such that, by determining the polarization of one emitter, the polarization of the quantum entangled other emitter was known a priori. Here, the cell-to-cell communication utilized in the present invention to induce effects in neighboring cells may well be a quantum entanglement phenomenon.

Another building block involves the capability to affect the quantum or physical states of the biological structures of a cell. For example, as discussed above, cellular processes associated with membranes in a cell are controlled by factors such as pore size, the thickness of the membrane, and the polarity of the membrane. These pore sizes and thicknesses are on the nanometer scales, and therefore are susceptible to being influenced by applied radiation, by applied electromagnetic fields, and/or by applied localized electric fields which the physics of diffusion and transport even at the quantum scale can influence the transport of materials through the membranes or the attachment of antibodies to the cell membrane.

Another building block used by the present invention is the realization that photosynthesis-type reactions (occurring in the realm of plants) are also a mechanism at play inside living cells of animals. Here, light can induce not only the generation of biophotons as discussed above but also can promote reactions in the cells such as increased metabolism of a cell, cell division, or cell death Another building block used by the present invention is the realization that there are many pathways before communication between cells including those of physically connected pathways such as the tunneling nanotubes (TNTs) discussed above. These pathways can be used for both productive and detrimental uses. In the present invention, mechanisms to shut down selected pathways can be used to control/restrict the spread of viruses, bacteria, or cancer from one region of the body to another. In the present invention, mechanisms to promote certain pathways can be used to promote cell regeneration, for example, in the regrowth of healthy heart tissue inside a diseased heart.

Yet another building block used by the present invention is the realization of the impact of outside stimulus, such as a biophoton, on the epigenome. For example, it has been shown that identical twins having identical DNA at birth can have their DNA changed by environmental factors. Here, in vivo light or light delivered in situ such as for example biophotons can be used to interact directly with the DNA encoded in the cells to implement a therapeutic change.

Quantized Biology:

In one embodiment of the invention, and in other embodiments described below, photonic energy can participate and control the various metabolic processes in an individual cell or a group of cells. Control of the metabolic processes in one region (a control region) may be coupled to another region (e.g., a treatment site inside the patient, where the coupling can induce a biological, chemical, physical, or therapeutic change in the subject at the other region or the treatment site). Alternatively, in one embodiment of the invention, the photonic energy (as described for example in the following) can directly cause a biological, chemical, physical, or therapeutic change at a treatment site In one embodiment of the invention, $hv_i$ is a photonic energy that is ionizing and can therefore be responsible for catalyzing a chemical reaction. Other energies ($hv_j$) generated through energy converters (such as UV or other energy generated from the phosphors described herein) could create a free radical hence inducing a charge-build up in a protein of low molecular weight or on a side group of a long molecular weight protein. Once the ionization of a protein takes place, this ionization could result in a dysfunctional behavior of the protein, and subsequently the failure of the protein to achieve the intended process. For example, in one embodiment of the invention, $hv_i$ or $hv_j$ induced ionization of an epidermal growth factor receptor (EGFR) protein can denature or render the EGFR protein dysfunctional. EGFR is considered a transmembrane protein that is a receptor for members of the epidermal growth factor family (EGF family) of extracellular protein ligands. Deficient signaling of the EGFR and other receptor tyrosine kinases in humans is associated with diseases such as Alzheimer's, while overexpression is associated with the development of a wide variety of tumors. Interruption of EGFR signaling, either by blocking EGFR binding sites on the extracellular domain of the receptor or by inhibiting intracellular tyrosine kinase activity, may prevent the growth of EGFR-expressing tumors and might improve a patient's condition.

In one embodiment of the invention, $hv_k$ is a photonic energy responsible for signaling an aspect of a protein conformation. This photonic energy $hv_k$ would typically not be ionizing. In another embodiment of the invention, $hv_z$ is a photonic energy responsible for signaling an aspect of a protein conformation that closes an ion channel or multiple ion channels. In a further embodiment of the invention, $hv_x$ is a photonic energy responsible for signaling an aspect of a protein conformation that opens an ion channel or multiple ion channels.

Hence, in one aspect of this invention, photonic energy can be used to promote reactions in some cases ($hv_i$), promote ionization and denaturing of certain proteins ($hv_j$), change protein conformation ($hv_k$), and/or signal the closure and the opening of ion channels ($hv_z$, $hv_x$). Energy converters in one embodiment (such as the phosphors described elsewhere) can be used to convert high energy incident radiation such as x-ray into one or more of $hv_i$, $hv_j$, $hv_k$, $hv_z$, and/or $hv_x$ which can interact within the cell environment to promote or prohibit the functions of those cells. The use of such high energy incident radiation (such as x-ray), which can penetrate completely through the subject body, permits the implementation of the invention deep within the body in a non-invasive manner, requiring at most only injection of the desired energy converters to the desired site.

The following examples performed using poly(deoxyadenylic-deoxythymidylic) acid sodium salt (poly-dAdT) and 8-methoxypsoralen (8-MOP) demonstrates this aspect of the invention and shows the effects of photonic energy to promote biologically driven reactions via quantized effects.

Monoadduct (MA) Formation and Di-Adduct Formation or Cross-Linking (XL)

In the examples below, the energy promoters (i.e., the phosphors designated below as BP3, BP10, and BP6) absorb X-Ray energy and emit photonic energy from the UVA to the visible range as listed below (name, emission peak):

| Properties | (BP3, 327 nm) BP3 | (BP10, 355 nm) BP10 | (BP6, 410 nm) BP6 |
|---|---|---|---|
| Peak Emission (nm) | 327 | 390 | 410 |
| hv = Photonic Energy (J) | 6.075E−19 | 5.093E−19 | 4.845E−19 |
| Intensity (AU) | 15,000 | 5,000 | 22,000 |
| Composition | YTaO$_4$ | BaSO$_4$-:Eu$^{2+}$ | YTaO$_4$:Nb |

Figure 16:
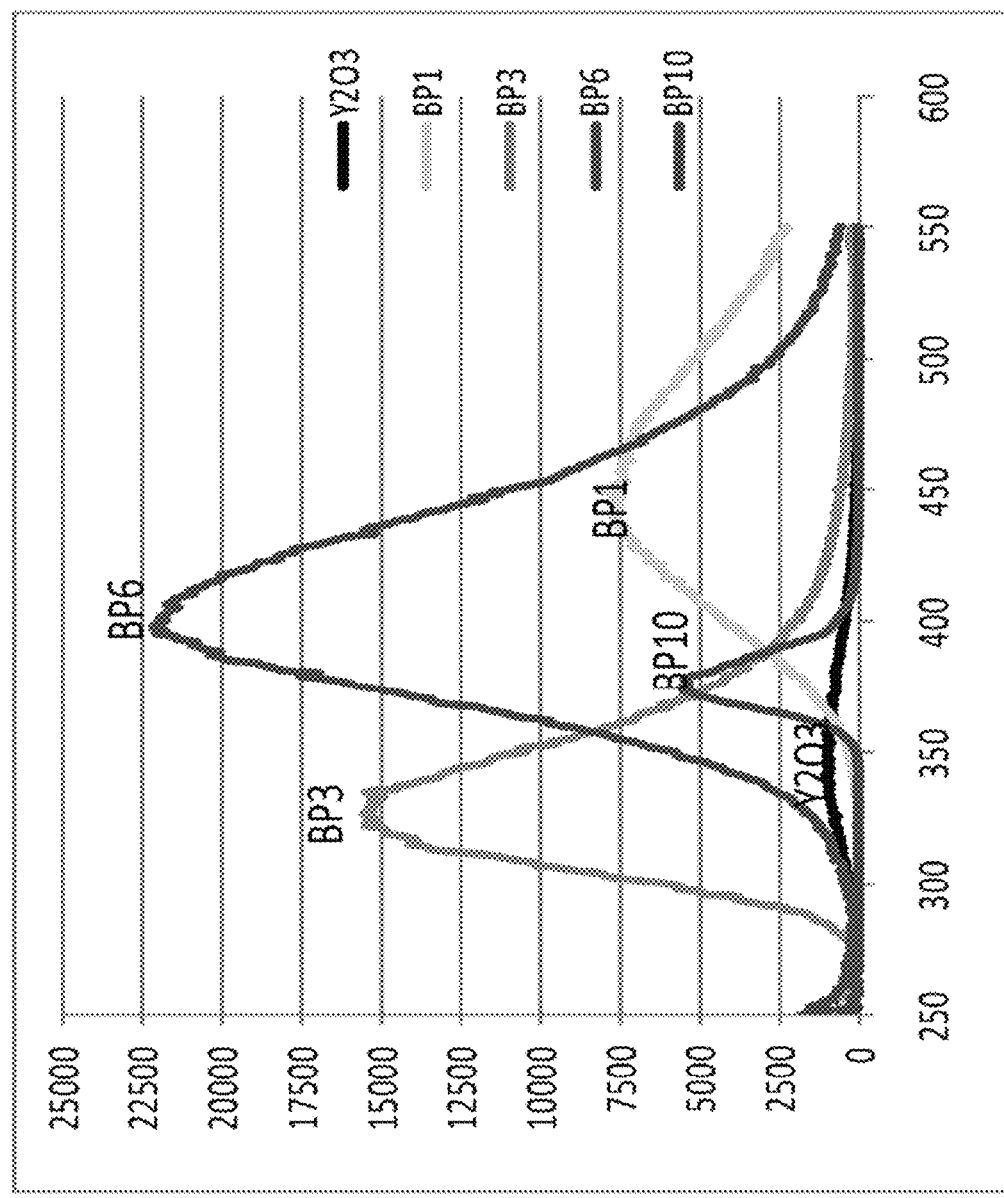
FIG. 16 shows the spectral emission of the BP3, BP10, and BP6 phosphors.

FIG. 16 shows the spectral emission of the BP3, BP10, and BP6 phosphors

Phosphors BP3, BP6, and BP10 were added to a solution of 8-MOP and Poly-dAdT, and exposed to various X-ray conditions. The plates were placed at the following distances from the X-ray source: 100 mm and 200 mm. This had the effect of changing the dose rate. The X-Ray parameters included 320 kV and 10 mA for a fixed time period. This example shows that monoadduct (MA) formation can be promoted for example by UV light with the higher energy light promoting more MA formation even at a lower flux or intensity.

Photonic Energy Comparison:

$$hv_{(BP3)} > hv_{(BP10)} > hv_{(BP6)}$$

Intensity Comparison:

$$I_{(BP6)} > I_{(BP3)} > I_{(BP10)}$$

Comparison of the phosphors in terms of Mono-Adduct (MA) formation as demonstrated in detail below showed that:

$$MA_{(BP3)} > MA_{(BP10)} > MA_{(BP6)}$$

Moreover, the observed MA formation tends to follow the photonic energy ranking rather than the intensity of the energy conversion from X-Ray to UV or visible light.

Similarly, other sets of experiments were performed further demonstrating the effect of photonic energy on both MA and di-Adduct formation (e.g. cross linking (XL)). Measurements of the MA and di-adduct formation (XL) were performed using high performance liquid chromatography (HPLC) to identify the presence of these compounds after exposure to photonic energy.

Figure 17:
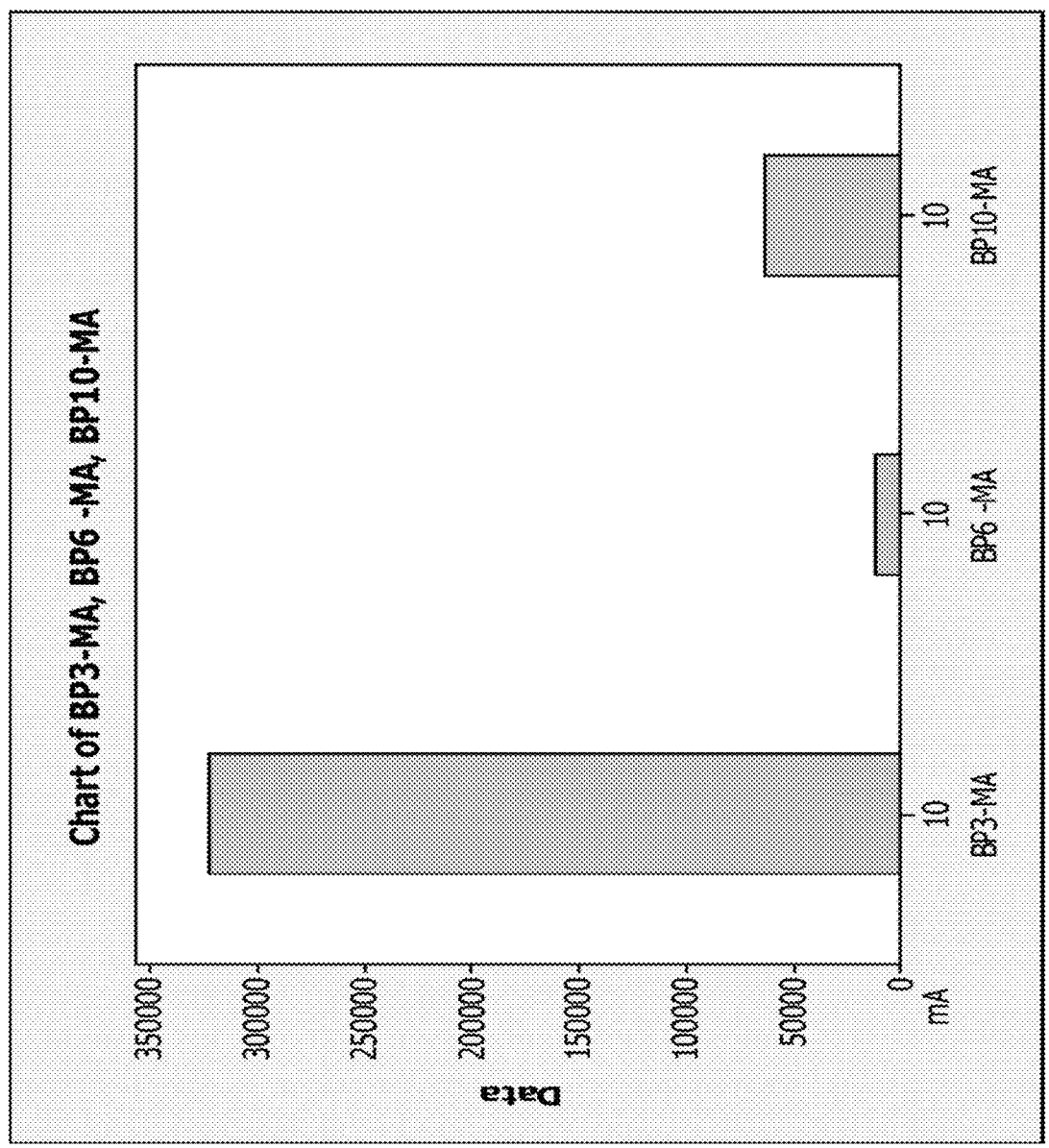
FIG. 17 is a chart showing that photonic energy from BP3 tends to produce more MA than BP6 or BP10.
Figure 18:
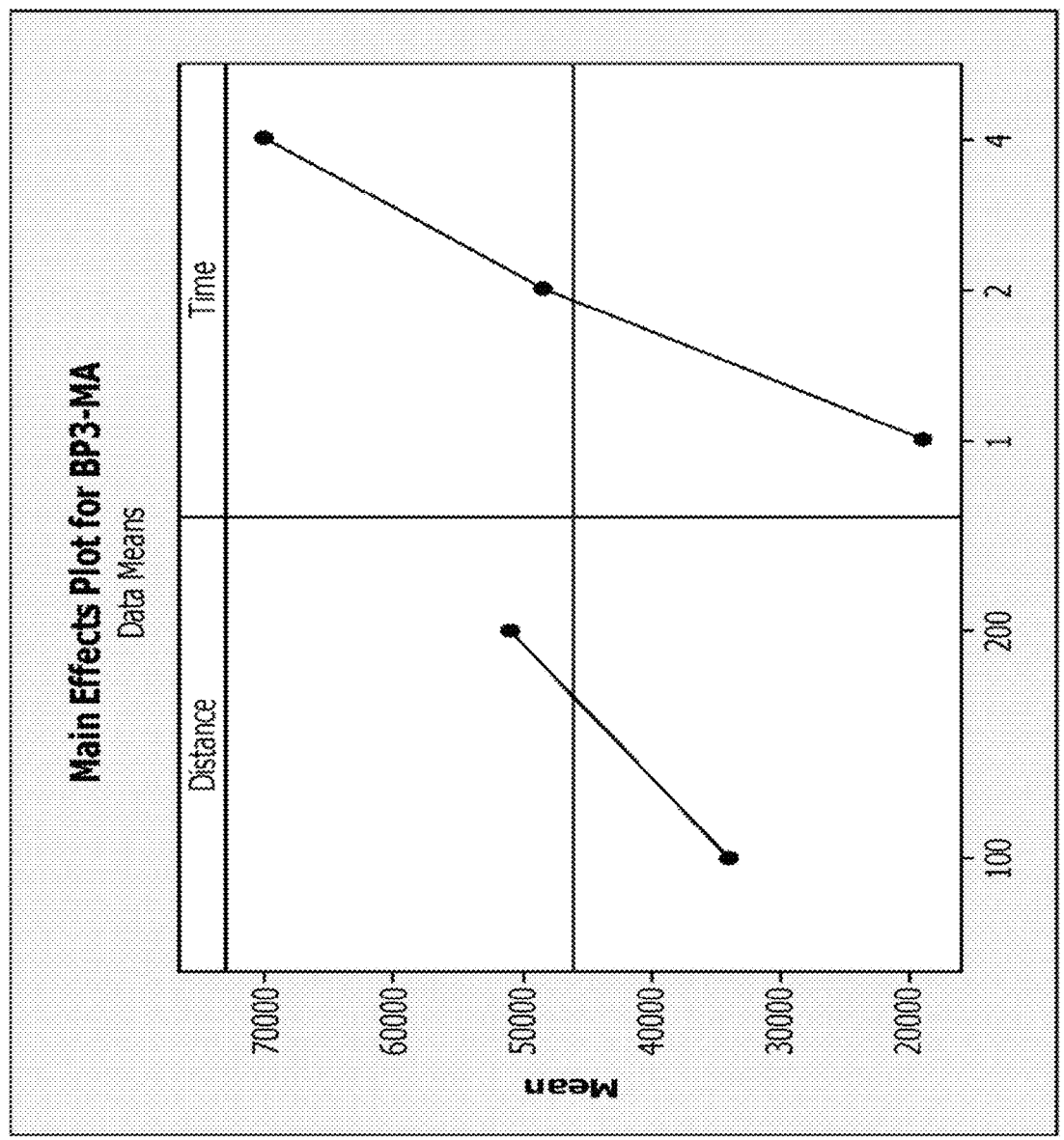
FIG. 18 is a chart showing MA formation under BP3 photonic energy as a function of distance from the X-ray source and time.
Figure 19:
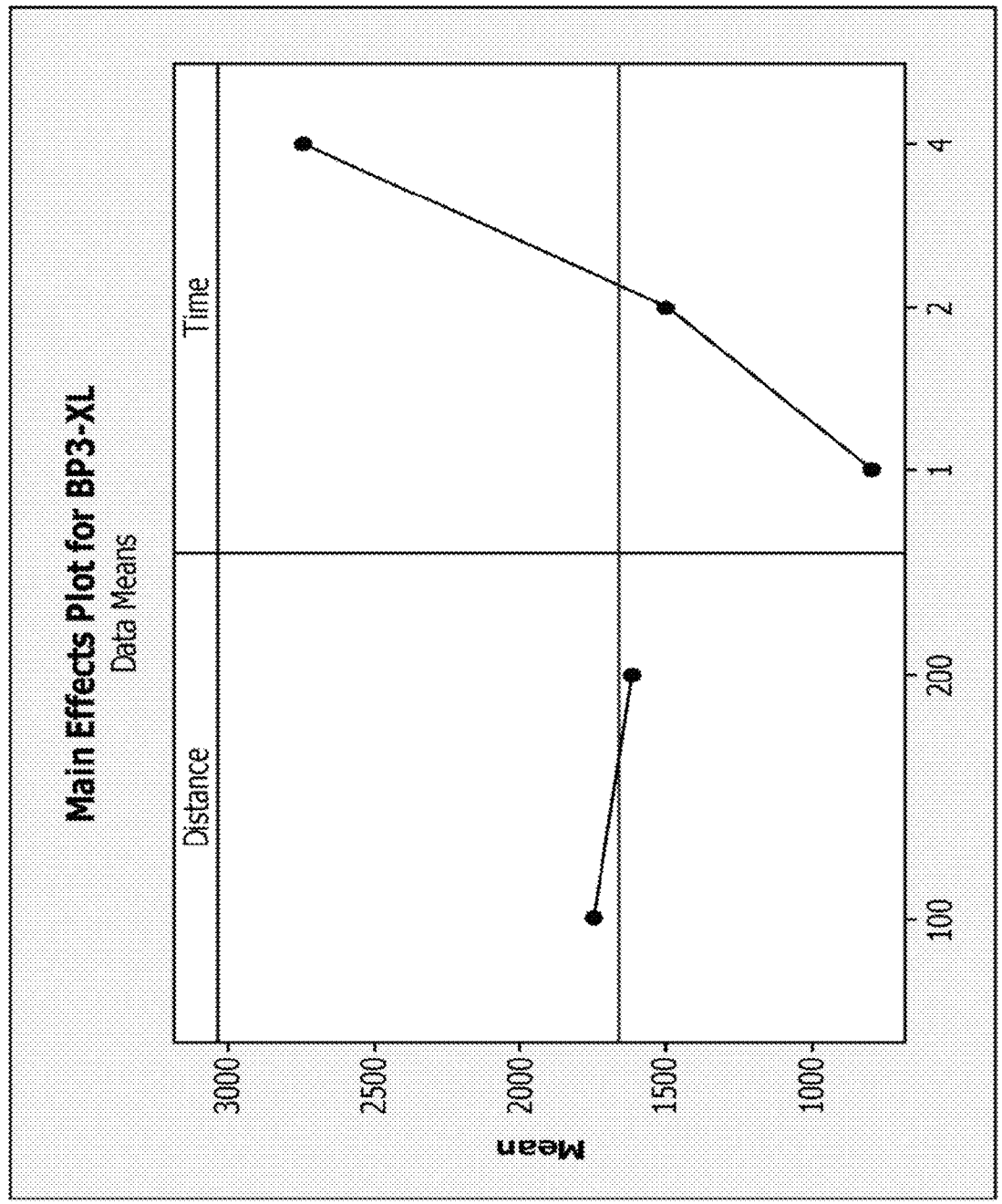
FIG. 19 is a chart showing XL under BP3 photonic energy as a function of distance from the X-ray source and time.
Figure 20:
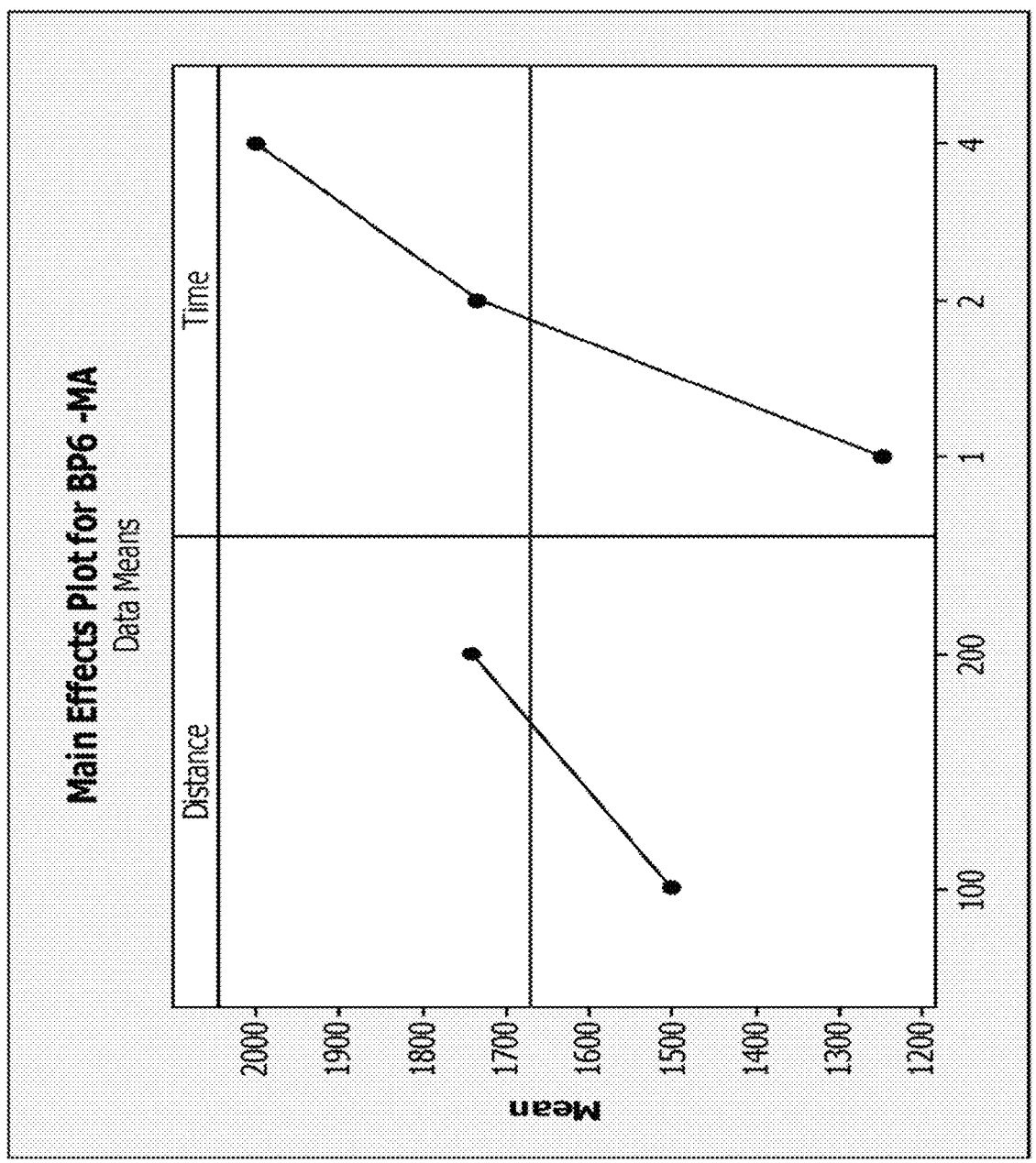
FIGS. 20-24 show results from other experiments corroborating MA formation and/or XL under photonic energy exposure.
Figure 21:
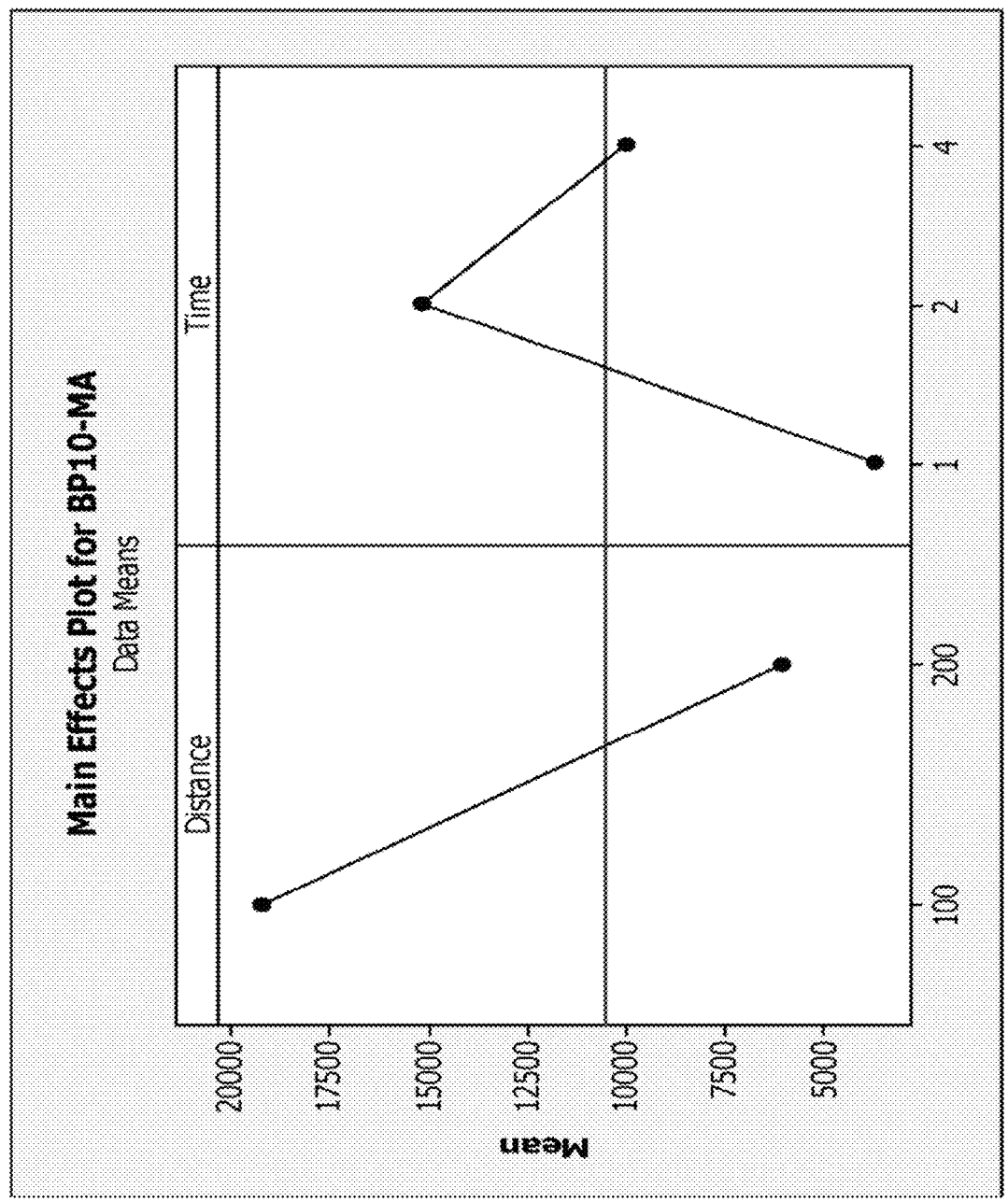
Figure 22:
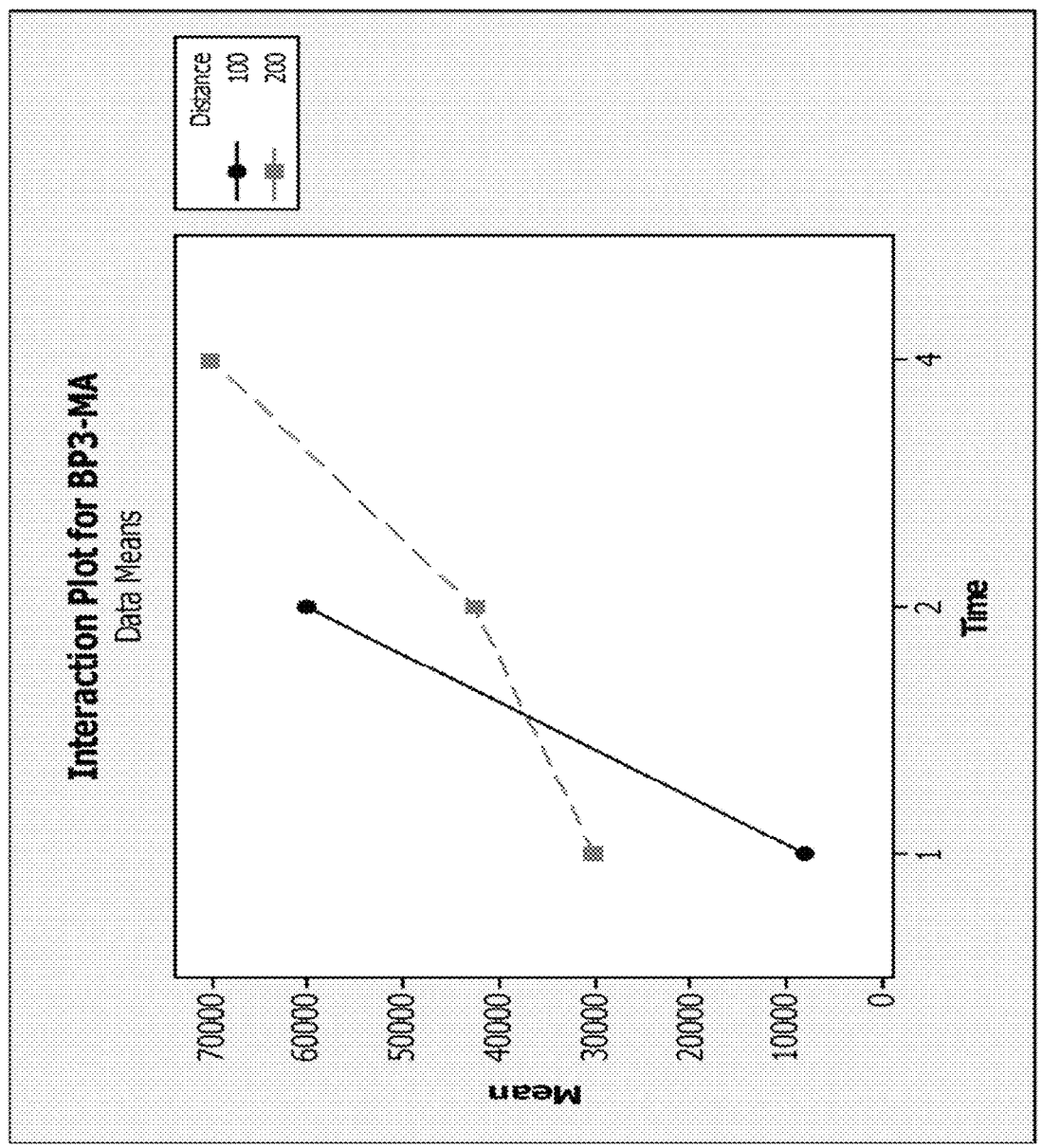
Figure 23:
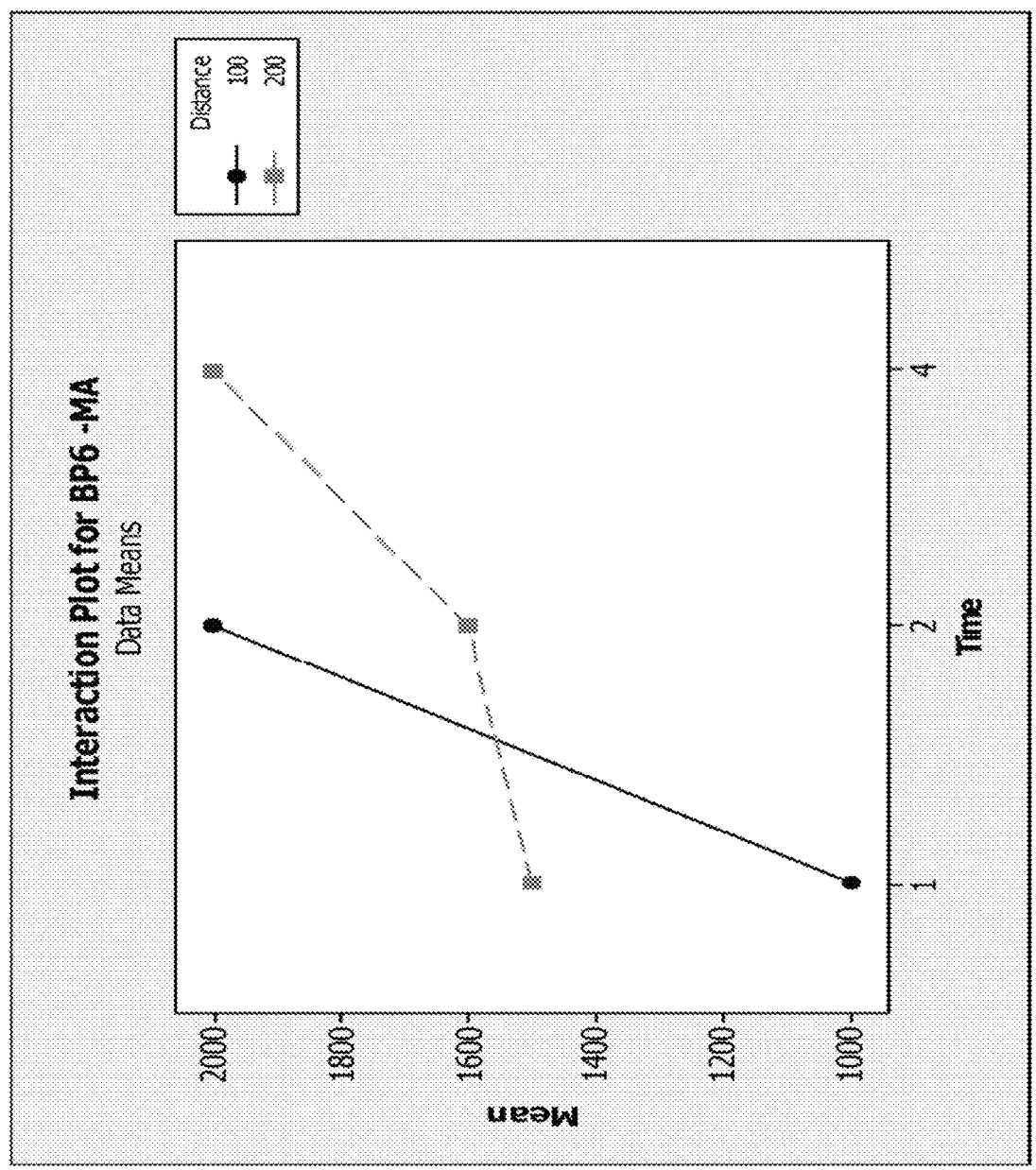
Figure 24:
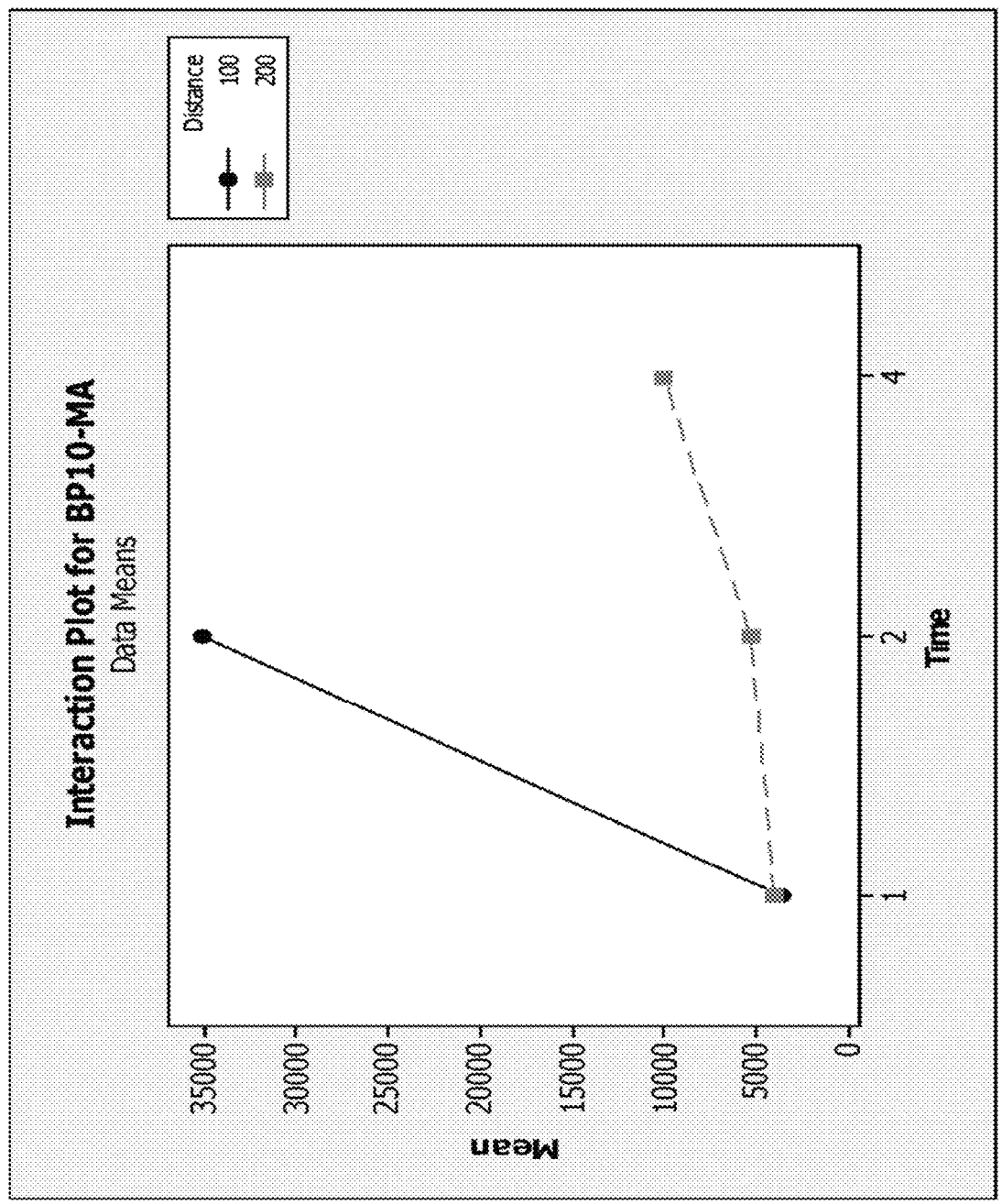

FIG. 17 is a chart showing that photonic energy from BP3 tends to produce more MA than BP6 or BP10. FIG. 18 is a chart showing MA formation under BP3 photonic energy as a function of distance from the X-ray source and time. Somewhat surprisingly, MA formation increases as the distance from the X-ray source increases. This points out that the right reaction is sensitive to dose rate. Lower dose rates in this case could be more beneficial. Regardless, the results show MA formation under BP3 photonic energy. FIG. 19 is a chart showing XL under BP3 photonic energy as a function of distance from the X-ray source and time. Here, XL decreases as the distance from the X-ray source increases and increases with time. It is worth noting that the XL reaction is reversible.

Figure 25:
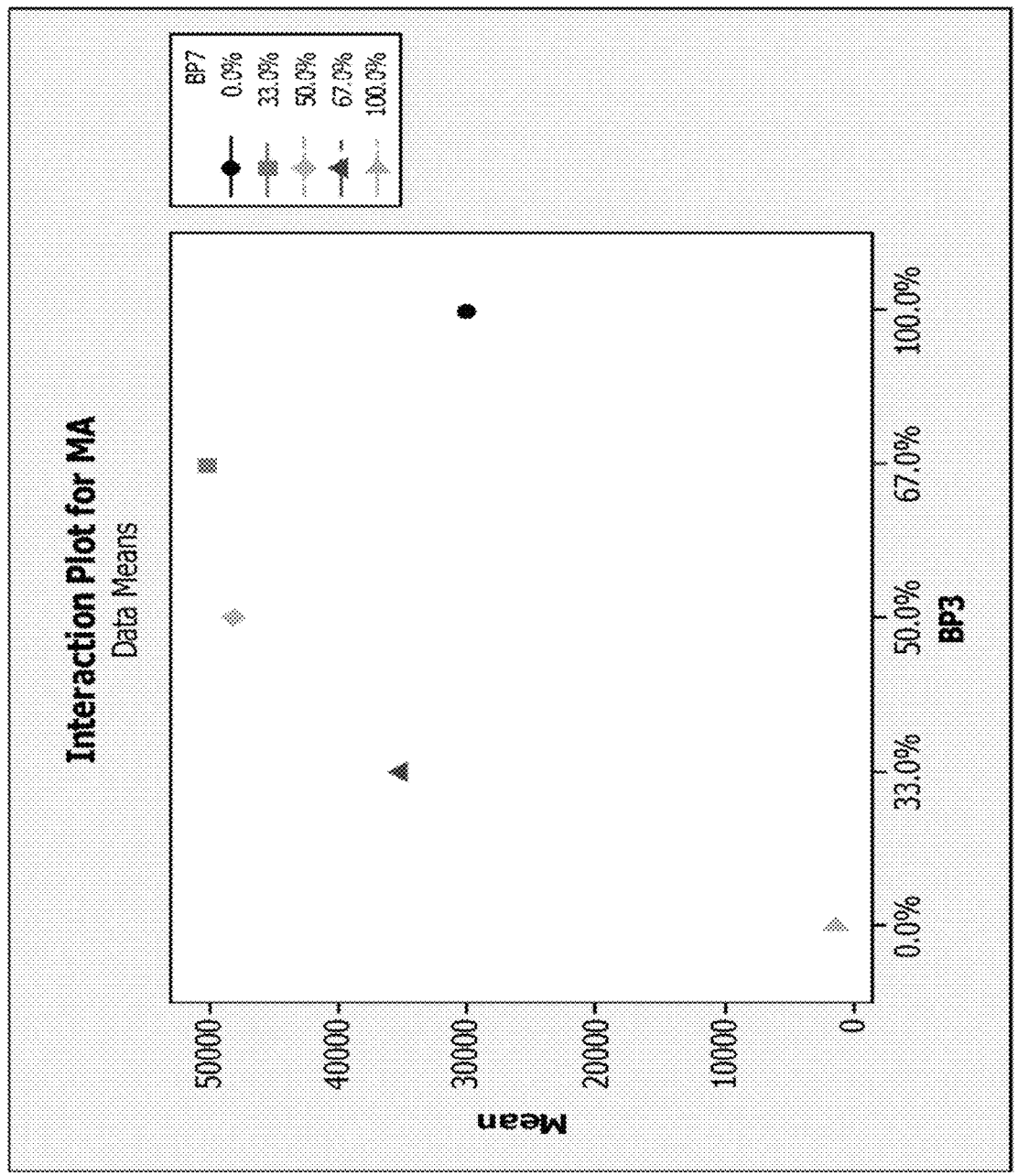
FIG. 25 is a chart showing a non-linear effect on MA seen by mixing two phosphors.

FIGS. 20-24 show results from other experiments corroborating MA formation and/or XL under photonic energy exposure. FIG. 25 is a chart showing a non-linear effect on MA seen by mixing two phosphors. Indeed, the mixtures of BP7 from at least 33% to 67% show higher MA formation than observed when using only BP3 or only BP7. The tables below summarize the results:

| BP6 | | | | | |
|---|---|---|---|---|---|
| | kvp | mA | Distance mm | Time (min) | MA1 | XL |
| S2 | 320 | 10 | 200 | 1 | 1,500 |
| S6 | 320 | 10 | 200 | 2 | 1,700 |
| S10 | 320 | 10 | 200 | 2 | 1,500 |
| S14 | 320 | 10 | 200 | 4 | 2,000 |
| S18 | 320 | 10 | 200 | 4 | 2,000 |
| S22 | 320 | 10 | 100 | 2 | 2,000 |
| S26 | 320 | 10 | 100 | 1 | 1,000 |

| BP3 | | | | | | |
|---|---|---|---|---|---|---|
| | kvp | mA | Distance mm | Time (min) | MA1 | XL |
| S1 | 320 | 10 | 200 | 1 | 30,000 | 600 |
| S5 | 320 | 10 | 200 | 2 | 40,000 | 1000 |
| S9 | 320 | 10 | 200 | 2 | 45,000 | 1,000 |
| S13 | 320 | 10 | 200 | 4 | 70,000 | 2,500 |
| S17 | 320 | 10 | 200 | 4 | 70,000 | 3,000 |
| S21 | 320 | 10 | 100 | 2 | 60,000 | 2,500 |
| S25 | 320 | 10 | 100 | 1 | 8,000 | 1,000 |

| BP10 | | | | | | |
|---|---|---|---|---|---|---|
| | kvp | mA | Distance mm | Time (min) | MA1 | XL |
| S4 | 320 | 10 | 200 | 1 | 4,000 | |
| S8 | 320 | 10 | 200 | 2 | 4,000 | |
| S16 | 320 | 10 | 200 | 4 | 6,500 | |
| S20 | 320 | 10 | 200 | 4 | 10,000 | |
| S24 | 320 | 10 | 100 | 2 | 35,000 | |
| S28 | 320 | 10 | 100 | 1 | 3,500 | |

Similarly, experiments have shown that phosphor combinations can promote higher XL than the individual phosphors alone.

| BP3 (g) | BP7 (g) | BP3 | BP7 | MA | XL |
|---|---|---|---|---|---|
| 0.3 | 0 | 100.0% | 0.0% | 3.00E+04 | 5.00E+02 |
| 0.2 | 0.1 | 67.0% | 33.0% | 5.00E+04 | 6.00E+02 |
| 0.15 | 0.15 | 50.0% | 50 | 4.80E+04 | 5.00E+02 |
| 0.1 | 0.2 | 33.0% | 67.0% | 3.50E+04 | 4.50E+02 |
| 0 | 0.3 | 0.0% | 100.0% | 1.40E+03 | 0.00E+00 |

Activation and Deactivation of a Signaling Protein

Living cells possess sophisticated molecular machinery and control systems. Living cells convert food into energy, such as ATP, which drives the millions of biochemical processes necessary for keeping us alive. The pathways used to convert substrates such as glucose into products are collectively referred to as metabolic pathways. The drivers of these metabolic pathways are enzymes that work to assist chemical reactions by building or breaking down molecules. The enzymatic protein does not drive reactions at a constant rate. The reaction rate can in fact speed up or slow down or even stop completely according to the cell's needs. The cell is considered to be self-regulated, and the supply of products does not exceed demand. If products are being created at a rate that is faster than they can be used, a slower rate or complete stoppage can take place through a process called feedback inhibition, which is part of Allosteric regulation. Allosteric regulation plays a role in many metabolic pathways and is considered to keep everything running smoothly and efficiently while maintaining homeostasis.

Allosteric Regulation: There are enzymatic and non-enzymatic proteins. Enzymes catalyze reactions, for example, such as in the case of DNA polymerase and Amylase. Non-enzymatic proteins play a large number of functions and roles, including, but not limited to, receptors/ion channels, transport, motor and antibodies.

Enzymes have active sites where substrates combine as well as allosteric sites where enzyme regulator can bind. There are two types of regulators: allosteric activators which increase enzymatic activity and allosteric inhibitors which decrease enzymatic activity. A feedback loop gets established whereby the downstream products regulate upstream reactions. An increase or decrease of enzymatic activity is therefore tailored to the specific needs of the cell.

Mutated enzymes that do not respond to allosteric regulation have been linked to disease states, such as cancer. Many processes in our bodies rely on molecular feedback inhibition to maintain homeostasis.

In the present invention, photonic energy can be used to promote allosteric activators which increase enzymatic activity and/or promote allosteric inhibitors which decrease enzymatic activity, therefore targeting diseased cells to curtail runaway growth conditions In one embodiment, as noted above, a signaling protein can be activated and deactivated using photonic energy. In this embodiment, an energy converter such as BP3, BP6, and/or BP10 would be located nearby or inside a cell to generate photonic energy, such as UV or visible light, to promote the function or the suppression of a signaling protein.

Light-activated DNA binding in a designed allosteric protein has been reported by Devin Strickland, Keith Moffat, and Tobin R. Sosnick, Department of Biochemistry and Molecular Biology and Institute for Biophysical Dynamics, University of Chicago, 929 East 57th Street, Chicago, IL 60637, edited by David Baker, University of Washington, Seattle, WA, and approved May 12, 2008 (received for review Oct. 9, 2007) in "Light-activated DNA binding in a designed allosteric protein," the entire contents of which are incorporated herein by reference.

An understanding of how allostery, the conformational coupling of distant functional sites, arises in highly evolvable systems is of considerable interest in areas ranging from cell biology to protein design and signaling networks. The rigidity and defined geometry of α-helical domain linker was reasoned to make it effective as a conduit for allosteric signals. The idea was tested by designing twelve fusions between the naturally photoactive light-oxygen-voltage-sensing domain LOV2 domain from *Avena Sativa* phototropin 1 and the *Escherichia coli* trp repressor were investigated by Strickland et al. When illuminated with photonic energy, one of the fusions selectively binds to operator DNA and protects it from nuclease digestion. The helical "allosteric lever arm" was considered by Strickland et al. to be a mechanism for coupling the function of two proteins. This is illustrated in FIG. 26.

Figure 26:
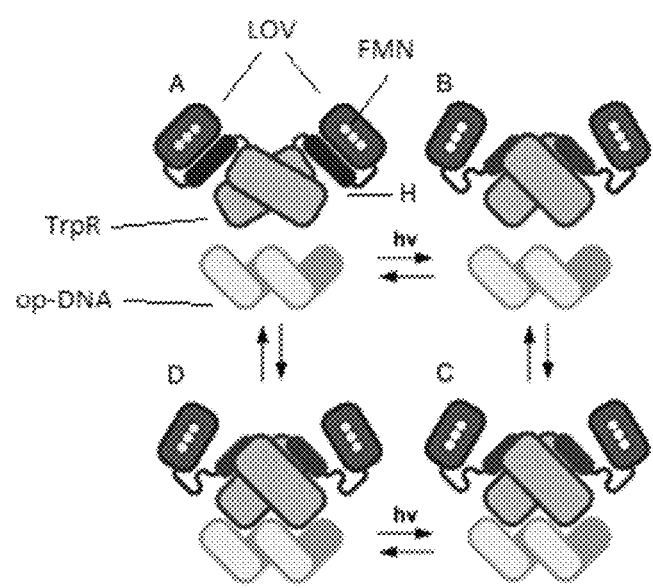
FIG. 26 is a depiction of a helical "allosteric lever arm" as considered by Strickland et al. to be a mechanism for coupling the function of two proteins.

In FIG. 26, the LOV domain (containing the three dots representing the three ring FMN chromophore), the TrpR domain in orange, and the operator DNA are depicted above in various states. The shared helix, H, is shown contacting the LOV domain in (A) and contacting the TrpR domain in (B)-(D). The three-ring FMN chromophore is in the ground state in (A) and (D) above and when photoexcited in (B) and (C). (A) In the dark DNA-dissociated state, the shared helix H contacts the LOV domain, populating an inactive conformation of the TrpR domain. (B) Photoexcitation disrupts contacts between the shared helix H and the LOV domain, populating an active conformation of the TrpR domain. (C) LovTAP binds DNA. (D) The LOV domains return to the dark state. LovTAP dissociates from the DNA, contacts between the shared helix H and the LOV domain are restored, and the system returns to the initial state.

Strickland et al. concluded that a successful design of an allosteric lever arm and a bistable energy surface, along with the observation of a natural analogue, suggesting the existence of a general but largely unrecognized mode of connecting modular domains into a functionally integrated whole. The α-helical structure of the linker distinguishes this mode from others in which allostery results from intramolecular binding between domains connected by linkers of undefined structure. Because a regular helix resists bending and twisting, it can function as an allosteric lever arm to transmit forces created by interdomain contacts to generate bistable systems.

Figure 27:
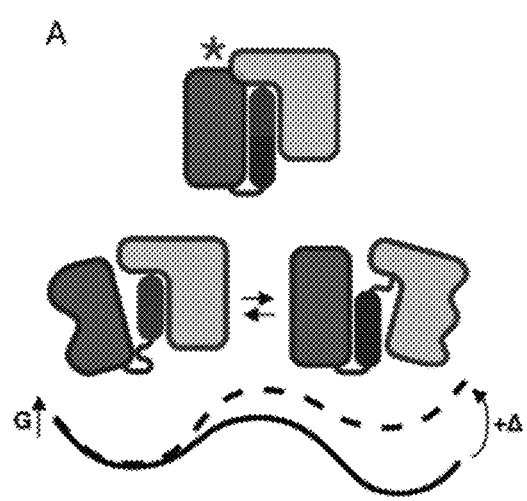
FIG. 27 is a depiction of a design of an allosteric, light activated repressor.

FIG. 27 provides a depiction of a design of an allosteric, light activated repressor. As shown in FIG. 27, (A) represents a conceptual model of an allosteric lever arm. Joining two domains across terminal α-helices creates a bi-stable system in which steric overlap (star) is relieved by the disruption of contacts between the shared helix and one or the other of the domains. A perturbation (Δ) such as ligand binding or photo-excitation alters the energy surface of the system (blackline) to favor a new conformational ensemble (dashed line) with different functional properties.

Here, in the present invention, photonic energy, for example from the energy converters noted above, can be used to photoexcite these types of reactions to promote light-activated DNA binding.

Furthermore, in the present invention, photonic energy can be used to activate a repressor. The following references (all of which are incorporated herein in their entirety by reference) describe repressors:

Freeman, S. Hamilton, H., Hoot, S., Podgorski, G., Ryan, J. M., Smtill, S. S., & Weigle, D. S (2002). Bilogical Science (Vol 1). Upper Saddle River, NJ: Prentice Hall.

Gerhart, J. C., & Pardee, A. B. (1962). The enzymology of control by feedback inhibition. J Biol Chem, 237, 391-896.

Tansey, J. T., Baird, T., Cox, M. M., Fox, K. M., Knight, J., Sears, D., Bell, E. (2013). Foundational concepts and underlying theories for majors in "biochemistry and molecular biology". Biochemisty and molecular biology education, 41 (5), 289-296.

Webb, B. A., Forouhar, F., Szu, F. E., Seetharaman, J., Tong, L., Barber, D. L. (2015). Structures of human phosphofructokinase-1 and atomic basis of cancer associated mutations. Nature 523 (7558). 111-114.

Oana I Lungu, Ryan A Hallett, Eun Jung Choi, Mary J. Aiken, Klaus M Hahn, and Brian Kuhlman, Department of Biochemistry and Biophysics, Department of Pharmacology, University of North Carolina Chapel Hill, NC 27599, USA, published an article in Chemistry & Biology 19, 507-517, Apr. 20, 2012 entitled "Designing Photoswitchable Peptides using the AsLOV2 Domain," the entire contents of each of which are incorporated herein by reference.

Lungu et al. describes that peptides can regulate a variety of biological processes by acting as competitive inhibitors, allosteric regulators and localization signals. Photo-control of peptide activity represents a tool for precise spatial and temporal control of cellular functions.

Lungu et al. showed that genetically encoded light-oxygen-voltage-sensing domain LOV2 domain of Avena Sativa phototropin 1 (AsLOV2) can be used to reversibly photo-modulate the affinity of peptides for their binding partners. Sequence analysis and molecular modeling were used to embed tow peptides into the Ja helix of the AsLOV2 domain while maintaining AsLOV2 structure in the dark but allowing for binding to effector proteins when the Ja helix unfolds in the light. Caged versions of the ipaA and SsrA peptides, LOV-ipaA and LOV-SsrA, bind their targets with 49- and 8-fold enhanced affinity in the light, respectively. These switched can be used as general tools for light-dependent colocalization, which Lungu et al. demonstrated with photoactivable gene transcription in yeast.

In another reference entitled *A light-triggered protein secretion system*, the entire contents of which are incorporated herein by reference, by Daniel Chen, Emily S. Gibson, and Matthew J. Kennedy, Department of Pharmacology, University of Colorado Denver School of Medicine, Aurora, CO 80045, Chen et al. confirmed the importance of light in various cellular functions.

Chen et al. used UVR8, a plant photoreceptor protein that forms photolabile homodimers, to engineer the first light-triggered protein secretion system. UVR8 fusion proteins were conditionally sequestered in the endoplasmic reticulum, and a brief pulse of light triggered robust forward trafficking through the secretory pathway to the plasma membrane. UVR8 was not responsive to excitation light used to image cyan, green, or red fluorescent protein variants, allowing multicolor visualization of cellular markers and secreted protein cargo as it traverses the cellular secretory pathway. Chen et al. showed that this could be used, as a tool in neurons, to demonstrate restricted, local trafficking of secretory cargo near dendritic branch points.

In general, the use of light to control basic cellular functions has transformed experimental biology. Some of the first approaches relied on photolabile small molecule analogues of second messengers, second messenger chelators, or neurotransmitters to control cellular physiology and signaling pathways with ultraviolet (UV) light. These "caged" compounds have been used for dissecting numerous molecular pathways governing cellular physiology with unprecedented spatial and temporal control. More recently, exogenously expressed photoreceptors from plants have been used to control cellular biochemistry by conditionally gating protein-protein interactions with light. This approach has emerged as a new and powerful way to control cellular processes on fast timescales with fine spatial precision without the need for small molecules. Some of the first studies describing engineered optical control of cellular functions used the plant photoreceptor phytochromeB. PhyB binds to members of the phytochrome-interacting family (PIF) of basic helix-loop-helix transcription factors when photoexcited with red (660 nm) light. Remarkably, PhyB/PIF interactions can be reversed by near-infrared (730 nm) excitation, allowing fast and local toggling of PIF binding.

However, PhyB-based systems require addition of an exogenous phycocyanobilin chromophore that is not normally present in yeast, flies, worms, or mammals, making it more difficult to implement than more recently developed systems that are entirely genetically encoded. These systems rely on blue light photoreceptor cryptochrome2 (Cry2), which binds to cryptochromeinteracting basic-helix-loop-helix 1 (CIB1) in response to blue light, and the light, oxygen, voltage (LOV) domain photoreceptors, which undergo a large conformational change when photoexcited UVR8 has many unique properties that including constitutive formation of photolabile homodimers, slow reversal kinetics, and a UV-B absorption profile, which enables multicolor imaging of widely used fluorescent proteins without activating the photoreceptor. UVR8 can be used to conditionally sequester secretory cargo in the ER. Moreover, light triggers robust forward trafficking to the plasma membrane.

Figure 28:
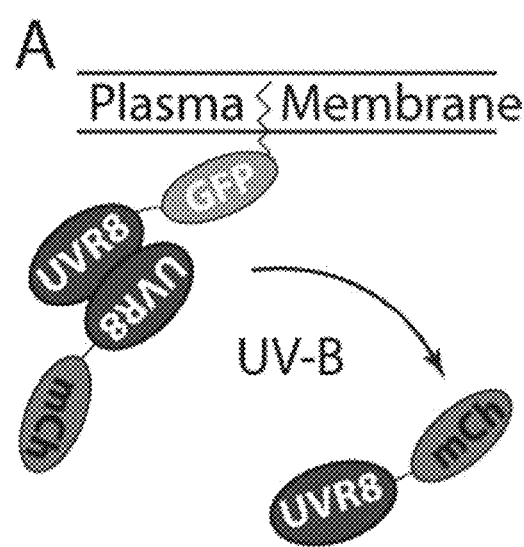
FIG. 28 is a depiction of the light-triggered dissociation of UVR8-tagged proteins.

FIG. 28 shows the light-triggered dissociation of UVR8-tagged proteins. UVR8 fused to prenylated GFP (UVR8-memGFP) localizes to the plasma membrane where it recruits UVR8-mCh. Dissociation of the UVR8 dimer by UV-B light releases UVR8-mCh to the cytosol Here, in the present invention, photonic energy from for example the energy converters noted above can be used to photoexcite these types of reactions.

In stacking up amino-acids in the right sequence, the various units constituting a given protein enter into an energetically favorable and stable configuration. The presence of water is reported to enable the correct folding through the influence of the various water molecules in the vicinity of the amino-acids to be stacked. The proper staking and folding yields biologically compatible and functional molecules. If a solvent other than water is used the folding of proteins is derailed to biologically incompatible molecules. The energetically favorable stacking and folding is accompanied by remitting of any excess energy to the microenvironment hosting the staking process (the cell in this case). The excess energy release can be in various forms including electromagnetic radiation. This could in fact explain the presence of some of the low intensity photons in the cell environment. These photons are conceivably specific to the amino-acid being staked and the configuration to which they are folded. Hence the synthesis of the various proteins could be accompanied by the emission of electromagnetic radiation. In turn this electromagnetic radiation could play a role in guiding the conformational change of other existing (already made) protein.

In-Vivo Photosynthesis (Human Photosynthesis):

It is well understood that cells, their proteins and genes are sensitive to light. A review of this area has been provided by Neves-Petersen, M. T., et al. (2012). "UV Light Effects on Proteins: From Photochemistry to Nanomedicine", Molecular Photochemistry—Various Aspects, Dr. Satyen Saha (Ed.), ISBN: 978-953-51-0446-9, InTech, the entire contents of which are incorporated herein by reference.

Just a couple of examples of photoinitiated processes in human cells include (1) the vision process, which is initiated when photoreceptor cells are activated by light (photoisomerization); and (2) near UV (290 nm) exposed prion protein fails to form amyloid fibrils (Thakur, A. K. & Mohan Rao Ch. (2008). "UV-Light Exposed Prion Protein Fails to Form Amyloid Fibrils, Plos one, Vol 3, No. 7, (July 2008), pp. E2688, eISSN 1932-6203).

Sunlight can activate the formation of vitamin D3. Interestingly, the precursor to vitamin D3 is cholesterol. Cells also produce an abundance of cholesterol sulfate the important precursor to vitamin D3. Due to the lack of depth of penetration of sunlight into the human body, the photoinduced bio-synthesis of vitamin D3 is confined to the skin area.

The benefits of vitamin D3 are actually stemming from cholesterol sulfate and lead to protection against diabetes, cardiovascular disease and certain cancers.

In view of the ability to convert X-Ray into UV light, the technology now exists to perform biosynthesis of vitamin D3 in-vivo anywhere in the human or animal body. Energy converting particles can be placed (through injection) in proximity to a cholesterol rich area and help convert such cholesterol into water soluble vitamin D3.

In one embodiment of the present invention, photonic energy from the energy converters noted above can be used to photo-excite these types of reactions to promote light-activated bio-synthesis. This can be used as a method of increasing vitamin D3 levels in a subject, lowering total cholesterol levels in a subject, or both simultaneously. Of course, the level of vitamin D3 production could be controlled by controlling the amount of incident high energy radiation (such as x-ray) which in turn would control the amount of UV production in vivo.

In another embodiment of the present invention, the photonic energy need not come from down-converting phosphors. Other means for generating ultraviolet or visible light in vivo may be used by injecting into the body in target regions upconverting phosphors, UV or visible light emitting diodes, light-emitting plasma capsules, etc. to photo-excite reactions promoting vitamin D3 production and/or other light-activated bio-synthesis.

Nucleic acids in living cells are associated with a large variety of proteins. Ultraviolet (UV) irradiation of cells is thought to lead to reactions between DNA and the proteins that are in contact with it, such as cross-linking between the amino acids in these associated proteins and the bases in DNA, which appears to be an important process that photoexcited DNA and proteins undergo in vivo, as well as in DNA-protein complexes in vitro. Twenty two (22) common amino acids are known to bind photochemically (upon 254 nm excitation) to uracil, with the most reactive being phenylalanine, tyrosine and cysteine. The three amino acid residues having side chains that absorb in the UV range are the aromatic residues tryptophan (Trp), tyrosine (Tyr) and phenylalanine (Phe).

One photochemical mechanism in proteins involves reduction of disulphide bridges upon UV excitation of Trp and Tyr side chains. As discussed by Neves-Petersen et al (2012), UV-excitation of tryptophan or tyrosine can result in their photoionization and to the generation of solvated electrons. The generated solvated electrons can subsequently undergo fast geminate recombination with their parent molecule, or they can be captured by electrophilic species like molecular oxygen, H3O+ (at low pH), and cystines (name given to each bridged cysteine in a disulphide bridge), which can also result in the breakage of the disulphide bridge. The free thiol radicals/groups thus formed can then react with other free thiol groups to create a new disulphide bridge. As detailed by Neves-Petersen et al (2012), this phenomenon has led to a new technology for protein immobilization (LAMI, light assisted molecular immobilization) since the created thiol groups can bind thiol reactive surfaces leading to oriented covalent protein immobilization.

There are many potential pathways for the breakage of intramolecular disulphide bridges in proteins upon UV excitation of aromatic residues, even in the absence of molecular oxygen. Breakage of the disulphide bridge can lead to conformational changes in the protein, not necessarily resulting in inactivation of the protein.

Neves-Petersen et al (2012) report that the solvated electron average lifetime is shorter at acidic pH values, which is correlated with the fact that H3O+ captures the solvated electron. Furthermore, the solvated electron lifetime is significantly shorter in protein systems as compared to from Trp alone in solution, thus indicating that a protein offers other pathways involving capture of the solvated electron. Neves-Petersen et al (2012) also report that data has shown that the higher the pH the longer time it takes for the solvated electron to recombine with the parent molecule (geminate recombination) or another electron scavenger molecule, such as $H3O+$. The observed lifetime increase with pH can be explained since the lower the pH, the higher the concentration of $H3O+$ and therefore the larger the probability of recombination of the solvated electron with the hydronium ion. Furthermore, for proteins, the higher the pH of the solution, the larger the number of basic titratable residues that have lost their positive charge and became neutral (His, Lys, Arg) and the larger the number of acidic titratable residues that have acquired a negative charge (Asp, Gly, Tyr, Cys not bridged). This means that an increase of pH leads to a loss of positive charge in the protein and a gain of neutral and negative charged residues in the protein. This can lead to an increase of the areas in the protein that carry a negative electrostatic potential. Therefore, an increase in pH will decrease the efficiency of electron recombination with the molecule due to electrostatic repulsion. This can lead to an increase of the solvated electron lifetime.

The recent development of DNA microarrays has demonstrated the importance of immobilization technology, where multiple oligonucleotide or cDNA samples are immobilized on a solid surface in a spatially addressable manner. These arrays have revolutionized genetic studies by making the global analysis of gene expression in living organisms more readily possible. Similar approaches have been developed for protein analysis. The proteins bound to the microarrays can be assayed for functional or structural properties, making screening possible on a scale and with a speed previously unachievable. The simplest type of protein immobilization uses the high inherent binding affinity of surfaces to proteins in general, such as through the use of numerous weak contacts, including van der Waals and hydrogen bonding interactions. Molecules can also be immobilized on a carrier or solid surface passively through hydrophobic or ionic interactions, or covalently by attachment to surface groups. Due to the importance of immobilization for solid phase chemistry and biological screening, the analytical uses of the technology have been widely explored. The technology has found particularly broad application in different areas of biotechnology, including, but not limited to, diagnostics, biosensors, affinity chromatography and immobilization of molecules in assays such as ELISA assays.

Light-induced immobilization techniques have also been explored, leading to the use of quinone compounds for photochemical linking to a carbon-containing support (see, e.g., EP0820483). Activation occurs after irradiation with non-ionizing UV and visible light. Masks can be used to activate certain areas of the support for subsequent attachment of biomolecules. Following illumination, the photochemically active compound anthraquinone will react as a free radical and form a stable ether bond with a polymer surface. Because anthraquinone is not found in native biomolecules, appropriate ligands have to be introduced into the biomolecule. A further development of light-induced immobilization technology is disclosed in U.S. Pat. Nos. 5,412,087 and 6,406,844, each of which is incorporated herein by reference in its entirety.

Most of the known immobilization methods use one or more thermochemical/chemical steps, sometimes with hazardous chemicals, some of which are likely to have a deleterious effect on the structure and/or function of the bound protein. The available methods are often invasive, whereby foreign groups are introduced into a protein to act as functional groups, which can cause protein denaturation, as well as lower its biological activity and substrate specificity. Neves-Petersen et al (2012) have suggested this can be addressed by Light Assisted Molecular Immobilization technology (LAMI). This technology provides a photonic method for coupling a protein or a peptide on a carrier by way of stable bonds (covalent bond or thiol-Au bond) while preserving the native structural and functional properties of the coupled protein or peptide.

LAMI technology uses an inherent natural property of proteins and peptides, whereby a disulphide bridge in a protein or peptide, located in close proximity to an aromatic amino acid residue, is disrupted following excitation of aromatic amino acids. The thiol groups created by light induced disulphide bridge breakage in a protein or peptide are then used to immobilise the protein or peptide to a carrier. The formed free thiol groups in the protein can then attach the protein onto a thiol reactive surface, such as gold, thiol derivatized glass and quartz, or even plastics. The new protein immobilization technology has led to the development of microarrays of active biosensors and biofunctionalization of thiol reactive nanoparticles, aiming at engineering drug delivery systems.

Exemplary Methods of the Invention

Figure 29:
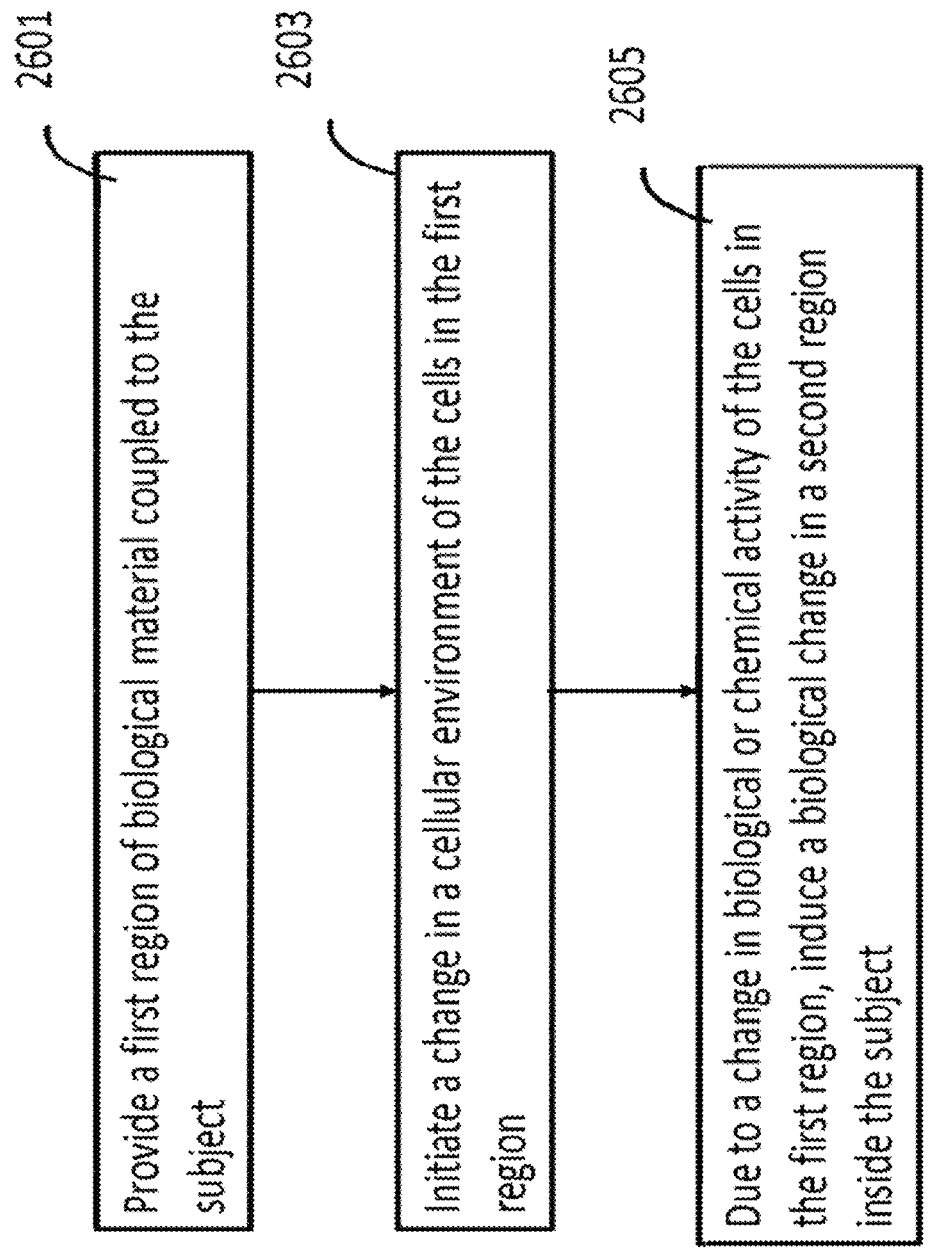
FIG. 29 is a flowchart of one method for treating a subject according to an embodiment of the present invention.

FIG. 29 is a flowchart of one method of the invention for treating a subject. At 2601, this method provides a first region of biological material coupled to the subject. At 2603, this method initiates a change in a cellular environment of the cells in the first region. At 2605, due to a change in biological or chemical activity of the cells in the first region, this method induces a biological change in a second region inside the subject.

According to various embodiments of the invention, the first region can be a region inside the subject proximate the second region or it can be a region inside the subject remote from the second region. In one embodiment, the first region can be a region outside the subject coupled physically to the second region or it can be a region inside the subject overlapping the second region.

Furthermore, at 2601, the biological material of the first region can be segregated from the second region by an artificial material. The artificial material may comprise a permeable material capable of transmission of chemical agents produced by the biological material from the first region into the second region. The artificial material may comprise a material capable of transmission of biophotons therethrough. The artificial material may comprise a material capable of transmission of sonic waves therethrough. The artificial material may comprise a material capable of transmission of ultraviolet light or visible light therethrough. The artificial material may comprise a material capable of transmission of infrared light therethrough. The artificial material may comprise a material capable of transmission of electrical signals therethrough. At 2605, the first region and the second region can be quantum entangled regions, permitting the coupling to occur.

Furthermore, at 2603, initiating a change can cause cell death of the biological material of the first region or initiating a change can cause cell growth of the biological material of the first region. The changes initialed can be caused by imposing an electric field in the first region to promote ion pumping through cells in the biological material of the first region, or by imposing an electric field in the first region to retard ion pumping through cells in the biological material of the first region. Furthermore, the changes initialed can be caused by changing a rate of transport of reagents through cell membranes cells in the biological material of the first region, for example by changing a probability of tunneling of the reagents through cell membranes. In one example, the probability of tunneling is changed by applying an electric field to promote or retard transmission of the reagents through the cell membranes in the biological material of the first region. In another example, the probability of tunneling is changed by applying a photon flux to the reagents to increase an energy of the reagents. In another example, the probability of tunneling is changed by applying a drug which thickens the cell membranes. In another example, the probability of tunneling is changed by applying a drug which dilates or constricts pores in the cell membranes. In a specialized example, the drugs affecting the cell membranes can be isolated only to the first region so that toxicity of the drug does not affect the subject.

Furthermore, at 2603, initiating a change can change a rate of enzymatic reactions occurring in the biological material or can change a rate of catalysis reactions occurring in the biological material. At 2603, initiating a change can change a rate of photosynthesis occurring in the biological material. At 2603, initiating a change can change the genomics of the biological material in the first region. This change in genomics in the first region can induce a therapeutic change in the second region.

Furthermore, at 2605, inducing a biological change in a second region inside the subject occurs by coupling to the second region via interactions of DNA molecules along a pathway from the first region to the second region. In this embodiment, the pathway may comprise as part or all the pathway signaling DNA. In one embodiment, coupling is provided by transporting charge along the signaling DNA. In one embodiment, inducing a biological change occurs by removing a protein that normally binds to signaling DNA in the biological material of the first region.

In these steps and actions above, biophotonic or mitogenic radiation from the first regions is transmitted (or otherwise coupled) to the second regions to thereby induce the change in the second region. When this coupling is via ultraviolet or visible light, the photon flux in a specialized case is that of a single photon emission and transmission, and possibly emitted and transmitted coherently with other sources of the biophoton radiation.

Optionally, in the steps and actions above, biophoton emission is stimulated by artificial sources such that living tissues in the first region produce biophoton radiation.

Optionally, in the steps and actions above, artificial or simulated biophoton emission is produced and coupled to the second or treatment region.

In these steps and actions above, a change in the viability of the cells in the first region produces a similar change in the second region of the subject.

Furthermore, at 2601, the biological material of the first region is surgically defined (isolated, separated, partially removed) from a diseased organ in the subject, a treatment is applied to the first region that had been surgically defined to promote cell death (or alternatively cell growth), thereby inducing cell death (or cell growth) as the biological change in the second region (or treatment region) of the subject. With this approach, the surgically defined first region can be selectively treated to induce cell death for example by chemically inducing cell death in the surgically defined first region or by chemically inducing cell death in the surgically defined first region by radiation. One example of such radiation can include ultraviolet light. Other examples include x-rays, gamma rays, protons, or other high energy sources.

FIG. 30 is a flowchart of another method of the invention for treating a subject. At 2701, this method provides a source of biophoton or mitogenic radiation. At 2703, this method couples the source of the biophoton radiation to a treatment site inside the patient. At 2705, the coupling induces a biological, chemical, physical, or therapeutic change in the subject at the treatment site.

These steps or actions in FIG. 30 may occur with any of the other steps and actions set forth above with regard to FIG. 29.

Strategies for Photonic Coupling to Diseased Tissue Via Cellular Communication:

One can identify a photonic energy $hv_{mp+}$ that promotes the activity of the metabolic pump (referred to as mp+ energy). Conversely, it is possible to find photonic energy that diminishes the function of the metabolic pump called $hv_{mp-}$ (referred to mp- energy). This makes it possible to target tumor cells and irradiate them with the appropriate "mp- energy" to limit their function and energy production. This approach is the deconstructive approach with the strategy of impeding the undesirable behavior (uncontrolled growth). This deconstructive approach has significant limitations in that insofar as apoptosis is not triggered in the tumor environment, even a small percentage of cancerous or mutated cells that are left behind can result in the formation of metastasis and relaunch of the disease. In fact, this is the problem of all of the state-of-the-art therapies. The eradication of disease is never complete and cancerous cells find a way to invade adjacent tissue and to recolonize mutated cells in different organs. The metastasis problem is one of the biggest issues facing all therapies.

Another strategy is referred to as the photonically constructive approach and comprises stimulating the biological circuitry to generate healthy bio-photonic signatures that in-turn communicate with the tumor micro environment (TME) to stay on a healthy course rather than to engage in undesirable mutations leading to cancer propagation. The ability to collect the bio-photonic signature from the healthy tissue and to compare it with a cancerous tissue would thus provide a feedback loop necessary to activate the biological circuitry to promote the right photonic signature. The biological circuitry can be stimulated by having an increase in the metabolic pump function.

By distinguishing diseased tissue from healthy tissue in any organ of the body, a regimen of photonic stimulus can be implemented periodically until the diseased cells go back to normal behavior and subsequently become regulated by the immune system. This constructive approach should be done first to limit the evasion of mutated cells from the surveillance of the immune system. Once the cells no longer have countermeasures to evade the immune system, then the disease is corrected quickly and efficiently by the existing (and complex) chain of events enabled by the immune system.

Since the biological circuitry can be stimulated by having an increase in the metabolic pump function, this makes it possible to stimulate the proteins gating the doorways to ion channels and to cause an increase in the uptake of ions ever so slightly to build up more voltage (hence more energy storage) which results in the decay and dissipation of said stored energy via photonic energy.

The photonic energy at the cellular level coupled with the ability to measure ultraweak photons is one preferred embodiment of the present invention. It is also recognized that photonic signatures can carry information of types not described herein. However, the ability to interact at the cellular level using photons opens a myriad of medical possibilities and novel therapies based on cellular light communication.

The following is a list of preferred Embodiments of the present invention, which is non-exhaustive:

Embodiment 1

A method of treating a subject comprising:
providing a first region of biological material coupled to the subject;
initiating a change in a cellular environment of the cells in the first region; and
due to a change in biological or chemical activity of the cells in the first region, inducing a biological change in a second region inside the subject.

Embodiment 2

The method of Embodiment 1, further comprising defining for the first region a region inside the subject proximate the second region.

Embodiment 3

The method of Embodiment 2, wherein the region inside the subject is formed of the subject's own tissue.

Embodiment 4

The method of Embodiment 2, wherein the region inside the subject is biological material implanted inside the subject.

Embodiment 5

The method of Embodiment 1, further comprising defining for the first region a region inside the subject remote from the second region.

Embodiment 6

The method of Embodiment 5, wherein the region inside the subject is formed of the subject's own tissue.

Embodiment 7

The method of Embodiment 5, wherein the region inside the subject is biological material implanted inside the subject.

Embodiment 8

The method of Embodiment 1, further comprising defining for the first region a region outside the subject coupled physically to the second region.

Embodiment 9

The method of Embodiment 1, further comprising defining for the first region a region inside the subject overlapping the second region.

Embodiment 10

The method of any one of Embodiments 1 to 9, wherein providing comprises segregating the biological material of the first region from the second region by an artificial material.

Embodiment 11

The method of Embodiment 10, wherein the artificial material comprises a permeable material capable of transmission of chemical agents produced by the biological material from the first region into the second region.

Embodiment 12

The method of Embodiment 10, wherein the artificial material comprises a material capable of transmission of biophotons therethrough.

Embodiment 13

The method of Embodiment 10, wherein the artificial material comprises a material capable of transmission of sonic waves therethrough.

Embodiment 14

The method of Embodiment 10, wherein the artificial material comprises a material capable of transmission of ultraviolet light therethrough.

Embodiment 15

The method of Embodiment 10, wherein the artificial material comprises a material capable of transmission of infrared light therethrough.

Embodiment 16

The method of Embodiment 10, wherein the artificial material comprises a material capable of transmission of electrical signals therethrough.

Embodiment 17

The method of any one of Embodiments 1 to 16, wherein the first region and the second region are quantum entangled regions.

Embodiment 18

The method of any one of Embodiments 1 to 17, wherein initiating a change comprises causing cell death of the biological material of the first region.

Embodiment 19

The method of any one of Embodiments 1 to 17, wherein initiating a change comprises causing cell growth of the biological material of the first region.

Embodiment 20

The method of any one of Embodiments 1 to 19, wherein initiating a change comprises imposing an electric field in the first region to promote ion pumping through cells in the biological material of the first region.

Embodiment 21

The method of any one of Embodiments 1 to 19, wherein initiating a change comprises imposing an electric field in the first region to retard ion pumping through cells in the biological material of the first region.

Embodiment 22

The method of any one of Embodiments 1 to 19, wherein initiating a change comprises changing a rate of transport of reagents through cell membranes cells in the biological material of the first region.

Embodiment 23

The method of Embodiment 22, wherein changing a rate of transport comprises changing a probability of tunneling of the reagents through cell membranes.

Embodiment 24

The method of Embodiment 23, wherein changing a probability of tunneling comprises applying an electric field to promote or retard transmission of the reagents through the cell membranes in the biological material of the first region.

Embodiment 25

The method of Embodiment 23, wherein changing a probability of tunneling comprises applying a photon flux to the reagents to increase an energy of the reagents.

Embodiment 26

The method of Embodiment 23, wherein changing a probability of tunneling comprises applying a drug which thickens the cell membranes.

Embodiment 27

The method of Embodiment 23, wherein changing a probability of tunneling comprises applying a drug which dilates or constricts pores in the cell membranes.

Embodiment 28

The method of Embodiment 26 or Embodiment 27, wherein the drug is isolated only to the first region so that toxicity of the drug does not affect the subject.

Embodiment 29

The method of any one of Embodiments 1 to 19, wherein initiating a change comprises changing a rate of enzymatic reactions occurring in the biological material.

Embodiment 30

The method of any one of Embodiments 1 to 19, wherein initiating a change comprises changing a rate of catalysis reactions occurring in the biological material.

Embodiment 31

The method of any one of Embodiments 1 to 19, wherein initiating a change comprises changing a rate of photosynthesis occurring in the biological material.

Embodiment 32

The method of any one of Embodiments 1 to 19, wherein initiating a change comprises changing genomics of the biological material in the first region.

Embodiment 33

The method of Embodiment 32, wherein the changing genomics in the first region induces the therapeutic change in the second region.

Embodiment 34

The method of any one of Embodiments 1 to 33, further comprising coupling to the second region via interactions of DNA molecules along a pathway from the first region to the second region.

Embodiment 35

The method of Embodiment 34, where coupling comprises having the pathway comprise signaling DNA.

Embodiment 36

The method of one of Embodiments 34 or 35, where coupling comprises transporting charge along the signaling DNA.

Embodiment 37

The method of any one of Embodiments 1 to 36, wherein initiating a change comprises removing a protein that normally binds to signaling DNA in the biological material of the first region.

Embodiment 38

The method of any one of Embodiments 1 to 37, wherein the change in the viability of the cells in the first region produces a similar change in the second region of the subject.

Embodiment 39

The method of any one of Embodiments 1-18 or 20-38, wherein providing comprises:
  surgically defining the first region from a diseased organ in the subject;
  applying a treatment to the first region to promote cell death; and
  thereby inducing cell death as the biological change in the second region of the subject.

Embodiment 40

The method of Embodiment 39, wherein applying a treatment comprises:
  selectively treating the surgically defined first region to induce cell death.

Embodiment 41

The method of Embodiment 40, wherein the selectively treating comprises chemically inducing cell death in the surgically defined first region.

Embodiment 42

The method of Embodiment 40, wherein the selectively treating comprises inducing cell death in the surgically defined first region by radiation.

Embodiment 43

The method of Embodiment 42, wherein the radiation is ultraviolet light.

Embodiment 44

The method of Embodiment 42, wherein the radiation is x-rays, gamma rays, protons, or other high energy sources.

Embodiment 45

A biophoton collector comprising:
a living cell container for holding live cells which are capable of emitting biophotons;
an integrating sphere surrounding the living cell container for collection of the biophotons; and
an exit window for transmission of the biophotons from the integrating sphere.

Embodiment 46

The collector of Embodiment 45, further comprising a stimulation window for providing radiation to the live cells for stimulation of biophotonic radiation of the biophotons.

Embodiment 47

The collector of Embodiment 45, further comprising a nozzle for supply of an effluent to the living cell container.

Embodiment 48

A biophoton collector comprising:
a living cell container for holding live cells which are capable of emitting biophotons;
an antenna surrounding the living cell container for collection of electromagnetic radiation as the emitted biophotons.

Embodiment 49

The collector of Embodiment 48, further comprising a microprocessor for storing waveform characteristics of the electromagnetic radiation.

Embodiment 50

The collector of Embodiment 48, wherein the antenna comprises a fractal antenna.

Embodiment 51

A biophoton bypass comprising:
a hollow cavity optic for transmitting biophotons from a source of the biophotons to a treatment site while bypassing media of the subject to be treated;
an exit optic attached to an end of the hollow cavity optic, the exit optic dispersing the biophotons from the hollow cavity optic Into the media of the subject to be treated.

Embodiment 52

The bypass of Embodiment 51, wherein the hollow cavity optic is filled with a gas or is under a vacuum.

Embodiment 53

The bypass of Embodiment 51, wherein the hollow cavity optic comprises reflective interior walls.

Embodiment 54

An electrically conducting biophoton bypass comprising:
a conductor for transmitting low frequency electric signals from a source of the biophotons to a treatment site while bypassing media of the subject to be treated;
a sheath covering the conductor and isolated from the conductor by a dielectric spacer;
a connector attached to the conductor for connecting the conductor to the media of the subject to be treated.

Embodiment 55

The bypass of Embodiment 54, wherein the conductor comprises multiple conductors each having respective sheaths.

Embodiment 56

The bypass of Embodiment 55, wherein the multiple conductors with the respective sheaths are twisted together to reduce high frequency noise.

Embodiment 57

An electrically conducting biophoton bypass comprising:
a conductor for transmitting high frequency electrical signals from a source of the biophotons to a treatment site while bypassing media of the subject to be treated;
a sheath covering the conductor and equidistantly spaced apart from the conductor by a dielectric spacer;
a connector attached to the conductor for connecting the conductor to the media of the subject to be treated.

Embodiment 58

A magnetic yoke biophoton bypass comprising:
a magnetic yoke for transmitting magnetic signals from a source of the biophotons to a treatment site while bypassing media of the subject to be treated;
a dual gap construction comprising a first gap for introduction of the magnetic signals into the magnetic yoke and a second gap for exposing the treatment site to the magnetic signals.

Embodiment 59

An in vivo biophoton generator comprising:
one or more phosphors disposed in an organ or at treatment site;
a controller configured to control high energy excitation of the phosphors to produce light emission from the phosphors mimicking biophoton emission from cells in the organ or at the treatment site.

Embodiment 60

The generator of Embodiment 59, wherein the controller controls e-beam or x-ray flux to the phosphors.

Embodiment 61

A living cell biophoton generator comprising:
a living cell layer comprising live cells;
a matrix for attaching the living cell layer to an organ or treatment site;
an encapsulant layer sealing the living cell layer.

Embodiment 62

The generator of Embodiment 61, wherein the encapsulant layer is configured to provide a controlled release substance to the living cell layer.

Embodiment 63

The generator of Embodiment 61, wherein the encapsulant layer comprises phosphors or metals.

Embodiment 64

A DNA-based biophoton bypass comprising:
a signaling DNA capable of transmitting electromagnetic signals as biophotons from a source of the biophotons to a treatment site while bypassing media of the subject to be treated;
a waveguide structure housing the signaling DNA,
wherein the signaling DNA and the waveguide structure transmit the electromagnetic signals a treatment site.

Embodiment 65

A living cell biophoton generator comprising:
a system for locally heating cells in an organ or treatment site;
a controller configured to control the local heating to an amount that induces stress in the cells and thereby induces biophoton emission from the cells in stress.

Embodiment 66

The generator of Embodiment 65, wherein the system comprises a microwave hyperthermia treatment system.

Embodiment 67

A method for in vivo biosynthesis of Vitamin D3 in a subject, comprising:
contacting a cholesterol rich region of the subject with one or more energy converters capable of converting an applied initiation energy into UV;
irradiating the cholesterol rich region of the subject and the one or more energy converters with the applied initiation energy, wherein the applied initiation energy is at least one member selected from the group consisting of x-rays, gamma rays, and particle beams;
wherein the applied initiation energy is converted by the one or more energy converters into UV energy, which interacts with cholesterol in the cholesterol rich region, thereby converting the cholesterol into Vitamin D3.

Embodiment 68

The method of Embodiment 67, wherein the contacting is performed by injection of the one or more energy converters into the cholesterol rich region of the subject.

Embodiment 69

The method of Embodiment 67, wherein the contacting is performed by systemically infusing the one or more energy converters into a blood vessel of the subject, wherein the cholesterol rich region of the subject is the bloodstream of the subject.

Embodiment 70

The method of any one of Embodiments 1 to 29 or Embodiments 35 to 46, wherein the biological change in the second region comprises a change in neuron activity.

Embodiment 71

The method of Embodiment 70, wherein the change in neuron activity is stimulation and/or control of neural communication.

Embodiment 72

A method for regenerative medicine, comprising:
internally generating light in a subject in need thereof at one or more wavelengths sufficient to cause regrowth/regeneration of cells or tissue in the subject.

Embodiment 73

The method of Embodiment 72, wherein the light is internally generated by administration of at least one energy modulation agent in a vicinity of the area for regrowth/regeneration of cells or tissue, and applying an initiation energy to the subject which is converted internally within the subject by the at least one energy modulation agent into the one or more wavelengths.

Embodiment 74

The method of Embodiment 72, wherein the light is internally generated by activation of a long-lived persistent phosphor external to the subject, and administering the activated long-lived persistent phosphor to the subject in a vicinity of the area for regrowth/regeneration of cells or tissue.

Embodiment 75

The method of any one of Embodiments 72 to 74, wherein the regrowth/regeneration of cells or tissue comprises angiogenesis.

Embodiment 76

The method of any one of Embodiments 72 to 75, further comprising administering to the subject a hydrogel impregnated with a RGB peptide coupled with a photo-responsive blocker, such that upon internally generating light in the subject, the photo-responsive blocker is released by the internally generated light, thus activating the RGB peptide to cause regrowth/regeneration of cells or tissue.

Embodiment 77

The method of Embodiment 76, wherein the RGB peptide coupled with a photo-responsive blocker further comprises a vascular endothelial growth factor protein complexed thereto, such that upon release of the photo-responsive blocker, each of the RGB peptide and vascular endothelial growth factor protein are activated within the subject.

Numerous modifications and variations of the invention are possible in light of the above teachings. It is therefore to be understood that within the scope of the appended claims, the invention may be practiced otherwise than as specifically described herein.

The invention claimed is:

1. A method of triggering cell-to-cell communication in a subject comprising:
providing a first region of biological material coupled to the subject;
initiating a change in a cellular environment of the cells in the first region, wherein initiating a change comprises changing a rate of transport of reagents through cell membranes of cells in the biological material of the first region by changing a probability of tunneling of the reagents through cell membranes, wherein changing a probability of tunneling comprises applying a photon flux to the reagents to increase an energy of the reagents; and
due to a change in biological or chemical activity of the cells in the first region, inducing a biological change in a second region inside the subject.

2. The method of claim 1, further comprising defining for the first region a region inside the subject proximate the second region.

3. The method of claim 2, wherein the region inside the subject is formed of the subject's own tissue.

4. The method of claim 2, wherein the region inside the subject is biological material implanted inside the subject.

5. The method of claim 1, further comprising defining for the first region a region inside the subject remote from the second region.

6. The method of claim 5, wherein the region inside the subject is formed of the subject's own tissue.

7. The method of claim 5, wherein the region inside the subject is biological material implanted inside the subject.

8. The method of claim 1, further comprising defining for the first region a region inside the subject overlapping the second region.

9. The method of claim 1, wherein providing comprises segregating the biological material of the first region from the second region by an artificial material.

10. The method of claim 9, wherein the artificial material comprises a material capable of transmission of biophotons therethrough.

11. The method of claim 1, wherein the first region and second region are quantum entangled regions.

12. A method of triggering cell-to-cell communication in a subject comprising:
providing a first region of biological material coupled to the subject;
initiating a change in a cellular environment of the cells in the first region; and
due to a change in biological or chemical activity of the cells in the first region, inducing a biological change in a second region inside the subject by coupling to the second region via interactions of DNA molecules along a pathway from the first region to the second region, where coupling comprises having the pathway comprise signaling DNA.

13. A method of triggering cell-to-cell communication in a subject comprising:
providing a first region of biological material coupled to the subject;
initiating a change in a cellular environment of the cells in the first region; and
due to a change in biological or chemical activity of the cells in the first region, inducing a biological change in a second region inside the subject by coupling to the second region via interactions of DNA molecules along a pathway from the first region to the second region, where coupling comprises having the pathway comprise signaling DNA and transporting charge along the signaling DNA.

14. The method of claim 1, wherein the biological change is a change in viability and wherein the change in the viability of the cells in the first region produces a similar change in the second region of the subject.

15. The method of claim 1, wherein the biological change in the second region comprises a change in neuron activity.

16. The method of claim 15, wherein the change in neuron activity is stimulation and/or control of neural communication.

17. The method of claim 12, further comprising defining for the first region a region inside the subject proximate the second region.

18. The method of claim 17, wherein the region inside the subject is formed of the subject's own tissue.

19. The method of claim 17, wherein the region inside the subject is biological material implanted inside the subject.

20. The method of claim 12, further comprising defining for the first region a region inside the subject remote from the second region.

21. The method of claim 20, wherein the region inside the subject is formed of the subject's own tissue.

22. The method of claim 20, wherein the region inside the subject is biological material implanted inside the subject.

23. The method of claim 12, further comprising defining for the first region a region inside the subject overlapping the second region.

24. The method of claim 12, wherein providing comprises segregating the biological material of the first region from the second region by an artificial material.

25. The method of claim 24, wherein the artificial material comprises a material capable of transmission of biophotons therethrough.

26. The method of claim 12, wherein the first region and the second region are quantum entangled regions.

27. The method of claim 12, wherein the biological change is a change in viability and wherein the change in the viability of the cells in the first region produces a similar change in the second region of the subject.

28. The method of claim 12, wherein the biological change in the second region comprises a change in neuron activity.

29. The method of claim 28, wherein the change in neuron activity is stimulation and/or control of neural communication.

30. The method of claim 13, further comprising defining for the first region a region inside the subject proximate the second region.

31. The method of claim 30, wherein the region inside the subject is formed of the subject's own tissue.

32. The method of claim 30, wherein the region inside the subject is biological material implanted inside the subject.

33. The method of claim 13, further comprising defining for the first region a region inside the subject remote from the second region.

34. The method of claim 33, wherein the region inside the subject is formed of the subject's own tissue.

35. The method of claim 33, wherein the region inside the subject is biological material implanted inside the subject.

36. The method of claim 13, further comprising defining for the first region a region inside the subject overlapping the second region.

37. The method of claim 13, wherein providing comprises segregating the biological material of the first region from the second region by an artificial material.

38. The method of claim 37, wherein the artificial material comprises a material capable of transmission of biophotons therethrough.

39. The method of claim 13, wherein the first region and the second region are quantum entangled regions.

40. The method of claim 13, wherein the biological change is a change in viability and wherein the change in the viability of the cells in the first region produces a similar change in the second region of the subject.

41. The method of claim 13, wherein the biological change in the second region comprises a change in neuron activity.

42. The method of claim 41, wherein the change in neuron activity is stimulation and/or control of neural communication.

* * * * *